(12) United States Patent
Alonso Sampedro et al.

(10) Patent No.: US 10,725,050 B2
(45) Date of Patent: Jul. 28, 2020

(54) METHOD FOR SEPARATING THE FRACTION BOUND TO GLYCOSAMINOGLYCANS AND APPLICATIONS THEREOF

(71) Applicants: UNIVERSIDADE DE SANTIAGO DE COMPOSTELA, Santiago de Compostela, La Coruña (ES); SERVIZO GALEGO DE SAUDE (SERGAS), Santiago de Compostela, La Coruña (ES); FUNDACIÓN INSTITUTO DE INVESTIGACIÓN SANITARIA DE SANTIAGO DE COMPOSTELA, Santiago de Compostela, La Coruña (ES)

(72) Inventors: Manuela Alonso Sampedro, La Coruña (ES); Víctor Álvarez González, La Coruña (ES); Cristóbal Colón Mejeras, La Coruña (ES); Miguel A. García González, La Coruña (ES); Olaya Lamas González, La Coruña (ES)

(73) Assignees: SERVIZO GALEGO DE SAUDE (SERGAS), Santiago de Compostela, a Coruña (ES); UNIVERSIDADE DE SANTIAGO DE COMPOSTELA, Santiago de Compostela, a Coruña (ES); FUNDACIÓN INSTITUTO DE INVESTIGACIÓN SANITARIA DE SANTIAGO DE COMPOSTELA, Santiago de Compostela, la Coruña (ES)

( * ) Notice: Subject to any disclaimer, the term of this patent is extended or adjusted under 35 U.S.C. 154(b) by 176 days.

(21) Appl. No.: 15/759,321

(22) PCT Filed: Sep. 9, 2016

(86) PCT No.: PCT/ES2016/070637
§ 371 (c)(1),
(2) Date: Mar. 12, 2018

(87) PCT Pub. No.: WO2017/042416
PCT Pub. Date: Mar. 16, 2017

(65) Prior Publication Data
US 2018/0328939 A1  Nov. 15, 2018

(30) Foreign Application Priority Data

Sep. 10, 2015  (ES) .................. 201531297

(51) Int. Cl.
*G01N 33/68* (2006.01)
*G01N 33/53* (2006.01)
*G01N 33/50* (2006.01)
*G01N 33/58* (2006.01)

(52) U.S. Cl.
CPC ..... *G01N 33/6839* (2013.01); *G01N 33/5091* (2013.01); *G01N 33/53* (2013.01); *G01N 33/585* (2013.01); *G01N 2400/40* (2013.01); *G01N 2800/04* (2013.01); *G01N 2800/50* (2013.01); *G01N 2800/52* (2013.01)

(58) Field of Classification Search
None
See application file for complete search history.

(56) References Cited

U.S. PATENT DOCUMENTS

| 4,540,884 A | 9/1985 | Stafford et al. |
| 5,397,894 A | 3/1995 | Wells et al. |

FOREIGN PATENT DOCUMENTS

| WO | 2010078515 A2 | 7/2010 |
| WO | 2013116677 A2 | 8/2013 |

OTHER PUBLICATIONS

Panin, G. et al.; "Simple Spectrophotometric Quantification of Urinary Excretion of Glycosaminoglycan Sulfates," 1986. Clinical Chemistry. vol. 32, No. 11, pp. 2073-2078.
Barbosa, I. et al.; "Improved and simple micro assay for sulfated glycosaminoglycans quantification in biological extracts and its use in skin and muscle tissue studies," 2003. Glycobiology. vol. 13, No. 9, pp. 647-653.
Van de Lest, C.H.A. et al.; "A spectrophotometric method for the determination of heparan sulfate," 1994. Biochimica et Biophysica Acta. vol. 1201, pp. 305-311.
Whitley C.B. et al.; "Diagnostic Test for Mucopolysaccharidosis. I. Direct Method for Quantifying Excessive Urinary Glycosaminoglycan Excretion," 1989. Clin. Chem., 35(3):374-379.
Jong J.G.N. et al.; Measuring Urinary Glycosaminoglycans in the Presence of Protein: An Improved Screening Procedure for Mucopolysaccharidoses Based on Dimethylmethylene Blue, 1992. Clin. Chem., 38(6):803-807.
Nissen, W.M.A.; "Liquid Chromatography-mass spectrometry General principles and instrumentation," Journal of Chromatography A, 703, 1995: 37-57.

(Continued)

Primary Examiner — Changhwa J Cheu
(74) Attorney, Agent, or Firm — Tristan A. Fuierer; Olive Law Group, PLLC

(57) ABSTRACT

The present invention is comprised in the field of glycobiology. In particular, it relates to a method for separating, in biological samples, the fraction bound to or associated with sulfated glycosaminoglycans (GAGs), and the applications thereof in biomedicine, such as for identifying the profile of glycoproteins or the profile of lipids bound to or associated with sulfated GAGs, detecting an alteration in the pattern of glycosylation by sulfated GAGs, identifying biomarkers for the diagnosis, for the prognosis, for monitoring the progression of a disease or of the effect of a therapy, or for identifying compounds suitable for the treatment of a disease. The invention also relates to methods for diagnosing mucopolysaccharidosis and for diagnosing and determining the prognosis of a kidney disease.

7 Claims, 20 Drawing Sheets

Specification includes a Sequence Listing.

(56) References Cited

OTHER PUBLICATIONS

Tencer J. et al.; "Decreased excretion of urine glycosaminoglycans as marker in renal amyloidosis," Nephrol Dial Transplant. 1997;12(6):1161-6.
Tencer J. et al.; "Decreased excretion of glycosaminoglycans in patients with primary glomerular diseases," Clin Nephrol. 1997;48(4):212-9.
Vermylen C. et al.; "Glomerular and urinary heparan sulphate in congenital nephrotic syndrome," Pediatr Nephrol. 1989;3(2):122-9.
Jurétic D. et al.; "Urinary Glycosaminoglycans in Different Phases of Balkan Endemic Nephropathy," Nephron. 1993;65(4):564-7.
Rodriguez-Cuartero et al.; "Urinary excretion of glucosaminoglycans in patients with a renal transplant," Clin Nephrol. 1997;47(4):274-6.
Hesse et al.; "The Excretion of Glycosaminoglycans in the Urine of Calcium Oxalate-Stone Patients and Healthy Persons," Urol. Int. 1986;41(2):81-7.
Pérez Blanco et al.; "Urinary Excretion of Glycosaminoglycans in Patients with Early Diabetic Nephropathy," Nephron, 1996;73(2):344-5.
Tokoro T. et al.; "Increased urinary excretion of acid mucopolysaccharides and glycopeptides in hypothyroidism following thyroid hormone therapy," Eur J Pediatr. May 1985;144(1):84-6.
Nikiforovskaia LF et al.; "Glycosaminoglycans and glycan hydrolases in the kidney of rats with hereditary diabetes insipidus," Vopr Med Khim. 1987;33(1):91-6 (only abstract in English. Original document is in Russian, not provided).
Kery V. et al.; "Urinary Glycosaminoglycan Excretion in Rheumatic Diseases," Clin Chem. 1992;38(6):841-6.
Elaev N.R., et al.; "Anomalous excretion of glycosaminoglycans in patients with syringomyelia," Biull Eksp Biol Med. 1992;114(9):271-2 (only abstract in English. Original document is in Russian, not provided).
Tomatsu S. et al.; "Newborn screening and diagnosis of mucopolysaccharidoses," 2013. Mol. Genet. Metab. 110(0):42-53.
Altschul, S., et al..; "Basic Local Alignment Search Tool," J. Mol. Biol., 215:403-410 (1990).
Christianson et al.,; "Cancer cell exosomes depend on cell-surface heparan sulfate proteoglycans for their internalization and functional activity," Proc Natl Acad Sci USA 2013, 110:17380-5.
Hogan et al.,; "Characterization of PKD Protein-Positive Exosome-Like Vesicles," J Am Soc Nephrol 2009, 20:278-288.
Al-Nedawi K. et al.; "Intercellular transfer of the oncogenic receptor EGFRvlll by microvesicles derived from tumour mils," 2008. Nature Cell Biology, vol. 10, pp. 619-624.
Bach G et al.; "The Defect in the Hurler and Scheie Syndromes: Deficiency of alpha-L-Iduronidase," 1972. PNAS, vol. 69, No. 8, pp. 2048-2051.
Bates Jm et al.; "Tamm-Horsfall protein knockout mice are more prone to urinary tract infection," 2004. Kidney Int., 65(3):791-7.
Benito-Martin A. et al.; "Osteoprotegerin in Exosome-Like Cesicles from Human Cultured Tubular Cells and Urine," 2013. PLoS One, 8(8):e72387.
Berman ER et al.; "A Reliable Spot Test for Mucopolysaccharidoses," 1977 Clin Chem., 17(9):886-90.
Blackham, G. A. et al.; "The Biochemistry of the Mucopolysaccharidoses," 1970. Ann. Clin. Biochem., 6,49-54.
Boyan BD. et al.; "1alpha, 25(OH)2D3 is an Autocrine Regulator of Extracellular Matrix Turnover and Growth Factor Release via ERp60 Activated Matrix Vesicle Metalloproteinases," 2007. J Steroid Biochem Mol Biol., 103(3-5): 467-472.
Byers S et al.; "Glycosaminoglycan Accumulation and Excretion in the Mucopolysaccharidoses: Characterization and Basis of a Diagnostic Test for MPS," 1998. Mol Genet Metab, 65: 282-290.
Darisipudi MN et al.; "Uromodulin Triggers IL-1Beta-Dependent Innate Immunity via the NLRP2 Inflammasome," 2012. J Am Soc Nephrol., 23(11):1783-9.
Dean MF. et al.; "Proteoglycans from Sheep, Pig, Rat and Human Spleens Having Chemical and Biological Resemblances to that in Kurloff Cells," 1971. FEBS Lett.16(3):183-185.

Dear JW et al.,"Urinary exosomes: A reservoir for biomarker discovery and potential mediators of intrarenal signalling," 2013. Proteomics,13(10-11):1572-80.
Denny W. et al.; "Simple Urine Test for Gargoylism," 1962. British Medical Journal, 1(5291): 1555-1556.
de Jong JG et al.; "Mucopolysaccharidoses screening: dimethylmethylene blue versus Alcian blue," 1994. Ann Clin Biochem, 31: 267-271.
de Ruijter J et al.; "Heparan sulfate and dermatan sulfate derived disaccharides are sensitive markers for newborn screening for mucopolysaccharidoses types I, II, III," 2012. Mol Genet Metab, 107: 705-710.
del Cacho E. et al.; "Induction of Protective Immunity against Eimeria tenella, Eimeria maxima, and Eimeria acervulina Infections Using Dendritic Cell-Derived Exosomes," 2012. Infect Immun. 80(5):1909-16.
El-Achkar TM et al; "Uromodulin in Kidney Injury: An Instigator, Bystander, or Protecto?" 2012. Am J Kidney Dis.59(3):452-461.
Fernández-Llama P et al; "Tamm-Horsfall protein and urinary exosome isolation," 2010. Kidney Int.77(8):736-42.
Gandhi NS. et al.; "The Structure of Glycosaminoglycans and their Interactions with Proteins," 2008. Chem Biol Drug Des, 72: 455-482.
Górriz Teruel JL et al.; "Impacto socio sanitario de la enfermedad renal crónica avanzada," 2008. Nefrologia, 28 Suppl 3:7-15. [article in Spanish; abstract in English].
Hiemstra TF et al.; "Uromodulin Exclusion List Improves Urinary Exosomal Protein Identification," 2011. J Biomol Tech. 22(4):136-45.
Hiemstra TF et al.; "Human Urinary Exosomes as Innate Immune Effectors," 2014. J Am Soc Nephrol.25(9):2017-27.
Hoerger TJ et al.; "The Future Burden of CKD in the United States: A Simulation Model for the CDC CKD Initiative," 2015. Am J Kidney Dis. 65(3):403-11.
Hogan MC et al.; "Identification of Biomarkers for PKD1 Using Urinary Exosomes," 2015. J Am Soc Nephrol, 26: 1661-1670.
Hogan MC et al.; "Characterization of PKD Protein-Positive Exosome-Like Vesicles," 2009. J Am Soc Nephrol, 20: 278-288.
Hoorn EJ et al.; "Prospects for urinary proteomics: Exosomes as a source of urinary biomarkers," 2005. Nephrology (Carlton), 10(3):283-90.
Kanno K et al.; "Urinary Excretion of Aquaporin-2 in Patients with Diabetes Insipidus," 1995. N Engl J Med, 332:1540-1545.
Kreft B et al.; "Polarized Expression of Tamm-Horsfall Protein by Renal Tubular Epithelial Cells Activates Human Granulocytes," 2002. Infect Immun., 70(5):2650-6.
Kresse H.; "Mucopolysaccharidosis III A (Sanfilippo A Disease) L Deficiency of A Heparin Sulfamidase in Skin Fibroblasts and Leucocytes," 1973. Biochem Biophys Res Commun, 54(3):1111-1118.
Lawrence R et al.; "Glycan-based biomarkers for mucopolysaccharidoses," 2014. Mol Genet Metab, 111(2): 73-83.
Colón Mejeras C.; "Proyecto FIND: La importancia de diagnóstico precoz," 2015. Ada Pediatr Esp, 73(3):56-59. [Abstract in English].
Braunlin E. et al.; "Cardiac Functional and Histopathologic Findings in Humans and Mice with Mucopolysaccharidosis Type I: Implications for Assessment of Therapeutic Interventions in Hurler Syndrome," 2006. Pediatric Research, 59(1):27-32.
Biocolor: "BlyscanTM Sulfated Glycosaminoglycan Assay; Internet Manual," 2012. pp. 1-12.
Salim S. El-Amouri et al.; "Normalization and Improvement of CNS Deficits in Mice With Hurler Syndrome After Long-term Peripheral Delivery of BBB-targeted Iduronidase," 2014. Molecular Therapy, 22(12):2028-2037.
Müller G. et al.; "Quantitative and Qualitative Analyses of Proteoglycans in Cartilage Extracts by Preciptation with 1,9 Dimethylmethylene Blue," 1996. Connective Tissue Research, 33(4):243-248.
Farndale R. et al.; "Improved quantitation and discrimination of sulphated glycosaminoglycans by use of dimethylmethylene blue," 1986. Biochimica et Biophysica Acta, 883(2):173-177.
Bhavanandan V.P. et al.; "Quantitation of of urinary glycosaminoglycans with Alcian blue: evaluation of interference by Tamm-Horsfall glycoprotein," 1996. Clinica Chimica Acta, 251(2):207-214.

(56) References Cited

OTHER PUBLICATIONS

Lee MK et al.; "Analysis of affinity and structual selectivity in the binding of proteins to glycosaminoglycans: Development of a sensitive electrophoretic approach," 1991. Proc Natl Acad Sci USA, 88: 2768-2772.
Lehman TJA et al.; "Diagnosis of the mucopolysaccharidoses," 2011. Rheumatology, 50: v41-v48.
Liu Y et al.; "Tamm-Horsfall Protein Regulates Circulating and Renal Cytokines by Affecting Glomerular Filtration Rate and Acting as a Urinary Cytokine Trap," 2012. J Biol Chem. 287(20):16365-78.
Manley G. et al.; "Diagnosis of Hurler's Syndrome in the Hospital Laboratory and the Determination of its Genetic Type," 1966. Arch. Dis. Childh., 41, 91.
Matalon R, et al.; "Hurler's Syndrome, An Alpha-L-Iduronidase Deficiency," 1972. Biochem Biophys Res Commun., 47(4):959-64.
Matalon R. et al.; "Morquio's Syndrome: Deficiency of a Chondroitin Sulfate N-Acetylehexosamine Sulfate Sulfatase," 1974. Biochem Biophys Res Commun., 61(2):759-65.
Pennock CA.; "A Modified Screening Test for Glycosaminoglycan Excretion," 1969. J Clin Pathol., 22(3):379-80.
Pérez-Aguilar MC et al.; "Incomplete O-glycosylation in cancer cells and parasites: biomedical significance," 2013. Salus online, 17: 58-67. [article in Spanish; abstract in English].
Piraud M et al.; "Pitfalls of Screening for Mucopolysaccharidoses by the Dimethylmethylene Blue Test," 1993. Clin Chem, 39: 163.
Pisitkun T et al.; "Identification and proteomic profiling of exosomes in human urine," 2004. Proc Natl Acad Sci U S A., 101(36):13368-73.
Procopis PG et al.; "Screening Tests for Mucopolysaccharidosis," 1968. J Ment Defic Res., 12(1):13-7.
Raposo G. et al.; "B Lymphoctes Secrete Antigen-presenting Vesicles," 1996. J Exp Med, 183(3):1161-72.
Renuart AW.; "Screening for Inborn Errors of Metabolism Associated with mental Deficiency or Neurologic Disorders or Both," 1966. N Engl J Med, 274:384-387.
Rodriguez F et al.; "Mucopolisacaridosis," 2003. Salud UIS, 35: 135-144. [Article in Spanish; abstract in English].
Rosenfeld L.; "Quantitative Levels of the Constituents of Acid Mucopolysaccharides and Other Carbohydrate Polymers in Dialyzed Normal Human Urine," 1971. Clinica Chimica Acta, vol. 31, Issue 1, pp. 263-269.
Sanchez-Niño MD et al.; "Uromodulin, Inflammasomes, and Pyroptosis," 2012. J Am Soc Nephrol. 23(11):1761-3.
Segni G. et al.; "Diagnostic Test for Gargoylism," 1964. Lancet, 2(7356):420.
Serafini-Cessi F. et al.; "Tamm-Horsfall Glycoprotein: Biology and Clinical Relevance," 2003. Am J Kidney Dis, 42 :658-676.
Sirois I et al.; "Caspase-3-dependent export of TCTP: a novel pathway for antiapoptotic intercellular communication," 2011. Cell Death Differ,18(3):549-62.
Sjöberg I et al.; "Hunters Syndrome: A Deficiency of L-Idurono-Sulfate Sulfatase," 1973. Biochem Biophys Res Commun, 54(3):1125-1132.
Sly WS et aL; "Beta glucuronidase deficiency: Report of clinical, radiologic, and biochemical features of a new mucopolysaccharidosis," 1973. J Pediatr, 82(2):249-57.
Street JM et al.; "Exosomal transmission of functional aquaporin 2 in kidney cortical collecting duct cells," 2011. J Physiol., 589(Pt 24):6119-27.
Stumpf DA et al.; "Mucopolysaccharidosis Type VI (Maroteaux-Lamy Sundrome)" 1973. Am J Dis Child. 126(6):747-55.
Tamm I et al.; "A Mucoprotein Derived from human Urine Which Reacts with Influenza, Mumps, and Newcastle Disease Viruses," 1952. J Exp Med. 95(1):71-97.
Tomatsu S et al.; "Development and Testing of New Screening Method for Keratan Sulfate in Mucopolysaccharidosis IVA," 2004. Pedriatr Res, 55: 592-597.
Tomatsu S et al.; "Heparan sulfate levels in mucopolysaccharidoses and mucolipidoses," 2005. J Inheri Metab Dis, 28: 743-757.
Valdivieso F et al.; "Early Diagnosis of Hypermucopolysacchariduria," 1973. Clinica Chimica Acta, 44: 357-360.
Von Figura K et al.; "Sanfilippo B disease: Serum assays for detecion of homozygous and hererozygous individuals in tree families," 1973. J Pediatr. 83(4):607-11.
Waldenstrom A et al.; "Cardiomyocyte Microvesicles Contain DNA/RNA and Convey Biological Messages to Target Cells," 2012. PLoS One, 7(4): e34653.
Wolf MT et al.; "Uromodulin Upregulates TRPV5 by Impairing Caveolin-Mediated Endocytosis," 2013. Kidney Int., 84(1):130-7.

Dimethylmethylene blue

Double dimethylmethylene blue zinc chloride salt

B) SDS-PAGE Sypro Staining

Uromodulin Western Blot

Albumin Western Blot a)

b)

Mean size of UGE complexes: 199.5 ± 69.31 nm c)

Mean charge of UGE complexes: neutral d)

a)

b)

SEQUENCE LISTING

```
<160> NUMBER OF SEQ ID NOS: 2

<210> SEQ ID NO 1
<211> LENGTH: 24
<212> TYPE: PRT
<213> ORGANISM: Homo sapiens

<400> SEQUENCE: 1

Met Gly Gln Pro Ser Leu Thr Trp Met Leu Met Val Val Val Ala Ser
1               5                   10                  15

Trp Phe Ile Thr Thr Ala Ala Thr
            20

<210> SEQ ID NO 2
<211> LENGTH: 30
<212> TYPE: PRT
<213> ORGANISM: Homo sapiens

<400> SEQUENCE: 2

Met Gly Gln Pro Ser Leu Thr Trp Met Leu Met Val Val Val Ala Ser
1               5                   10                  15

Trp Phe Ile Thr Thr Ala Ala Thr Asp Thr Ser Glu Ala Arg
            20                  25                  30
```

METHOD FOR SEPARATING THE FRACTION BOUND TO GLYCOSAMINOGLYCANS AND APPLICATIONS THEREOF

CROSS-REFERENCE TO RELATED APPLICATIONS

This application is filed under the provisions of 35 U.S.C. § 371 and claims the priority of International Patent Application No. PCT/ES2016/070637 filed on 9 Sep. 2016 entitled "METHOD FOR SEPARATING THE FRACTION BOUND TO GLYCOSAMINOGLYCANS AND APPLICATIONS THEREOF" in the name of Manuela ALONSO SAMPEDRO, et al., which claims priority to Spanish Patent Application No. P201531297, filed on 10 Feb. 2015, both of which are hereby incorporated by reference herein in their entirety.

FIELD OF THE INVENTION

The present invention is comprised in the field of glycobiology. In particular, it relates to a method for separating, in biological samples, the fraction bound to or associated with sulfated glycosaminoglycans and the applications thereof in biomedicine.

BACKGROUND OF THE INVENTION

Glycosaminoglycans (GAGs) are large unbranched polysaccharides formed by repeating disaccharide sequences, in which one of the components is always an amino sugar (D-galactosamine or D-glucosamine) and the other component is a uronic acid, such as L-glucuronic or L-iduronic, with the exception of keratan sulfate. Except for hyaluronic acid, all GAGs have sulfate groups, such as O-esters or N-sulfate.

GAGs are part of proteoglycans and lipids. Proteoglycans are a specific type of glycoproteins having at least one GAG chain bound to the protein, and they are classified based on the GAG chain present.

The glycosylation of molecules is a post-translational enzymatic process carried out in the endoplasmic reticulum and Golgi apparatus. Glycosylation reactions are performed by enzymes called glycosyltransferases from monosaccharide precursors of endogenous and exogenous origin.

Diseases relating to congenital alterations in glycosylation include mucopolysaccharidoses (MPS). MPS are a heterogeneous group of innate metabolism errors caused by the deficiency of any of the enzymes necessary for the degradation of GAGs. Non-degraded GAGs are usually partially excreted in the urine, but the rest are accumulated in the lysosomes. This accumulation causes cellular alterations and interferences in other metabolic processes with serious consequences for the human body, leading to cell, tissue, and organ damage.

Seven types of MPS with several subtypes involving 11 specific enzymes have been described up until now. Each type of MPS has nonspecific signs and symptoms, and some alterations considered "characteristic", although they still require performing a precise diagnosis of these diseases by means of determining the enzyme activity involved, and in the best case scenario, performing molecular identification of the affected gene. They are usually difficult to detect in newborns, and an early and precise diagnosis of MPS is critical in order to provide suitable palliative care, and when possible, a treatment specific for the disease (enzyme replacement therapy, hematopoietic stem cell transplant, among others).

The diagnosis of most MPS is not easy and is mainly based on clinical findings. Once a suspicion is established, the physician may count on certain analytical tests such as urine GAG analysis and quantification of enzyme activity in tissues (blood or fibroblasts). Finally, the physician may request the performance of molecular biology techniques to confirm the possible genetic alteration.

Colorimetric methods measuring the increase in GAG compared to the expected levels of GAGs in normal individuals of the same age have been used for quantifying total GAGs in urine. Several assays in which dimethylmethylene blue (DMB) is used as a dye have been described. GAGs bind to DMB and the compound that is formed is detected by means of spectrophotometry. Nevertheless, isolation of the GAG-DMB complex that is formed does not take place (Whitley C. B. et al. 1989. Clin. Chem., 35(3):374-379; Jong J. G. N. et al. 1992. Clin. Chem., 38(6):803-807). However, they have a high percentage of false positives and false negatives, and due to their low specificity, they do not allow discriminating between the different types of GAG.

Methods for assaying specific GAGs which seek to identify the types of GAGs that are excreted in excess and help to provide a better diagnosis, given that the different types of MPS are associated with the increased excretion of specific GAGs, have also been developed. Those which stand out the most among these methods are chromatographic methods, such as HPLC, which despite being sensitive and specific, are not suitable for massive screening due to the high cost and long analysis time required; ELISA methods which are commercially available for certain types of GAGs, but have not been developed for detecting all GAGs; and tandem mass spectrometry methods that have the drawback of being complex due to the molecular heterogeneity of GAGs and difficulty in applying same for mass screening.

GAG depolymerization methods measuring the hexuronic acid residues that all GAGs have (except for keratan sulfate) have also been developed. This measurement is performed directly in the dialysis liquid, after fractionating the sample in an ECTEOLA cellulose column (separating sulfated GAGs from non-sulfated GAGs), or after precipitating it with cetyltrimethylammonium bromide (CTAB), cetylpyridinium chloride (CPC), or aminoacridine. These methods consume a lot of time and provide barely reproducible results due to the interference of other chromogens, or due to the loss of some GAG fractions in prior treatments.

There are also diseases relating to acquired alterations in glycosylation, such as kidney diseases. Acquired or congenital kidney diseases are a major public health concern worldwide. A recent prospective study conducted in the United States indicates that 54% of adults between 30-49 years of age, 52% of adults between 50-64 years of age, and 42% of adults above 65 years of age, are affected by chronic kidney disease, and an increase between 13.2% and 14.4% is expected in 2020, and an increase of 16.7% is expected in 2030. The diagnosis of said disease is based on measuring a series of clinical parameters in urine (glomerular filtration rate or GFR calculated through the levels of creatinine, cystatin C or inulin, proteinuria, hematuria, etc.), imaging techniques (mainly ultrasounds, computed tomography (CT), or nuclear magnetic resonance (NMR)), and anatomical pathology (by means of biopsies obtained in an invasive manner). All of them have a limited differential diagnostic power and none is capable of anticipating the progression of the kidney disease over time in an accurate and efficient manner. These tools furthermore have limited specificity and sensitivity.

There is therefore a need for new methods for detecting the fractions bound to or associated with GAGs which overcome the drawbacks of the methods known up until now, which allow a quick, sensitive, reliable, cost-effective and less invasive diagnosis in early stages of the disease, which can be used for massive screening in newborns, and which allow detecting and/or prognosticating diseases such as MPS or a kidney disease.

BRIEF DESCRIPTION OF THE INVENTION

The authors of the present invention have developed a new method for separating the fraction bound to sulfated glycosaminoglycans (GAGs) in biological samples. This method allows studying alterations in the glycosylation of GAGs in a manner that is simple, quick, and cost-effective and requires a very small amount of sample (microliters). This method has various applications in biomedicine, such as in the diagnosis and prognosis of diseases occurring with alterations in levels of GAGs, in the search for biomarkers for the diagnosis of these diseases, in follow-up of the pathology or of the treatment thereof, etc. Conventional methods require large volumes of sample and many previous steps.

The method of the present invention is based on the fact that GAGs, depending on the tissue in which they are found, tend to be associated with other molecules, either for functional reasons or as a result of mechanical interactions. Although interferences in measurements due to other molecules that were invariably purified together with GAGs have already been described in some assays of the state of the art, no one has looked into an ulterior practical application with respect to this association.

Particularly, the present invention relates to the capacity of the dimethylmethylene blue (DMB) dye at acidic pH to produce complexes with sulfated GAGs, giving rise to the formation of turbidity, followed quickly by the precipitation of this DMB-GAG complex in about 15 minutes. After centrifugation, the precipitate contains only the fraction bound to sulfated GAGs. The rest is eliminated from the sample. This precipitate can then be used for analyzing the fraction by various techniques such as denaturing electrophoresis in polyacrylamide gels (SDS-PAGE) and staining with a dye for viewing proteins, such as Sypro Ruby. The bands obtained in the electrophoresis can be identified by means of Western blot or can also be cleaved for identification by means of proteomics.

The method of the invention combines the DMB property of specifically binding to and precipitating sulfated GAGs with protein and/or lipid analysis techniques. By detecting fractions specifically glycated with GAGs, this method has a very high potential as it can be used in studies in which glycation/glycosylation plays an important role and can allow discovering new diagnostic biomarkers, prognostic biomarkers or biomarkers for follow-up of pathologies, new therapeutic targets and new cell communication pathways.

Therefore, in a first aspect, the present invention relates to an in vitro method for separating free sulfated glycosaminoglycans (GAGs) and the fraction bound to or associated with sulfated GAGs from a sample.

The second and third aspects of the invention relate to an in vitro identification method for identifying the profile of proteins bound to or associated with sulfated GAGs of a sample.

In a fourth aspect, the invention relates to an in vitro identification method for identifying the profile of lipids bound to or associated with sulfated GAGs of a sample.

In a fifth aspect, the invention relates to an in vitro method for detecting an alteration in the pattern of glycosylation by sulfated GAGs of a sample.

The invention also relates to diagnostic methods, methods for determining the prognosis, for monitoring the progression, for monitoring the effect of a therapy, and for identifying compounds suitable for the treatment of diseases associated with an alteration (increased or decrease) of one or more sulfated GAGs.

The invention also relates to the use of the method of the second, third, fourth, or fifth aspects for identifying protein or lipid biomarkers bound to or associated with sulfated GAGs.

In another aspect, the invention relates to an in vitro method for diagnosing mucopolysaccharidosis in a subject which comprises detecting, in a urine sample from said subject, the presence of the signal peptide SEQ ID NO: 1 of uromodulin or of a variant thereof.

The invention also relates to methods for determining the prognosis, for monitoring the progression of a subject, for monitoring the effect of a therapy, for designing a personalized therapy, or for selecting a patient susceptible to being treated with a therapy for the prevention and/or treatment of mucopolysaccharidosis, and to methods for identifying compounds suitable for the treatment of mucopolysaccharidosis.

In another aspect, the invention relates to the use of an agent capable of detecting the signal peptide SEQ ID NO: 1 of uromodulin or a variant thereof in a urine sample for diagnosing mucopolysaccharidosis, for determining the prognosis or for monitoring the progression of a subject suffering from mucopolysaccharidosis, for monitoring the effect of a therapy in a subject suffering from mucopolysaccharidosis, for designing a personalized therapy in a subject having symptoms of mucopolysaccharidosis, for selecting a patient susceptible to being treated with a therapy for the prevention and/or treatment of mucopolysaccharidosis, or for identifying compounds suitable for the treatment of mucopolysaccharidosis, wherein the agent capable of detecting the signal peptide SEQ ID NO: 1 of uromodulin or a variant thereof is selected from the group consisting of an enzyme capable of specifically recognizing an amino acid sequence of the signal peptide of SEQ ID NO: 1 of uromodulin or of a variant thereof and cleaving said peptide, an antibody, an aptamer, and fragments thereof that bind specifically to the signal peptide SEQ ID NO: 1 of uromodulin or to a variant thereof.

In another aspect, the invention relates to the use of the signal peptide SEQ ID NO: 1 of uromodulin or a variant thereof as a diagnostic marker, as a prognostic marker, as a marker for monitoring the progression of a subject suffering from mucopolysaccharidosis, or as a marker for monitoring the effect of a therapy, as a marker for designing a personalized therapy, as a marker for selecting a patient susceptible to being treated with a therapy for the prevention and/or treatment of mucopolysaccharidosis, or as a marker for identifying compounds suitable for the treatment of mucopolysaccharidosis.

In another aspect, the invention relates to methods for the diagnosis, for the prognosis, or for monitoring the progression of a kidney disease, monitoring the effect of a therapy, methods for designing a personalized therapy, or for selecting a patient susceptible to being treated with a therapy for the prevention and/or treatment of a kidney disease, and methods for identifying compounds suitable for the treatment of a kidney disease.

In another aspect, the invention relates to the use of an agent capable of detecting uromodulin or a variant thereof bound to or associated with sulfated GAGs selected from the group consisting of an enzyme capable of specifically recognizing an amino acid sequence of uromodulin or of a variant thereof and cleaving it, an antibody, an aptamer, and fragments thereof that bind specifically to uromodulin or to a variant thereof, and/or of an agent capable of detecting albumin or a variant thereof bound to or associated with sulfated GAGs selected from the group consisting of an enzyme capable of specifically recognizing an amino acid sequence of albumin or of a variant thereof and cleaving it, an antibody, an aptamer, and fragments thereof that bind specifically to albumin or to a variant thereof in a urine sample for diagnosing a kidney disease, for determining the prognosis or for monitoring the progression of a subject suffering from a kidney disease, for monitoring the effect of a therapy in a subject suffering from a kidney disease, for designing a personalized therapy in a subject having symptoms of a kidney disease, for selecting a patient susceptible to being treated with a therapy for the prevention and/or treatment of a kidney disease, or for identifying compounds suitable for the treatment of a kidney disease.

In another aspect, the invention relates to the use of uromodulin or a variant thereof bound to or associated with sulfated GAGs, and/or of albumin or of a variant thereof bound to or associated with sulfated GAGs as a diagnostic marker for a kidney disease, as a prognostic marker for a kidney disease, as a marker for monitoring the effect of a therapy in a subject suffering from a kidney disease, as a marker for designing a personalized therapy in a subject having symptoms of a kidney disease, as a marker for selecting a patient susceptible to being treated with a therapy for the prevention and/or treatment of a kidney disease, or as a marker for identifying compounds suitable for the treatment of a kidney disease.

In another aspect, the invention relates to an in vitro method for diagnosing an advanced kidney disease in a subject which comprises detecting the level of uromodulin- or uromodulin variant-sulfated GAG-exosomes complexes in a urine sample from said subject, and comparing said level with a reference value, wherein a decreased level of uromodulin- or uromodulin variant-sulfated GAG-exosomes complexes with respect to the reference value is indicative of the subject suffering from an advanced kidney disease.

The invention also relates to methods for determining the prognosis or for monitoring the progression of an advanced kidney disease, or for monitoring the effect of a therapy, designing a personalized therapy, or selecting a patient susceptible to being treated with a therapy for the treatment of an advanced kidney disease, or to methods for identifying compounds suitable for the treatment of an advanced kidney disease.

In another aspect, the invention relates to the use of an agent capable of detecting uromodulin- or uromodulin variant-sulfated GAG-exosomes complexes in a urine sample for diagnosing an advanced kidney disease, for determining the prognosis or for monitoring the progression of a subject suffering from an advanced kidney disease, for monitoring the effect of a therapy in a subject suffering from an advanced kidney disease, for designing a personalized therapy in a subject having symptoms of an advanced kidney disease, for selecting a patient susceptible to being treated with a therapy for the treatment of an advanced kidney disease, or for identifying compounds suitable for the treatment of an advanced kidney disease, wherein the agent capable of detecting uromodulin- or uromodulin variant-sulfated GAG-exosomes complexes is selected from the group consisting of an enzyme capable of specifically recognizing an amino acid sequence of uromodulin or of a variant thereof and cleaving it, an antibody, an aptamer, and fragments thereof that bind specifically to uromodulin or to a variant thereof.

In another aspect, the invention relates to the use of a uromodulin- or uromodulin variant-sulfated GAG-exosomes complex as a diagnostic marker for an advanced kidney disease, as a prognostic marker for an advanced kidney disease, as a marker for monitoring the effect of a therapy in a subject suffering from an advanced kidney disease, as a marker for designing a personalized therapy in a subject having symptoms of an advanced kidney disease, as a marker for selecting a patient susceptible to being treated with a therapy for the treatment of an advanced kidney disease, or as a marker for identifying compounds suitable for the treatment of an advanced kidney disease.

In another aspect, the invention relates to a complex formed by the association of uromodulin or a uromodulin variant, sulfated GAGs, and exosomes.

In another aspect, the invention relates to a kit comprising dimethylmethylene blue (DMB) at a concentration comprised between 0.01 and 100 mM at a pH comprised between 2 and 6.9.

In another aspect, the invention relates to a kit comprising an antibody capable of specifically detecting a peptide of sequence SEQ ID NO: 1 or a variant thereof, and incapable of detecting mature uromodulin, or a fragment of said antibody with the capacity to bind to sequence SEQ ID NO: 1 or to a variant thereof.

In another aspect, the invention relates to the use of the kit of the invention for separating the free sulfated GAGs and the fraction bound to or associated with sulfated GAGs from a sample, for identifying the profile of proteins bound to or associated with sulfated GAGs of a sample, for identifying the profile of lipids bound to or associated with sulfated GAGs of a sample, for detecting an alteration in the pattern of glycosylation by sulfated GAGs, for diagnosing a disease, for determining the prognosis of a disease, for monitoring the progression of a disease, for monitoring the effect of a therapy for the treatment of a disease, for predicting the response to a therapy, for designing a personalized therapy, for identifying compounds suitable for the treatment of a disease, for identifying protein or lipid biomarkers bound to or associated with sulfated GAGs, or for detecting complexes formed by exosomes, sulfated GAGs, and a protein.

DETAILED DESCRIPTION OF THE INVENTION

Separation Method for Separating Sulfated GAGs

In a first aspect, the invention relates to an in vitro method (referred to as "first method of the invention") for separating the free sulfated glycosaminoglycans (GAGs) and the fraction bound to or associated with sulfated GAGs from a sample, which comprises:
  a) contacting a sample with the dimethylmethylene blue (DMB) dye at an acidic pH comprised between 2 and 6.9;
  b) incubating the mixture from a) at a temperature comprised between 0° C. and 40° C. for the time required for the formation of a precipitate;
  c) removing the supernatant; and
  d) recovering the precipitate containing free sulfated GAGs and the fraction bound to or associated with sulfated GAGs.

Figure 1:
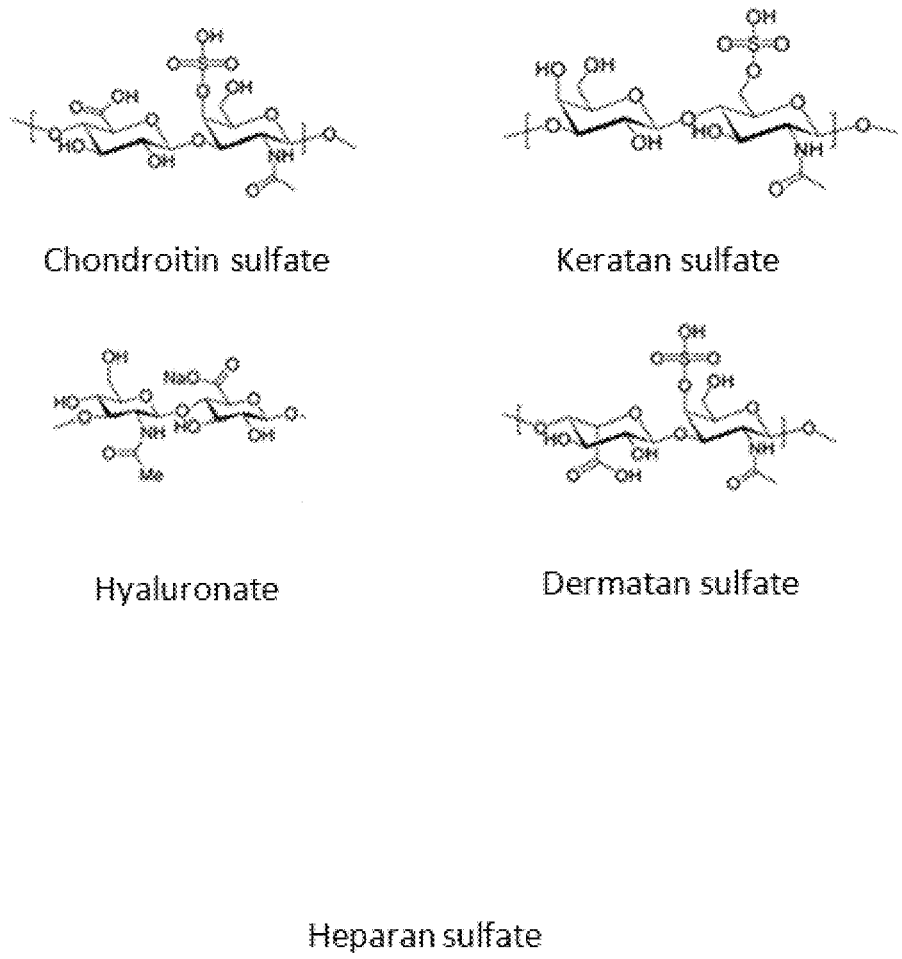
FIG. 1: Molecular structures of glycosaminoglycans (GAGs) chondroitin sulfate, keratan sulfate, hyaluronate, dermatan sulfate, and heparan sulfate.
Figure 1:
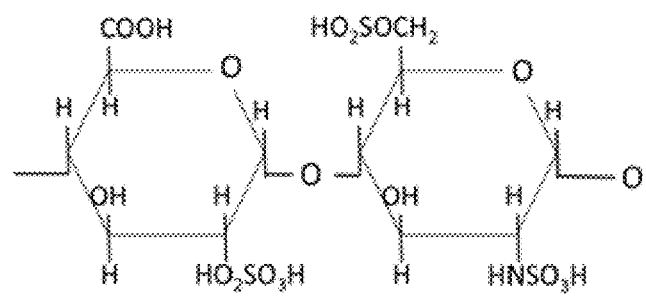

As it is used herein, the term "glycosaminoglycan" or "GAG", also called mucopolysaccharide, refers to a heteropolysaccharide formed by repetitions of disaccharide units. Glycosaminoglycans are linear chains in which β 1→3 bonds alternate with β 1→4 bonds of a uronic acid (D-glucuronic or L-iduronic) bound by means of a β 1→3 bond to an amino sugar (N-acetyl-glucosamine or N-acetylgalactosamine). GAGs are differentiated according to the nature of the disaccharide units forming them, the length of the disaccharide chain (10-150 units), and the modifications thereof (N-sulfation, 0-sulfation, N-acetylation, or epimerization of the saccharide units). The following seven GAGs stand out among those of biological interest: hyaluronic acid (HA), chondroitin-4-sulfate (C4S), chondroitin-6-sulfate (C6S), dermatan sulfate (DS) or chondroitin sulfate B, keratan sulfate (KS), heparan sulfate (HS), and heparin (HEP). They have a high density of negative electrical charge due to the introduction of acidic groups (carboxy, esterified sulfates, and sulfamide) in their structure. They undergo variable degrees of sulfation, where the sulfate esterified to alcoholic OH increases their polyanionic character. The number of negative charges per disaccharide unit varies between 1, in the case of hyaluronic acid and keratan sulfate, and 4 in the case of heparin. FIG. 1 shows the structure of the most well-known GAGs.

As it is used herein, the term "sulfated glycosaminoglycan" or "sulfated GAG", also called sulfated mucopolysaccharide, refers to those GAGs having at least one sulfate group. With the exception of hyaluronic acid, all GAGs are sulfated. Therefore, sulfated GAGs that can be separated according to the method of the present invention include, without limitation, chondroitin-4-sulfate (C4S), chondroitin-6-sulfate (C6S), dermatan sulfate (DS) or chondroitin sulfate B, keratan sulfate (KS), heparan sulfate (HS), and heparin (HEP).

Sulfated GAGs can be found in a sample in free form, or bound to or associated with other components. "Free sulfated GAGs" are understood as those GAGs that are not bound to or associated with any other component. Furthermore, however, sulfated GAGs can also be found bound to other compounds, forming glycoconjugates, such as glycoproteins, proteoglycans, and lipids bound to or associated with GAGs.

As it is used herein, the term "glycoprotein" or "glucoprotein" refers to a molecule that is usually formed by one or more oligosaccharides covalently bound to specific side polypeptide chains. They usually have a higher percentage of proteins than carbohydrates. In the context of the present invention, at least one of the carbohydrates forming the glycoprotein must be a sulfated GAG. The most common types of glycoproteins found in eukaryotic cells are defined according to the nature of the protein-binding regions, where those of N- and O-type are the most common. N-glycans are an oligosaccharide chain covalently bound to an asparagine residue of a polypeptide chain within a consensus sequence Asn-X-Ser/Thr, generally through N-acetylglucosamine (Glc-NAc). O-glycans are an oligosaccharide chain covalently bound to a serine or threonine residue (Ser/Thr-O), generally through N-acetylgalactosamine (GalNAc).

As it is used herein, the term "proteoglycan" or "PG" refers to a specific type of glycoproteins that have at least one GAG chain bound to the protein and are classified based on the GAG chain present. In the context of the present invention, the GAGs bound to the protein must be sulfated GAGs. Heparan sulfate and chondroitin sulfate are the most common GAGs of proteoglycans. Many proteoglycans furthermore contain other glycans bound by N- or O-glycosidic type bonds. These compounds may vary in terms of their tissue distribution, the nature of the central protein, their function, and the GAGs fixed thereto. The carbohydrate content is greater than the glucoprotein content, reaching up to 95% of the weight thereof in some cases, and both the sequence and the arrangement of the structural domains forming them are highly conserved and slightly glycated As it is used herein, the term "lipid bound to or associated with GAGs" refers to a molecule formed by one or more sulfated GAGs bound to lipids by means of a covalent bond, or associated with them in any other way.

As it is used herein, "fraction bound to sulfated GAGs of a sample" is understood as any compound that is bound to sulfated GAGs by means of a covalent bond. Examples of these compounds are, without limitation, glucoproteins containing sulfated GAGs and proteoglycans. In a preferred embodiment, the fraction bound to sulfated GAGs is a protein fraction. In another preferred embodiment, the fraction bound to sulfated GAGs is a lipid fraction.

As it is used herein, "fraction associated with sulfated GAGs of a sample" is understood as any compound or structure which is not bound to sulfated GAGs by means of a covalent bond, but rather the sulfated GAGs and the compound or structure are held together by means of interactions of another type, such as ionic interactions, dipole-dipole interactions, Van der Waals interactions, or hydrogen bridges, among others. In a preferred embodiment, the fraction associated with sulfated GAGs is a fraction containing exosomes, more preferably a fraction containing exosomes and one or more proteins.

As it is used herein, the term "exosomes" refers to small extracellular nanovesicles (50-200 nm) surrounded by a membrane, said nanovesicles originating from the endocytic pathway and being released by different cell types into most biological fluids, including urine. They are also secreted by cells in vitro. Their functions include, among others, intercellular RNA and membrane receptor traffic, induction of immunity and antigen presentation, modulation of bone mineralization, and anti-apoptotic responses. Their membranes are rich in proteins involved in transport and fusion, as well as lipids such as cholesterol, sphingolipids, ceramides, etc. Exosomes are identified in that they show a range of density between 1.13 and 1.19 g/ml when separated in a sucrose gradient, and in that they possess a series of markers such as CD63, CD81, CD9, ALIX, FLOT1, ICAM1, EpCam, ANXA5, TSG101, and Hsp70 which can be detected, for example, by means of antibodies. The fraction associated with sulfated GAGs of the invention can be an exosome from any type of sample, for example, without limitation, an exosome from cell culture media, blood, urine, amniotic fluid, and ascitic fluid. In a preferred embodiment, the exosomes were isolated from urine. Methods for isolating exosomes from samples and biological fluids are well known to one skilled in the art.

The inventors have identified various complexes formed by exosomes and one or more proteins in urine samples, as demonstrated in Table II in the experimental part. In a particular embodiment, the fraction associated with sulfated GAGs is a complex formed by uromodulin (or a variant thereof) and exosomes. In another particular embodiment, the fraction associated with sulfated GAGs is a complex formed by albumin (or a variant thereof) and exosomes. In another particular embodiment, the fraction associated with sulfated GAGs is a complex formed by IgA (or a variant thereof) and exosomes. In another particular embodiment, the fraction associated with sulfated GAGs is a complex formed by IgG (or a variant thereof) and exosomes.

In the context of the first method of the invention, The term "sample" refers to any type of sample which contains or is susceptible of containing sulfated GAGs. In a preferred embodiment, the sample is a biological sample.

As it is used herein, the term "biological sample" refers to any material originating from a human being, animals, or plants which can store information relating to their genetic endowment. Examples of biological samples that can be used in the present invention are, without limitation, samples of urine, serum, plasma, tissues, cells, exosomes, synovial fluid, vitreous humor, cerebrospinal fluid, skin, intestinal mucosa, peritoneal fluid, arterial wall, bone, cartilage, embryonic tissue, and umbilical cord, etc. In a preferred embodiment, the biological sample is a urine sample. In another preferred embodiment, the biological sample is a sample of exosomes, preferably a sample of exosomes previously isolated from a subject, more preferably a sample of exosomes isolated from the urine of a subject. In another preferred embodiment, the biological sample is a serum or plasma sample.

The sample is obtained under the conditions and in the receptacle that work best for preserving the integrity of said sample. In the case of urine, the second morning urine must be collected, discarding the first urine, in protease-free containers. In the case of blood, it must be collected in a suitable tube depending on whether work will be done with serum (an STII or biochemical tube) or with plasma (tube with anticoagulant, for example heparin).

After collection, the starting sample is processed according to its nature, and particularly before possible storage. In the case of urine, separation of the non-soluble cell fraction and its supernatant must be performed. In the case of blood samples, the cell fraction must be separated from the serum or plasma according to standard conditions.

Sample must be conserved at low temperatures, ideally at −80° C. The freezing-thawing cycles may compromise sample integrity and give rise to underestimations of the GAG content and of the bound or associated fraction thereof.

Samples of another type are obtained, processed and conserved according to standard techniques known by one skilled in the art. For example, exosomes are obtained from the urine supernatant obtained as described above by subjecting the supernatant to centrifugation at 5,000 g for 20 minutes, followed by filtration through 0.22 μm low protein adsorption filters, and then ultracentrifugation at 100,000 g for 2 hours. The exosomes are resuspended in a buffer, for example PBS, and stored at −20° C. The exosomes can also be isolated by means of commercial kits.

For clinical samples, the sample must be obtained with as much information as possible about the clinical history of the patient as well as all the biochemical parameters available for the correct interpretation of the results. Performing a preliminary classification of the pathological stage of the individual before taking the sample is recommended.

Immediately before separating the sulfated GAGs using the method of the invention, it is sometimes necessary to prepare the sample by means of dilution, particularly for serum or plasma samples, diluting the sample according to the envisaged concentration of sulfated GAGs and the fraction bound to or associated with them.

The first step of the first method of the invention consists of contacting the sample from which the free sulfated GAGs or the fraction bound to or associated with sulfated GAGs are to be separated with the dimethylmethylene blue (DMB) dye at an acidic pH comprised between 2 and 6.9.

This contacting involves mixing the sample and DMB until obtaining a homogeneous mixture.

Figure 2:
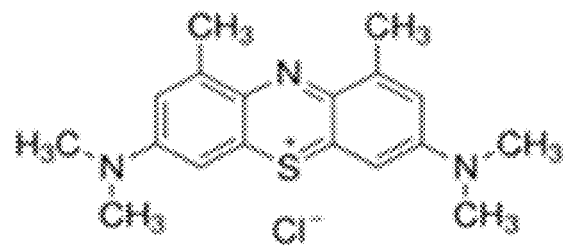
FIG. 2: Molecular structure of the DMB. A) 3,7-bis-(dimethylamino)-1,9-dimethyldiphenothiazin-5-ium chloride B) double 3,7-bis-(dimethylamino)-1,9-dimethyldiphenothiazin-5-ium zinc chloride salt.
Figure 2:
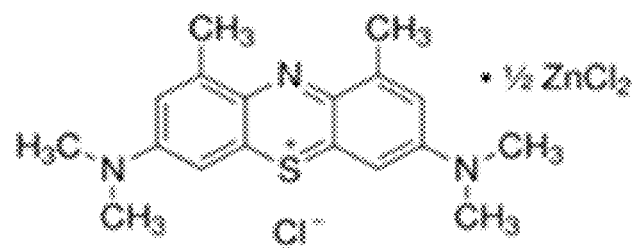

As it is used herein, the term "dimethylmethylene blue" or "DMB" refers to a cationic dye, also known as 1,9-dimethylmethylene blue, comprising the compound 3,7-bis-(dimethylamino)-1,9-dimethyldiphenothiazin-5-ium and any salt thereof. The salts thereof include, among others, salts with anions derived from inorganic acids, for example and without limitation, hydrochloric acid, sulfuric acid, phosphoric acid, diphosphoric acid, bromic acid, iodide, nitric acid, and organic acids, for example and without limitation, citric acid, fumaric acid, maleic acid, malic acid, mandelic acid, ascorbic acid, oxalic acid, succinic acid, tartaric acid, benzoic acid, acetic acid, methanesulfonic acid, ethanesulfonic acid, benzenesulfonic acid, cyclamic acid, or p-toluenesulfonic acid. In a preferred embodiment, the DMB is 3,7-bis-(dimethylamino)-1,9-dimethyldiphenothiazin-5-ium chloride, the structure of which is shown in the top part of FIG. 2. The term DMB also includes mixed salts. In a preferred embodiment, DMB is a double 3,7-bis-(dimethylamino)-1,9-dimethyldiphenothiazin-5-ium zinc chloride salt, the structure of which is shown in the bottom part of FIG. 2. These compounds can be acquired commercially.

At acidic pH, DMB is capable of binding specifically to sulfated GAGs due to the negative charge thereof. DMB has been used for quantifying GAGs, but it has always been considered that a major limitation of this method is that the DMB-sulfated GAG complexes are unstable in solution and precipitate. Up until now, no one has thought of utilizing this feature as an advantage for separating GAGs from a sample.

DMB is a powder substance which is dissolved in a suitable solvent, such as for example, ethanol, until reaching a suitable concentration. In a preferred embodiment, DMB is at a concentration ranging between 0.01 and 100 mM, preferably between 0.29 and 0.35 mM, more preferably at 0.29 mM. In a preferred embodiment, the solvent in which the dye is dissolved is ethanol.

DMB used in the first method of the invention must be at an acidic pH comprised between 2 and 6.9.

The term "pH" refers to the measurement of the acidity or alkalinity of a solution. pH typically ranges from 0 to 14 in an aqueous solution, where solutions with pH below 7 are acidic and solutions having pH above 7 are alkaline. pH=7 indicates the neutrality of the solution, where the solvent is water. The pH of a solution can be precisely determined by means of a potentiometer (or pH-meter), and it can also estimated by means of indicators, by methods that are well known in the state of the art. Given that the pH value may vary with temperature, in the context of this invention the pH is measured at 20° C. DMB used in the first method of the invention has a pH measured at 20° C. comprised between 2 and 6.9; preferably comprised between 3 and 4; more preferably comprised between 3.3 and 3.6. In a preferred embodiment, the pH measured at 20° C. is 3.5.

For the DMB dissolved in a suitable solvent to have an acidic pH, a buffer agent must be added. In the context of the present invention, "buffer agent" is understood as an agent capable of controlling the acidic pH of the solution and keeping it constant at a pH comprised between 2 and 6.9. Buffer agents suitable for the present invention are, without limitation, acetate buffer, phosphate citrate buffer, diphosphate buffer, formate buffer, and a combination thereof. In a preferred embodiment of the invention, the buffer agent is sodium formate, preferably 0.2 M sodium formate at pH 3.5. In a preferred embodiment, the buffer agent is mixed with DMB previously dissolved in a suitable solvent such as ethanol, in a DMB dissolved/buffer ratio of 1/99 to 10/90. Preferably, the DMB dissolved/buffer ratio is 1/99.

The sample to be analyzed containing the free sulfated GAGs and GAGs bound to or associated with other components must be mixed with buffered DMB in a suitable sample:buffered DMB ratio so that saturation occurs, such as the ratio comprised in the interval of 1:1 to 1:5. Preferably, they are mixed in a ratio of 1:2.

In step b) of the first method of the invention, the mixture of step a) is incubated at a temperature comprised between 0° C. and 40° C. for the time required for the formation of a precipitate. In this step, the dimethylmethylene blue dye binds specifically to free GAGs and GAGs bound to or associated with other compounds, forming complexes therewith and giving rise to the formation of turbidity, followed quickly by the precipitation of the complex that is formed. Incubation can be performed at a temperature comprised between 0° C. and 40° C., preferably between 4° C. and 30° C., more preferably between 10° C. and 28° C., even more preferably between 15° C. and 25° C., still more preferably between 20° C. and 25° C. Incubation will be performed in a cold environment, in a temperate environment, or in an oven depending on the temperature to be reached using methods known to one skilled in the art. In a preferred embodiment, incubation is performed at room temperature (between 20° C. and 25° C.)

In the context of the first method of the invention, "precipitate" is understood as the insoluble solid that is produced by the complex formed between the sulfated GAGs present in the sample to be analyzed and DMB. In most cases, the precipitate drops to the bottom of the solution and its formation can be seen with the naked eye. In other cases, the precipitate can float or remain in suspension, depending on if it is less dense than or as dense as the rest of the solution.

The incubation time is the time required for the formation of the precipitate and can be determined by one skilled in the art by simple observation of the solution or by methods known in the state of the art. Once the precipitate is formed, it can remain unchanged for days in a temperature range comprised between 0° C. and 40° C. In a preferred embodiment, the incubation time is comprised between 1 minute and 2 hours, where it is preferably at least 1 minute, at least 5 minutes, at least 10 minutes, at least 15 minutes, at least 20 minutes, at least 30 minutes, at least 40 minutes, at least 50 minutes, at least 60 minutes, at least 90 minutes. In a more preferred embodiment, the time required for the formation of the precipitate is at least 15 minutes.

In step c) of the method of the invention, the supernatant is removed after precipitation. This removal can be performed by means of any method known to one skilled in the art, for example, by filtration, decanting or by a process for the centrifugation and suction of the supernatant. In a preferred embodiment, centrifugation is performed after step b). In a preferred embodiment, the removal is performed by centrifugation and subsequent decanting or suction of the supernatant, more preferably by centrifugation and subsequent suction of the supernatant, even more preferably by centrifugation at 10,000 g for 10 minutes at 4° C. and subsequent suction of the supernatant. After centrifugation, the precipitate contains only free sulfated GAGs bound to DMB and the fraction bound to or associated with sulfated GAGs. The supernatant contains the leftover, which is removed from the sample.

Figure 3:
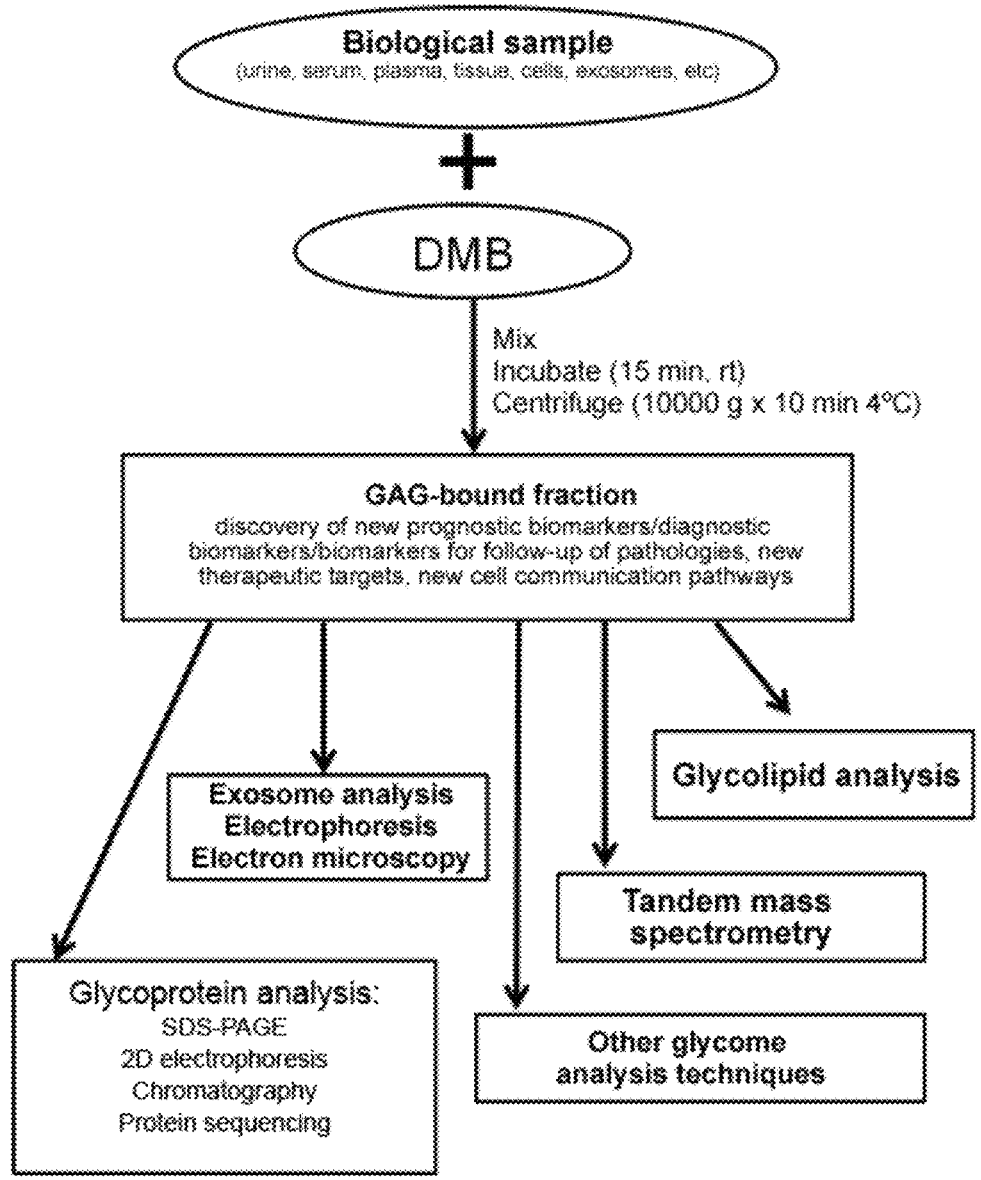
FIG. 3: Diagram of the invention and the applications thereof in biomedicine. DMB, dimethylmethylene blue; min, minutes; rt, room temperature; GAGs: glycosaminoglycans

In step d) of the first method of the invention, the precipitate containing free sulfated GAGs and the fraction bound to or associated with sulfated GAGs is recovered. This recovery may simply consist of obtaining the isolated precipitate separately from the supernatant after step c). Optionally, the precipitate obtained after step c) can be dissolved or mixed with a suitable solvent or solution depending on the subsequent use to be made of the precipitate. For example, if the precipitate is going to be analyzed by means of protein electrophoresis, it can be resuspended in a loading buffer for electrophoresis with or without SDS. In a preferred embodiment, the precipitate is resuspended in 7.5% SDS. If the precipitate is going to be analyzed by means of chromatography or protein sequencing, it can be resuspended in a buffer suitable for carrying out these techniques. FIG. 3 shows a diagram with different analysis possibilities.

Identification Method for Identifying the Profile of Proteins Bound to or Associated with Sulfated GAGs When the fraction bound to or associated with sulfated GAGs precipitated by means of the first method of the invention is a protein fraction, the obtained precipitate can be used for identifying patterns or profiles of proteins characteristic of a specific condition, whether pathological or not, or of a specific sample.

The analysis of the protein fraction can be analyzed by various techniques such as, for example, without limitation, protein electrophoresis, chromatography, mass spectrometry, or protein sequencing.

Therefore, in another aspect, the invention relates to an in vitro identification method (hereinafter "second method of the invention") for identifying the profile of proteins bound to or associated with sulfated GAGs of a sample, which comprises:

a) separating the protein fraction bound to or associated with sulfated GAGs from a sample according to the first method of the invention;
b) separating the product obtained in a) by electrophoresis; and
c) identifying the electrophoretic profile obtained in b).

In the context of the second method of the invention, the term "protein" refers to any molecule formed by amino acids bound by peptide bonds and therefore includes peptides and proteins as well as fragments thereof, including those which are post-translationally modified. Any protein post-translationally modified with GAG or otherwise associated with GAG can be identified by means of the second method of the invention. In a preferred embodiment, the protein is selected from the group consisting of uromodulin, albumin, IgA, IgG or a variant thereof and fragments thereof.

In the context of the second method of the invention, "profile of proteins" is understood as the specific pattern of proteins formed by the fraction bound to or associated with GAGs. The profile of proteins can be qualitative, quantitative, or both. In this document, the profile of proteins refers not only to the set of proteins of a known nature that have been identified by means of a specific antibody (specific profile), but rather it also refers to the pattern of bands obtained after electrophoretic separation, although it is not possible to relate each band with a specific protein (unspecific profile).

These proteins can be directly bound to or associated with sulfated GAGs or indirectly through other compounds bound to or associated with sulfated GAGs, such as exosomes.

The first step (step a) of the second method of the invention comprises separating the protein fraction bound to or associated with sulfated GAGs according to the first method of the invention.

The precipitate obtained in step a) must be resuspended in a medium suitable for being used in step b) of the method. Any loading buffer for electrophoresis may be suitable for resuspension. Examples of media in which it can be resuspended are, without limitation, 7.5% SDS; Laemli buffer; Laemli buffer with β-mercaptoethanol and 7.5% SDS in a 1:1 ratio; TBE buffer (100 mM Tris-borate, 1 mM EDTA, pH 8.3) with 2 M sucrose and 0.02% bromophenol blue; TAE buffer (40 mM Tris, 5 mM CH3COONa, 0.9 mM EDTA, pH 7.9); TBE buffer with 2 M sucrose; etc. The buffer preferred for resuspension of the precipitate is 7.5% SDS (sodium dodecyl sulfate) which is subsequently combined with the loading buffer at a variable ratio of 1:1 to 1:10. If the amount of precipitate is very large, it may be necessary to vortex the mixture to achieve complete homogenization.

Step b) of the second method of the invention is the electrophoretic separation of the product obtained in step a). "Electrophoretic separation" or "electrophoresis" is understood as a separation method for separating the components of a sample by means of applying an electrical field. In the context of the second method of the invention, electrophoretic separation is protein electrophoresis. Depending on the type of separation used, the electrophoretic separation can be zone electrophoresis (separation depending on the load), isoelectric focusing (separation depending on the isoelectric point), and size exclusion in a molecular sieve. Examples of electrophoretic separation are, without limitation, zone electrophoresis (in paper, cellulose acetate, agarose, polyacrylamide and capillary electrophoresis), isoelectric focusing, native polyacrylamide gel electrophoresis (PAGE) or denaturing polyacrylamide gel electrophoresis (SDS-PAGE). One skilled in the art will recognize that the electrophoretic separation can be one-dimensional or two-dimensional, for example, when isoelectric focusing is used as the first dimension and polyacrylamide gel electrophoresis is used as the second dimension. The electrophoretic separation or electrophoresis is carried out by methods known to one skilled in the art.

In a preferred embodiment, the electrophoresis is SDS-PAGE. In another preferred embodiment, the electrophoresis is a two-dimensional electrophoresis.

In a preferred embodiment, the electrophoresis is polyacrylamide gel electrophoresis. In another preferred embodiment, the electrophoresis is cellulose acetate gel electrophoresis.

In step c) of the method of the invention, the electrophoretic profile obtained in b) is identified.

In the context of the second method of the invention, the term "electrophoretic profile" refers to the specific pattern of bands or spots produced by the protein fraction bound to or associated with GAGs when the proteins are separated by means of electrophoresis. This specific pattern may be due to several causes: a) each type of GAG binds to a different fraction; b) the binding of the GAG to the proteins and peptides means that this fraction is secreted into a fluid, or, for example, excreted in urine; and c) the excess GAG means that specific isoforms are formed.

"Identifying the electrophoretic profile" requires either displaying a pattern of protein bands or spots which can be identified by means of their molecular weight although their nature is unknown, or else identifying the protein bands or spots by means of using an antibody which specifically recognizes a specific protein, by means of protein sequencing, or by means of mass spectrometry.

In a preferred embodiment, step c) of the second method of the invention is performed by means of Western blot, i.e., by means of using antibodies which specifically recognize a specific protein. This technique is well known to one skilled in the art.

In another preferred embodiment, step c) is performed by means of staining with a dye specific for viewing proteins.

In the context of the second method of the invention, "staining" refers to the action of staining the protein bands such that they acquire a color or fluorescence and can be detected. Protein staining protocols are known to one skilled in the art.

The term "dye specific for viewing proteins" refers to a compound which has a specific affinity for proteins and which, upon binding to said proteins, allows viewing the protein bands of a gel after electrophoretic separation either by observing the color thereof with the naked eye or by detecting fluorescence emission after illuminating with UV light, blue light, or laser. Examples of dyes specific for proteins are, without limitation, silver staining, Coomassie blue, Blue Silver or Coomassie G250, negative staining (with zinc or copper), Ponceau S, and fluorescent staining. Examples of fluorescent stains are, without limitation, Sypro Ruby, Emerald (specifically stains glycated proteins), Flamingo™ (Bio-Rad), Oriole™ (Bio-Rad), Pro-Q, labeling with Cy2, Cy3, and/or Cy5, etc. In a preferred embodiment, the dye specific for viewing proteins is Sypro Ruby.

As one skilled in the art knows, the dye to be used will depend on the subsequent analysis to which the sample is going to be subjected. For example, staining with silver is not used if analysis is to be performed by means of mass spectrometry; whereas the fluorescent stain or Coomassie G250 stain are compatible with mass spectrometry.

In a preferred embodiment, after staining with a dye specific for viewing proteins, the bands or spots obtained are cleaved from the gel and identified by means of proteomics. Among those the proteomics techniques that can be used are, without limitation, non-colorimetric techniques, such as mass spectrometry, protein sequencing, refractive index spectroscopy, ultraviolet (UV) spectroscopy, fluorescence analysis, radiochemical analysis, near infrared spectroscopy, nuclear magnetic resonance (NMR) spectroscopy, mass spectrometry pyrolysis, Raman scatter spectroscopy, ionic spray spectroscopy combined with mass spectrometry and capillary electrophoresis. Preferably, the techniques used are selected from the group consisting of mass spectrometry and protein sequencing.

"Mass spectrometry" or MS analysis is understood as an analytical technique for identifying unknown compounds including: (1) ionizing compounds and potentially fractionating the parent ions of compounds formed into daughter ions; and (2) detecting the charged compounds and calculating a mass to charge ratio (m/z). The compounds can be ionized and detected by any suitable means. A "mass spectrometer" includes means for ionizing compounds and detected charged compounds.

Preferably, mass spectrometry is used, particularly gas chromatography-mass spectrometry (GC-MS), liquid chromatography-mass spectrometry (LC-MS), direct infusion mass spectrometry or Fourier transform ion cyclotron resonance mass spectrometry (FT-ICR-MS), capillary electrophoresis-mass spectrometry (CE-MS), high performance liquid chromatography coupled with mass spectrometry (HPLC-MS), spectrometry, any sequentially coupled mass spectrometry, such as MS-MS or MS-MS-MS, inductively coupled plasma mass spectrometry (ICP-MS), pyrolysis-mass spectrometry (Py-MS), ion mobility mass spectrometry or time of flight (TOF) mass spectrometry, electrospray ionization mass spectrometry (ESI-MS), ESI-MSMS, ESI-MS/(MS)n, matrix assisted laser desorption/ionization time of flight mass spectrometry (MALDI-TOF-MS), surface enhanced laser desorption/ionization time of flight mass spectrometry (SELDI-TOF-MS), desorption/ionization on silicon (DIOS), secondary-ion mass spectrometry (SIMS), quadrupole time-of-flight (Q-TOF), atmospheric pressure chemical ionization mass spectrometry (APCI-MS), APCI-MSIMS, APCI-(MS)n, atmospheric pressure photoionization mass spectrometry (APPI-MS), APPI-MSIMS and APPI-(MS)n, quadrupole mass spectrometry, Fourier transform mass spectrometry (FTMS) and ion trap mass spectrometry, where n is an integer greater than zero. Said techniques are disclosed in, for example, Nissen, Journal of Chromatography A, 703, 1995: 37-57, U.S. Pat. No. 4,540,884 or 5,397,894.

The aforementioned ionization methods generally produce an ion resulting from the addition of one or more atoms or by means of rupture of the molecule. These ions can later be used as substitute markers of the molecule to be measured. As it is used herein, the term "substitute marker" means a biological or clinical parameter that is measured instead of the biologically definitive or clinically more significant parameter.

Ions are typically produced by the addition of a proton or a hydrogen nucleus, [M+H]+ where M means the molecule of interest and H means the hydrogen ion, which is the same as a proton. Some ionization methods will also produce analogous ions. Analogous ions may arise due to the addition of an alkali metal cation, to a greater extent than those produced by the proton discussed above. A typical species can be [M+Na]+ or [M+K]+. The analysis of the ionized molecules is similar regardless of if it has anything to do with a protonated ion, as discussed above, or if it is occupied with an added alkali metal cation. The main difference is that the addition of a proton adds a unit of mass (typically called a Dalton), in the case of the hydrogen ion (i.e., proton), 23 Daltons in the case of sodium or 39 Daltons in the case of potassium. These additional weights or masses are simply added to the molecular weight of the molecule of interest and the MS peak is produced at the point for the molecular weight of the molecule of interest plus the weight of the ion that has been added. These ionization methods can also produce negative ions. The most common molecular signal is the deprotonated molecule [M−H]−, in this case the mass is one Dalton less than the molecular weight of the molecule of interest. Furthermore, multiply charged ions will be produced for some compounds. These have the general type of identification [M+nH]n+, where lowercase n identifies the number of additional protons that have been added.

In a preferred embodiment, the proteomics technique used is mass spectrometry, preferably MALDI-TOF or MALDI-TOF/TOF mass spectrometry.

In another embodiment, gas chromatography combined with mass spectrometry, liquid chromatography combined with mass spectrometry, or MALDI combined with mass spectrometry is used.

In another preferred embodiment, the mass spectrometry is tandem mass spectrometry.

Another possibility for identifying the fraction bound to GAGs is to sequence the peptides or proteins. In the context of the second method of the invention, "protein sequencing" is understood as the determination of the amino acid sequence of a protein. Any protein sequencing method can be used in the method of the invention, for example and without limitation, sequencing by means of the Edman degradation method, sequencing by means of mass spectrometry either directly or after digestion of the peptide fragments, etc. These methods are well known to one skilled in the art.

The precipitate obtained by means of the first method of the invention can also be studied by electron microscopy. To that end, the precipitate is resuspended in a buffer specific for observation by electron microscopy, for example resins such as acrylic Epon resin or Epoxy resin, or 2% glutaraldehyde in 0.1 M cacodylate buffer at pH 7.4. In this case, DMB acts like a contrast agent.

"Electron microscopy" is understood as a technique using an electron microscope, which is a microscope that uses electrons instead of photons or visible light to form the images of objects. The electron microscopy techniques useful in the present invention include both transmission electron microscopy and scanning electron microscopy, among others. This technique allows studying the fractions associated with sulfated GAGs, such as exosomes, for example.

In another aspect, the invention relates to an in vitro identification method (hereinafter "third method of the invention") for identifying the profile of proteins bound to or associated with sulfated GAGs of a sample, which comprises:

a) separating the protein fraction bound to or associated with sulfated GAGs from a sample according to the first method of the invention, and
b) identifying the profile of proteins bound to or associated with sulfated GAGs by means of chromatography or mass spectrometry of the fraction obtained in a). Preferably, the mass spectrometry is tandem mass spectrometry.

The first step of the third method of the invention involves separating the protein fraction bound to or associated with sulfated GAGs from a sample using the first method of the invention.

The precipitate obtained in step a) can be analyzed directly by means of chromatography or mass spectrometry, preferably tandem mass spectrometry. To that end, said precipitate is resuspended in the medium suitable for carrying out the next step of the third method of the invention.

In a preferred embodiment, after step a) the profile of proteins bound to or associated with sulfated GAGs is identified by means of chromatography. "Chromatography" is understood as a method for separating the components of a mixture which is based on differences in the flow behavior of several components of a mixture/solution carried by a mobile phase through a support/column coated with a certain stationary phase. Specifically, some components are strongly bound to the stationary phase and spend more time in the support, whereas other components are predominantly in the mobile phase and go through the support more quickly. The criterion on which the fact that several compounds are separated through the column is based is defined by the particular problem that is being investigated and is imposed by the structure, composition and binding capacity of the stationary phase. For example, a stationary phase could be formed such that linear and low molecular weight molecules elute more quickly than aromatic and high molecular weight molecules do. As the components elute from the support, they can be analyzed immediately by means of a detector or they can be collected for additional analysis. There are a large number of separation methods available today, particularly chromatography methods, including gas chromatography (GC), liquid chromatography (LC), ion chromatography (IC), size exclusion chromatography (SEC), supercritical fluid chromatography (SCF), thin layer chromatography (TLC), high performance liquid chromatography (HPLC), and capillary electrophoresis (CE). Gas chromatography can be used for separating volatile compounds. Liquid chromatography (LC) is a an alternative chromatographic technique useful for separating ions or molecules which are dissolved in a solvent. The principle of separation by GC and LC is the same, the main difference being the phase with which separation is produced (vapor phase vs. liquid phase). Furthermore, GC is used mainly for separating molecules of up to 650 atomic units of weight, while in principle, LC can separate compounds of any molecular weight. The suitable types of liquid chromatography that can be applied in the method of the invention include, without limitation, reversed-phase chromatography, normal-phase chromatography, affinity chromatography, ion exchange chromatography, hydrophilic interaction liquid chromatography (HILIC), size exclusion chromatography, and chiral chromatography. These methods are well known in the art and can readily be applied by one skilled in the art.

In another preferred embodiment, after step a) the profile of proteins bound to or associated with sulfated GAGs is identified by means of mass spectrometry, preferably tandem mass spectrometry.

"Tandem mass spectrometry" is understood as the spectrometry method in which two coupled analyzers are used, such that the first analyzer is used for selecting the compound of interest and then this ion moves on to the collision cell where dissociation of the ion is induced. This technique is a well-known to one skilled in the art and is suitable for quantification and for the screening of samples.

Any embodiment described in the context of the first method of the invention is also applicable to the second and third methods.

Identification Method for Identifying the Profile of Lipids Bound to or Associated with Sulfated GAGs When the fraction bound to or associated with sulfated GAGs precipitated by means of the first method of the invention is a lipid fraction, the precipitate obtained can be used for identifying patterns or profiles of lipids characteristic of a specific condition, whether pathological or not, or of a specific sample.

The analysis of the lipid fraction can be analyzed by various techniques such as, for example, without limitation, lipid electrophoresis, chromatography, or chromatography coupled with mass spectrometry.

In another aspect, the invention relates to an in vitro identification method (hereinafter "fourth method of the invention") for identifying the profile of lipids bound to or associated with sulfated GAGs of a sample, which comprises:
a) separating the lipid fraction bound to or associated with sulfated GAGs from a sample according to the first method of the invention; and
b) identifying the profile of lipids bound to or associated with sulfated GAGs by means of electrophoresis or chromatography of the fraction obtained in a).

In the context of the fourth method of the invention, the term "lipids" refers to any organic molecule mainly made up of carbon and hydrogen and, to a lesser extent, oxygen, although it can also contain phosphorus, sulfur, and nitrogen, which are hydrophobic and soluble in organic solvents such as benzine, benzene, and chloroform. The term "lipids" includes any type of lipids such as, without limitation, triglycerides, phospholipids, steroid hormones, etc. Any lipid bound to or otherwise associated with GAG can be identified by means of the fourth method of the invention.

In the context of the fourth method of the invention, "profile of lipids" is understood as the specific pattern of lipids formed by the fraction bound to or associated with GAGs. The profile of lipids can be qualitative, quantitative, or both. In this document, the profile of lipids refers not only to the set of lipids of a known nature that have been identified specifically (specific profile), but rather it also refers to the pattern obtained after electrophoretic separation, although it is not possible to relate each band with a specific lipid (unspecific profile).

The fourth method of the invention consists of a first step in which the lipid fraction bound to or associated with sulfated GAGs of a sample is separated according to the first method of the invention.

The precipitate obtained in the first step can be identified by means of electrophoresis or chromatography.

In a preferred embodiment, the profile of lipids is identified by means of lipid electrophoresis. The term "electrophoretic separation" or "electrophoresis" has been defined in relation to the second and third methods of the invention, and in the context of the fourth method of the invention it refers to lipid electrophoresis.

In another preferred embodiment, the profile of lipids is identified by means of chromatography. The term "chromatography" has been defined in relation to the second and third methods of the invention, and in the context of the fourth method of the invention it refers to lipid chromatography.

The remaining terms have been defined in the context of the preceding aspects. Any embodiment described for the first, second, and third methods of the invention is also applicable to the fourth method of the invention.

Methods for Detecting Alterations in the Pattern of Glycosylation by Sulfated GAGs The method of the invention is also useful for detecting alterations in the pattern of glycosylation by sulfated GAGs of lipids or proteins.

In another aspect, the invention relates to an in vitro method (hereinafter "fifth method of the invention") for detecting an alteration in the pattern of glycosylation by sulfated GAGs of a sample, which comprises:
a) identifying the profile of proteins bound to or associated with sulfated GAGs of a sample according to the second or third method of the invention and/or identifying the profile of lipids bound to or associated with sulfated GAGs of a sample according to the fourth method of the invention; and
b) comparing the profile of proteins bound to or associated with sulfated GAGs obtained in a) with the profile obtained for a reference sample and/or comparing the profile of lipids bound to or associated with sulfated GAGs obtained in a) with the profile obtained for a reference sample, wherein a difference in the profile obtained in a) with respect to the profile obtained in the reference sample indicates an alteration in the pattern of glycosylation by sulfated GAGs.

In the context of the fifth method of the invention, "pattern of glycosylation" is understood as the specific pattern of glycosylation by sulfated GAGs of the components of a sample, where a sulfated GAG is added to another molecule, particularly to a protein or lipid.

In the context of the fifth method of the invention, "alteration in the pattern of glycosylation" is understood as any difference in the pattern of glycosylation with respect to a reference sample, whether it is an increase or a decrease in glycosylation by sulfated GAGs.

In the first step of the fifth method of the invention, the profile of proteins bound to or associated with sulfated GAGs of a sample is identified by means of the second or third method of the invention, and/or the profile of lipids bound to or associated with sulfated GAGs of a sample is identified by means of the fourth method of the invention, as described above.

The second step of the fifth method of the invention consists of comparing the profile of proteins bound to or associated with sulfated GAGs obtained in a) with the profile obtained for a reference sample, and/or comparing the profile of lipids bound to or associated with sulfated GAGs obtained in a) with the profile obtained for a reference sample, wherein a difference in the profile obtained in a) with respect to the profile obtained in the reference sample indicates an alteration in the pattern of glycosylation by sulfated GAGs.

In the context of the fifth method of the invention, "reference sample" is understood as a sample of the same type as the sample that is going to be analyzed used as the basis for comparison. In a preferred embodiment, the reference sample comes from healthy normal individuals who are not affected by any disease. The reference sample can also be obtained from the same subject to be analyzed. In a preferred embodiment of the invention, the reference sample was obtained from healthy individuals of the same age and sex as the sample to be analyzed.

The pattern of glycosylation of the sample to be analyzed is compared with the pattern of glycosylation of the reference sample, and this allows the detection of quantitative and/or qualitative alterations in this pattern.

The remaining terms have been defined in the context of the preceding aspects. Any embodiment described for the first, second, third, and fourth methods of the invention is also applicable to the fifth method of the invention.

Uses of the Methods of the Invention

The methods of the invention, which allow analyzing the fraction bound to or associated with GAG, have different applications in biomedicine. In that sense, without limitation, they can be used for the identification of new biomarkers or profiles of biomarkers on a protein level which function as prognostic or diagnostic indicators, or for the follow-up of a specific pathology or condition. Likewise, they allow monitoring a therapy and designing a personalized therapy in a subject suffering from a disease, or selecting a patient susceptible to being treated with a specific therapy. It can also be useful for the discovery of new therapeutic targets. Another application is the use thereof in the study of new cell communication pathways or molecular mechanisms.

Therefore, in another aspect the invention relates to the use of the second, third, fourth, and fifth methods of the invention for identifying protein or lipid biomarkers bound to or associated with sulfated GAGs.

As they are used herein, the terms "biomarker" or "marker biological" refer to a substance used as an indicator of a biological condition, which has to be able to be measured objectively and be evaluated as an indicator of a normal biological process, a pathogenic condition, or of a response to a pharmacological treatment.

In one embodiment, said biomarkers are useful for the diagnosis, prognosis, and/or monitoring the progression of a disease.

In another embodiment, said biomarkers are useful for monitoring the effect of a therapy for the treatment of a disease.

In another embodiment, said biomarkers are useful for predicting the response to a therapy.

"Predicting the response to a therapy" is understood as the possibility of knowing prior to the administration of a therapy if an individual will respond well or poorly to said therapy.

In another embodiment, said biomarkers are useful for designing a personalized therapy.

In another embodiment, said biomarkers are useful for identifying compounds suitable for the treatment of a disease.

In a preferred embodiment, the disease is selected from the group consisting of a kidney disease and mucopolysaccharidosis. In another more preferred embodiment, the kidney disease is autosomal dominant polycystic kidney disease type 1 or type 2.

The terms "diagnosis", "prognosis", "monitoring the progression", "monitoring the effect of a therapy", "designing a personalized therapy", and "identification of compounds suitable for the treatment" are explained below.

Diagnostic Methods of the Invention

The authors of the present invention have identified a series of markers present in the urine of subjects suffering from mucopolysaccharidosis and kidney disease, and which markers are absent or present in a different proportion in individuals not suffering from such diseases. These markers can be used in a rapid diagnostic method for diagnosing mucopolysaccharidosis in newborns, in early diagnostic methods for diagnosing kidney disease, or in diagnostic methods for diagnosing advanced kidney disease.

In one aspect, the invention relates to an in vitro method for diagnosing a disease associated with an alteration of one or more sulfated GAGs in a subject, which comprises:

a) separating the free sulfated GAGs and the fraction bound to or associated with sulfated GAGs from a biological sample from said subject by means of the first method of the invention, b) detecting the level of one or more sulfated GAGs separated in a), and c) comparing said level with a reference value for said one or more sulfated GAGs, wherein an increased or decreased level of one or more sulfated GAGs with respect to the reference value is indicative of the subject suffering from a disease associated with an alteration of one or more sulfated GAGs.

In the context of the present invention, "in vitro method for diagnosing a disease associated with an alteration of one or more sulfated GAGs" is understood as a method which allows showing the existence of any disease in which a pathogenic alteration of the levels of sulfated GAGs is produced, i.e., when said process is harmful or not desired in a subject, by means of the detection of these levels. "Diagnosing" refers to evaluating the probability according to which a subject suffers from a disease.

The methods are carried out "in vitro", i.e., they are not carried out to practice on a human or animal body.

As those skilled in the art will understand, such an evaluation, may not be correct for 100% of the subjects to be diagnosed, even though it preferably is correct for 100% of them. The term, however, requires being able to identify a statistically significant part of subjects as suffering from the disease. One skilled in the art can readily determine if a part is statistically significant using several well-known statistical evaluation tools, for example, determination of confidence intervals, determination of the p-value, Student's t-test, Mann-Whitney test, etc. Preferred confidence intervals are at least 50%, at least 60%, at least 70%, at least 80%, at least 90%, at least 95%. The p-values are preferably 0.2, 0.1, 0.05.

"Disease associated with an alteration of one or more sulfated GAGs" is understood as any disease occurring with an increase or with a decrease in the levels of sulfated GAGs with respect to the levels of a normal individual. Diseases in which there is an alteration in one or more glycosaminoglycans in a primary or secondary manner are, without limitation, mucopolysaccharidosis, renal amyloidosis (Tencer J. et al. Nephrol Dial Transplant. 1997. 12(6):1161-6), glomerulonephritis (Tencer J. et al. Clin Nephrol. 1997; 48(4):212-9), congenital nephrotic syndrome (Vermylen C. et al. Pediatr Nephrol. 1989; 3(2):122-9), Balkan endemic nephropathy (Jurétic D. et al. Nephron. 1993; 65(4):564-7), kidney transplant (Rodriguez-Cuartero et al. Clin Nephrol. 1997; 47(4):274-6), kidney stone disease (Hesse et al., Urol. Int. 1986; 41(2):81-7), diabetic nephropathy (Pérez Blanco et al. Nephron. 1996; 73(2):344-5), hypothyroidism (Tokoro T. and Eto Y. Eur J Pediatr. 1985 May; 144(1):84-6), diabetes (Nikiforovskaia L F, and Ivanova L N. Vopr Med Khim. 1987; 33(1):91-6), rheumatoid arthritis ((Kéry V. et al. Clin Chem. 1992; 38(6):841-6), and syringomyelia (Elaev N. R. and Bakhtiarova K Z. Biull Eksp Biol Med. 1992; 114(9):271-2).

In a preferred embodiment, the disease associated with an alteration of one or more sulfated GAGs is selected from the group consisting of:

a) a mucopolysaccharidosis selected from the group consisting of Hurler syndrome (deficiency of alpha-L-iduronidase), Scheie syndrome (deficiency of alpha-L-iduronidase), Hunter syndrome (deficiency of iduronate-2-sulfatase), Sanfilippo syndrome A (deficiency of heparan sulfamidase), Sanfilippo syndrome B (deficiency of alpha-N-acetyl-glucosaminidase), Sanfilippo syndrome C (deficiency of heparan-alpha-glucosaminide N-acetyltransferase), Sanfilippo syndrome D (deficiency of N-acetylglucosamine-6-sulfatase), Morquio syndrome A (deficiency of N-acetylgalactosamine-6-sulfatase), Morquio syndrome B (deficiency of beta-D-galactosidase), Maroteaux-Lamy syndrome (deficiency of arylsulfatase B), and Sly syndrome (deficiency of beta-glucuronidase);

b) a kidney disease selected from the group consisting of autosomal dominant polycystic kidney disease type 1 or type 2, glomerulonephritis, nephrotic syndrome, Balkan endemic nephropathy, kidney transplant, kidney stone disease, and diabetic nephropathy;

c) an endocrinopathy selected from the group consisting of hypothyroidism, and diabetes;

d) a rheumatic disorder selected from the group consisting of osteoarthritis, ankylosing spondylitis, rheumatoid arthritis, and syringomyelia; and e) an oncological disease.

In one embodiment, the oncological disease is selected from prostate cancer and colon cancer.

In an even more preferred embodiment, the disease is selected from the group consisting of mucopolysaccharidosis and kidney disease.

As it is used herein, the term "mucopolysaccharidosis" or "MPS" designates a heterogeneous group of innate metabolism errors caused by the deficiency of any of the enzymes necessary for the degradation of GAGs, i.e., they are congenital alterations in glycosylation. Non-degraded GAGs are usually partially excreted in the urine, but the rest are accumulated in the lysosomes. This accumulation causes cellular alterations and interferences in other metabolic processes with serious consequences for the human body, leading to cell, tissue and organ damage. For example, accumulation in the brain is responsible for mental retardation and psychomotor retardation, and the accumulation of these substances in other tissues in general offers a wide variety of findings and forms ranging from phenotypically mild and hardly perceptible signs to unique and distorted shapes that considerably affect individuals suffering from said alteration. Seven types of mucopolysaccharidosis with several subtypes involving 11 specific enzymes have been described up until now. Table I describes the different types of MPS and the type of GAG that is excreted.

TABLE I

Types of MPS and GAG excreted.

| Type of MPS | Other names | Type of GAG excreted |
| --- | --- | --- |
| MPS I | Hurler, Hurler-Scheie, Scheie | DS, HS |
| MPS II | Hunter | DS, HS |
| MPS III | Sanfilippo types A-D | HS |
| MPS IV | Morquio types A and B | A: KS, CS |
|  |  | B: KS |
| MPS VI | Maroteaux-Lamy | DS |
| MPS VII | Sly | DS, HS, CS |
| MPS IX | Deficiency of hyaluronidase | Unknown |

DS: dermatan sulfate;
HS: heparan sulfate;
CS: chondroitin-4 and -6 sulfate;
KS: keratan sulfate.

All types of MPS are inherited in an autosomal recessive manner, with the exception of Hunter syndrome (MPS II), which is X chromosome-linked.

The term "kidney disease" refers to a condition characterized by a significant and progressive decrease in kidney function, expressed by an estimated glomerular filtration or creatinine clearance <60 ml/min/1.73 m² or as the presence of persistent kidney damage for at least 3 months. The kidney damage is usually diagnosed by means of markers instead of by a renal biopsy, so the diagnosis thereof may be performed without knowing the cause. In a preferred embodiment, the kidney disease is autosomal dominant polycystic kidney disease type 1 or type 2. The term "autosomal dominant polycystic kidney disease type 1 or type 2" or "ADPKD1 or ADPKD2" refers to a progressive genetic disease of the kidneys characterized by the presence of multiple cysts in both kidneys. This disease can also damage the liver, seminal vesicles, pancreas, arachnoids, and, rarely, the heart and the brain. Manifestations of this disease include abnormalities in kidney function, hypertension, renal pain, and kidney failure. The initial symptoms are hypertension, fatigue, severe pains in the back and sides, and urinary tract infections. The disease often leads to the development of chronic kidney failure and may result in the complete loss of kidney function, which requires a certain type of dialysis. In 85% of patients, this disease is caused by mutation of the PKD1 gene (locus 16p13.3-p13.1), and in the remaining 15% the cause is mutation of the PKD2 gene (locus 4q21q23).

In one embodiment, the alteration of one or more sulfated GAGs is an increase in one or more GAGs. In one embodiment, the disease associated with an increase in one or more sulfated GAGs is a disease occurring with an undesired accumulation of one or more sulfated GAGs selected from mucopolysaccharidosis, mucolipidosis, congenital nephrotic syndrome, Balkan endemic nephropathy, rheumatoid arthritis, and syringomyelia.

In another embodiment, the alteration of one or more sulfated GAGs is a decrease in one or more GAGs. In one embodiment, the disease associated with a decrease in one or more sulfated GAGs is selected from the group consisting of renal amyloidosis, glomerulonephritis, nephrotic syndrome, hypothyroidism, and diabetes.

The first step of the diagnostic method of the invention comprises separating the free sulfated GAGs and the fraction bound to or associated with sulfated GAGs from a biological sample from a subject by means of the first method of the invention.

The term "biological sample" has been defined in the context of the first method of the invention. In a preferred embodiment, the biological sample is a urine, serum, or plasma sample. In another preferred embodiment, the biological sample is a sample of exosomes, preferably exosomes isolated from a urine sample.

In the present invention, "subject" is understood as any animal classified as a mammal and includes, but is not limited to, pets or farm animals, primates and humans, for example, human beings, non-human primates, cows, horses, pigs, sheep, goats, dogs, cats, or rodents. Preferably, the subject is a male or female human being of any race or age. In the context of this aspect of the invention, the subject is a subject potentially suffering from a disease associated with an alteration of one or more sulfated GAGs.

The second step of the diagnostic method comprises detecting the level of one or more sulfated GAGs separated in a).

The levels of GAGs can be detected by means of methods described in the state of the art and known to one skilled in the art. Said methods include colorimetric methods of spectrophotometric detection; specific GAG assay methods which allow identifying the types of GAGs that are produced or excreted in excess, such as HPLC, ELISA, and tandem mass spectrometry; and methods based on GAG depolymerization (Tomatsu S. et al. 2013. Mol. Genet. Metab. 110(0):42-53).

In a preferred embodiment, step (b) is performed by means of staining sulfated GAGs with the DMB dye. Preferably, staining is performed by means of 0.02% DMB in water. The gel must then be destained, preferably using 10% acetic acid.

One skilled in the art will see that the method of the invention can be put into practice using both the absolute level and the relative level of sulfated GAGs. Therefore, in the present invention, the expression "level of one or more sulfated GAGs" is used to refer to both the absolute levels and the relative levels of sulfated GAGs.

The expression "absolute levels" refers to the total amount of sulfated GAGs in a sample. Said value can be determined as the concentration of sulfated GAGs expressed in units of mass per unit of volume (for example, in ng/ml of sample), in number of molecules of sulfated GAGs per unit of volume (for example, in pmol of sulfated GAGs/ml of sample), in units of mass of sulfated GAGs per unit of mass of total GAGs (pg sulfated GAGs/mg total GAGs), or in number of molecules of sulfated GAGs per unit of mass of total GAGs (for example, in pmol sulfated GAGs/mg total GAGs).

The expression "relative levels" refers to the relationship between the levels of sulfated GAGs and of a reference GAG, i.e., it is defined as the concentration of sulfated GAGs in normalized form with respect to said reference GAG.

For the purpose of normalizing the values of sulfated GAGs between the different samples, it is possible to compare the levels of sulfated GAGs in the samples to be analyzed with the expression of a control GAG. "Control GAG" is understood herein as a GAG the concentration of which does not change or only changes in limited amounts in sick cells with respect to normal cells. Preferably, the control GAG is chondroitin sulfate.

The skilled person will see that the level of total sulfated GAGs or the level of free sulfated GAGs or the level of sulfated GAGs associated with a protein or lipid fraction can be detected in step b). In a preferred embodiment, the level of one or more free sulfated GAGs is detected.

Once the level of one or more sulfated GAGs in a sample has been determined, step (c) of the method of the invention is carried out, which consists of comparing the levels of sulfated GAGs obtained in step (b) with a reference value for each sulfated GAG.

The "reference value" comes from a set of samples preferably consisting of a mixture of the same type of sample to be analyzed from normal individuals not affected by diseases of this type. Said reference value can be determined by means of techniques that are well known in the state of the art, such as, for example, determination of the mean value of sulfated GAGs measured in samples from healthy subjects. The reference value can also be obtained from the same subject to be analyzed. In a preferred embodiment of the invention, the reference value was obtained from samples from healthy individuals of the same age and sex as the subject.

Once the reference value is established, the value of the levels of sulfated GAGs obtained in step (a) can be compared with this reference value, and therefore it allows detection of alterations in the levels of sulfated GAGs of the subject with respect to the reference value. In the method of the invention, an increased or decreased level of one or more sulfated GAGs with respect to the reference value is indicative of the subject suffering from a disease associated with an alteration of one or more sulfated GAGs. More specifically, in the method of the invention an increase in the levels of sulfated GAGs with respect to the reference value is indicative of the subject suffering from a disease associated with an increase in the levels of sulfated GAGs.

In the context of the present invention, "increase in the levels" or "increased level" with respect to the reference value is understood as a variation of the levels above the reference value of at least 5%, at least 10%, at least 15%, at least 200, at least 250, at least 300, at least 350, at least 40%, at least 45%, at least 50%, at least 55%, at least 60%, at least 650, at least 700, at least 750, at least 800, at least 850, at least 900, at least 950, at least 1000, at least 1100, at least 1200, at least 1300, at least 1400, at least 1500, or more, in comparison with the reference value.

In a preferred embodiment, the disease is mucopolysaccharidosis, and:
(i) an increased level of free dermatan sulfate with respect to the reference value is indicative of the subject suffering from mucopolysaccharidosis type I, type II, type VI, or type VII;
(ii) an increased level of free heparan sulfate with respect to the reference value is indicative of the subject suffering from mucopolysaccharidosis type III; and
(iii) an increased level of free keratan sulfate with respect to the reference value is indicative of the subject suffering from mucopolysaccharidosis type IV.

On the other hand, in the method of the invention a decrease in the levels of sulfated GAGs with respect to the reference value is indicative of the subject suffering from a disease associated with a decrease in the levels of sulfated GAGs.

Similarly, "decrease in the levels" or "decreased level" with respect to the reference value is understood as a variation of the levels below the reference value of at least 50, at least 100, at least 150, at least 200, at least 250, at least 300, at least 350, at least 400, at least 450, at least 50%, at least 55%, at least 60%, at least 65%, at least 70%, at least 750, at least 800, at least 850, at least 900, at least 950, or by at least 1000 (i.e., absent) in comparison with the reference value.

In one embodiment, an electrophoretic separation of the sample is performed after step (a). Said electrophoretic separation can be carried out in any type of gel including, without limitation, agarose gel, polyacrylamide gel, and cellulose acetate gel. In a preferred embodiment, the gel is a cellulose acetate gel. In an even more preferred embodiment, the electrophoresis buffer is barium acetate.

Therefore, a preferred embodiment of the invention is an in vitro method for diagnosing mucopolysaccharidosis in a subject, which comprises:
a) separating the free sulfated GAGs from a urine sample from said subject by means of the first method of the invention,
b) subjecting the precipitate obtained in the preceding step to electrophoresis, preferably in cellulose acetate gel,
c) detecting the level of one or more free sulfated GAGs separated in b) by means of staining with DMB dye, and
d) comparing said level with a reference value for said one or more free sulfated GAGs,
wherein an increased level of free dermatan sulfate with respect to the reference value is indicative of the subject suffering from mucopolysaccharidosis type I, type II, type VI or, type VII;
wherein an increased level of free heparan sulfate with respect to the reference value is indicative of the subject suffering from mucopolysaccharidosis type III; and wherein an increased level of free keratan sulfate with respect to the reference value is indicative of the subject suffering from mucopolysaccharidosis type IV.

The inventors have found that the signal peptide of uromodulin is present in the urine samples from a subject suffering from mucopolysaccharidosis and absent in healthy subjects.

Therefore, in another aspect the invention relates to an in vitro method for diagnosing mucopolysaccharidosis in a subject which comprises detecting, in a urine sample from said subject, the presence of the signal peptide SEQ ID NO: 1 of uromodulin or of a variant thereof.

In a preferred embodiment, the method comprises:
a) detecting the level of the signal peptide SEQ ID NO: 1 of uromodulin or of a variant thereof in a urine sample from said subject, and
b) comparing said level with a reference value, wherein an increased level of the signal peptide SEQ ID NO: 1 of uromodulin or of a variant thereof with respect to the reference value is indicative of the subject suffering from mucopolysaccharidosis.

It will be understood that the urine sample can be analyzed as such, or, alternatively, the uromodulin bound to sulfated GAGs can first be extracted from the sample before the analysis by means of any of the separation methods for separating GAGs described in the state of the art. In a preferred embodiment, the separation method for separating GAGs is the first method of the invention, and then the sulfated GAG-bound fraction that has precipitated is analyzed.

In the case of urine samples coming from patients with kidney disease, the method of the invention has given rise to the discovery of profiles of biomarkers on a GAG-bound protein level which function as diagnostic indicators of kidney disease.

In another aspect, the invention relates to an in vitro method for diagnosing a kidney disease in a subject which comprises detecting the level of uromodulin or of a variant thereof bound to or associated with sulfated GAGs and/or detecting the level of albumin or of a variant thereof bound to or associated with sulfated GAGs in a urine sample from said subject, and comparing said level with a reference value, wherein a decreased level of uromodulin or of a variant thereof bound to or associated with sulfated GAGs with respect to the reference value and/or a decreased level of albumin or of a variant thereof bound to or associated with sulfated GAGs with respect to the reference value is indicative of the subject suffering from a kidney disease.

In the intensive search for new exosome-associated kidney biomarkers, it is common to perform uromodulin depletion strategies or to use uromodulin exclusion lists on a bioinformatics level. However, the inventors have discovered a complex formed by uromodulin, sulfated GAGs, and exosomes. These complexes can be monitored in an easy and inexpensive manner in urine for use as diagnostic and prognostic biomarkers for a kidney disease given the identification of their characteristic expression profile.

In another aspect, the invention relates to an in vitro method for diagnosing an advanced kidney disease in a subject which comprises detecting the level of uromodulin- or uromodulin variant-sulfated GAG-exosomes complexes in a urine sample from said subject, and comparing said level with a reference value, wherein a decreased level of uromodulin- or uromodulin variant-sulfated GAG-exosomes complexes with respect to the reference value is indicative of the subject suffering from an advanced kidney disease.

In a preferred embodiment, the separation of uromodulin and/or albumin bound to or associated with sulfated GAGs and the separation of the uromodulin- or uromodulin variant-sulfated GAG-exosomes complexes from the urine sample is performed according to the first method of the invention.

As it is used herein, the term "signal peptide" refers to a peptide formed by 24 amino acids of sequence SEQ ID NO: 1 which are the first that appear when the polypeptide chain of uromodulin is synthesized and they decide on the uromodulin destination, transport pathway, and secretion efficiency. In one embodiment of the invention, the peptide formed by 30 amino acids of SEQ ID NO: 2 is detected.

As it is used herein, the term "uromodulin" refers to a glycoprotein which is secreted into the urine after proteolytic cleavage, where it contributes to osmotic pressure by preventing urinary tract infection and modulating the formation of crystals. It is the most abundant protein present in urine. It is also referred to as Tamm-Horsfall glycoprotein (THP). It is specifically expressed in the loop of Henle in the kidney and is related to different kidney pathologies. In humans it is encoded by the UMOD gene (UniGene Hs. 654425). Human uromodulin is the protein defined by the Uniprot database sequence with accession number P07911 of 22 Jul. 2015. Sequence P07911 corresponds to the uromodulin precursor, the signal peptide of which occupies positions 1 to 24, and the propeptide of which (positions 615 to 640) is removed in mature form. Mature uromodulin is thereby formed by amino acids 25 to 614; whereas the secreted form is formed by amino acids 25 to 587 of sequence P07911.

As it is used herein, the term "albumin" refers to an member of the albumin protein family, which proteins are globular proteins that are soluble in water, moderately soluble in concentrated saline solutions, and undergo heat denaturation. Albumins are normally found in blood plasma. Serum albumin is produced by the liver, dissolves in blood plasma and is the most abundant blood protein in mammals. In some renal pathologies, albumin is lost through urine. Particularly, the term "albumin" refers to a globular protein which is encoded in humans by the ALB gene (UniGene Hs. 418167). Human serum albumin is the protein defined by the Uniprot database sequence with accession number P02768 of 22 Jul. 2015.

Figure 7:
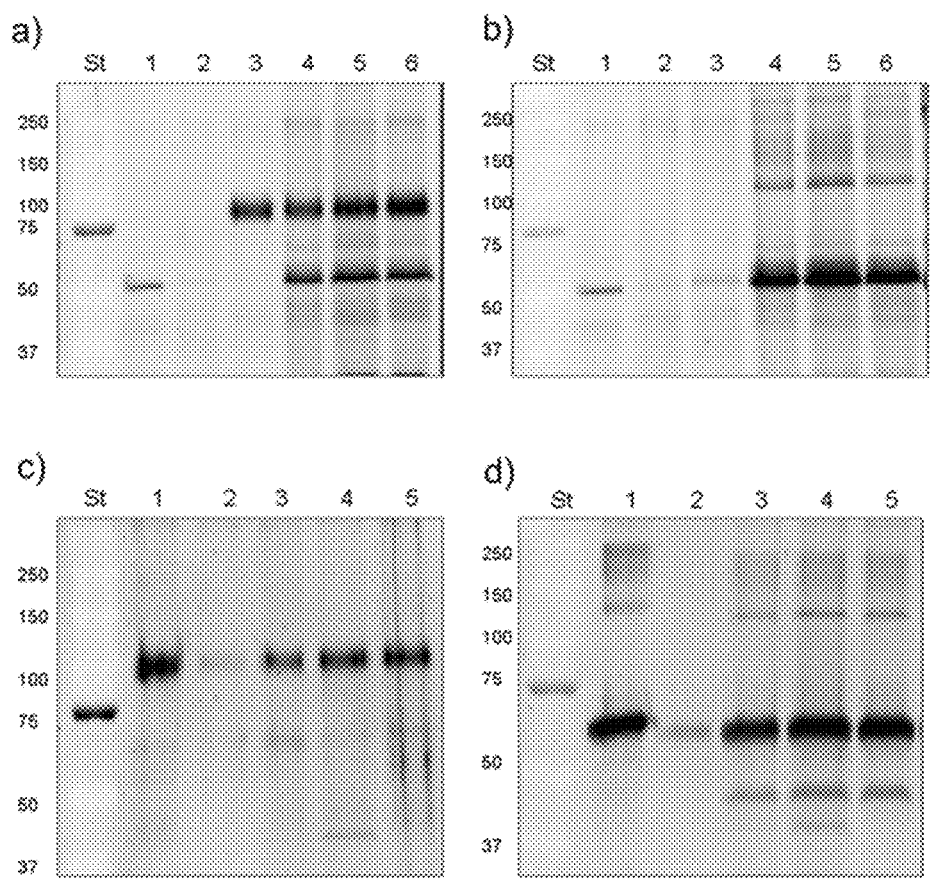
FIG. 7: Binding of commercial uromodulin and/or albumin with commercial GAGs (heparan, chondroitin, and dermatan sulfate) in PBS (c and d) or uromodulin-free urine (a and b) of a patient with a truncating mutation in the uromodulin gene. a) Lane 1, unprecipitated urine; Lane 2, urine precipitated with DMB; Lane 3, urine with added commercial uromodulin and precipitated with DMB; Lanes 4, 5 and 6, urine with added commercial uromodulin, incubated with heparan, chondroitin, and dermatan sulfate, respectively, and precipitated with DMB; b) Lane 1, unprecipitated urine; Lane 2, urine precipitated with DMB; Lane 3, urine with added commercial albumin and precipitated with DMB; Lanes 4, 5, and 6, urine with added commercial albumin, incubated with heparan, chondroitin, and dermatan sulfate, respectively, and precipitated with DMB; c) Lane 1, commercial unprecipitated uromodulin; Lane 2, commercial uromodulin precipitated with DMB; Lanes 3, 4, and 5, commercial uromodulin incubated in PBS with heparan, chondroitin, or dermatan sulfate, respectively, and precipitated with DMB; d) Lane 1, commercial unprecipitated albumin; Lane 2, commercial albumin precipitated with DMB; Lanes 3, 4, and 5, commercial albumin incubated in PBS with heparan, chondroitin, and dermatan sulfate, respectively, and precipitated with DMB; St, molecular weight marker.

The term "uromodulin- or uromodulin variant-sulfated GAG-exosomes complexes" refers to a complex formed by the association of at least three components: the protein uromodulin, sulfated GAGs, and exosomes. Those complexes where the uromodulin has been replaced with a uromodulin variant are also included in the present invention. These three components can be found bound to or associated with one another in many different ways (see FIG. 15), but this binding or association is specific, i.e., it goes beyond simple mechanical interactions due to proximity or abundance, as demonstrated by the assays reflected in FIGS. 7, 10 and 12.

As it is used herein, the term "protein" also includes all the physiologically relevant forms of chemical modification after translation. Post-translational modifications falling within the scope of the present invention include, for example, cleavage of the signal peptide, glycosylation, acetylation, phosphorylation, isoprenylation, proteolysis, myristoylation, protein folding, and proteolytic process, etc. Furthermore, the proteins can include non-natural amino acids formed by modifications after translation, or by means of introducing non-natural amino acids during translation. For the diagnostic method of the invention, the detected protein is the one that corresponds to the species to which the subject from which the sample to be analyzed has been taken belongs.

The "protein variants" can also be used to measure the levels of protein in the methods of the invention. The protein variants can be: (i) those in which one or more of the amino acid residues are replaced with a conserved or non-conserved amino acid residue (preferably a conserved amino acid), and such replaced amino acid residue may or may not be encoded by the genetic code, (ii) those in which there is one or more modified amino acid residues, for example, residues which are modified by the coupling of substituent groups, (iii) those in which the protein is an alternative splicing variant of the protein, and/or (iv) the protein fragments. The fragments include proteins generated through the proteolytic process (including proteolysis at multiple sites) of an original sequence. Said variants fall within the scope of the present invention.

The variants according to the present invention include amino acids sequences having at least 60%, 70%, 80%, 90%, 95%, or 96% similarity or identity with respect to the original amino acid sequence. As is known, "similarity" between two proteins is determined by means of comparing the amino acid sequence of one protein with a sequence of a second protein. The degree of "identity" between two proteins is determined using computer algorithms and methods which are well known to one skilled in the art, preferably using the BLASTP algorithm [BLASTManual, Altschul, S., et al., NCBI NLM NIH Bethesda, Md. 20894, Altschul, S., et al., J. Mol. Biol., 215:403-410 (1990)].

In a particular embodiment, the variant is a mammal variant, preferably a human variant, more preferably with at least 60%, 70%, 80%, 90%, 95%, or 96% similarity or identity with respect to the original amino acid sequence.

The expression levels of a protein or peptide can be detected and quantified by means of conventional methods. Said methods include, without limitation, detection of the protein by measuring its affinity for one of its ligands, and subsequent quantification of the protein-ligand complex, or by means of using antibodies with the capacity to bind specifically to the protein (or fragments thereof containing the antigenic determinants) and subsequent quantification of the resulting antigen-antibody complexes. In a preferred embodiment, detection is carried out by means of an antibody that binds specifically to the protein or by means of a fragment thereof with the capacity to bind to the antigen. In another embodiment, detection is carried out by means of an aptamer that binds specifically to the protein or by means of a fragment thereof with the capacity to bind to said protein. In another embodiment, detection is carried out by means of an enzyme capable of specifically recognizing an amino acid sequence of the protein and cleaving it.

The antibodies that can be used in these assays are, for example, serum polyclonal antibodies; hybridoma supernatants or monoclonal antibodies, chimeric antibodies, humanized antibodies, primatized antibodies, human antibodies, bispecific antibodies, and antibody fragments such as Fab, Fab', F(ab')2, scFv, diabodies, triabodies, tetrabodies, and nanobodies. Furthermore, the antibodies used in the method of the invention may or may not be labeled with a detectable agent. In a particular embodiment, the antibody used is conjugated with a detectable agent.

In the context of the present invention, the terms "detectable agent" and "label" are synonymous and refer to an agent of such a nature that allows detection by means of enzymatic, radioactive, or fluorescence methods. The detectable compound can be an enzyme, a radioactively labeled compound or a radioactive isotope, a fluorochrome, a chemoluminescent reagent, an enzyme substrate or cofactor, an enzyme inhibitor, a particle, a dye, etc.

Compounds that are radioactively labeled by means of radioactive isotopes, also called radioisotopes or radionuclides, may include, without limitation, $^{3}H$, $^{14}C$, $^{15}N$, $^{35}S$, $^{90}Y$, $^{99}Tc$, $^{111}In$, $^{125}I$, $^{131}I$. The fluorescent markers may include, without limitation, rhodamine, lanthanide phosphors, or FITC. The enzyme markers may include, without limitation, horseradish peroxidase, beta-galactosidase, luciferase, or alkaline phosphatase. The preferred labels include, but are not limited to, fluorescein, a phosphatase such as alkaline phosphatase, biotin, avidin, a peroxidase such as horseradish peroxidase, and biotin-related compounds or avidin-related compounds (for example, streptavidin or ImmunoPure® NeutrAvidin available from Pierce, Rockford, Ill.).

There is wide variety well-known assays that can be used in the present invention, in which unlabeled primary antibodies and labeled secondary antibodies are used: such techniques include Western blot or Western transference, ELISA (enzyme-linked immunosorbent assay), RIA (radioimmunoassay), competitive EIA (competitive enzyme immunoassay), DAS-ELISA (double antibody sandwich ELISA), or techniques based on the use of biochips or protein microarrays that include specific antibodies or assays based on colloidal precipitation in forms such as test strips. Other forms for detection of proteins include techniques such as affinity chromatography, ligand binding assays, etc. There are commercial antibodies specific for the proteins of the invention on the market that can be used in the context of the invention.

In a particular embodiment, quantification of the levels of protein is performed by Western blot or ELISA.

In another preferred embodiment, detection is performed by means of mass spectrometry, preferably tandem mass spectrometry, which has been defined above.

One skilled in the art will see that the method of the invention can be put into practice using both the absolute and the relative expression level of the protein. Therefore, in the present invention, the expression "levels of the protein" is used to refer to both absolute levels and to relative levels of said protein.

The expression "absolute values" refers to the total amount of the protein of interest in a sample. Said value can be determined as the concentration of protein expressed in units of mass per unit of volume (for example, in ng/ml of sample), in number of molecules of protein per unit of volume (for example, in pmol of protein/ml of sample), in units of mass of protein X per unit of mass of total protein (pg protein X/mg total protein), or in number of molecules of protein X per unit of mass of total protein (for example, in pmol protein X/mg of total protein).

The expression "relative levels" refers to the relationship between the expression levels of the protein object of study and of a reference protein, i.e., it is defined as the concentration of protein object of study in normalized form with respect to said reference protein.

For the purpose of normalizing the values of protein between the different samples, it is possible to compare the levels of the protein under study in the samples to be analyzed with the expression of a control protein. "Control protein" is understood herein as a protein the expression of which does not change or only changes in limited amounts in altered cells with respect to non-altered cells. Preferably, the control protein is a protein encoded by genes that are constitutively expressed, which are those genes that are always active or constantly transcribed, such that these proteins are constitutively expressed and carry out essential cell functions. The preferred control proteins that can be used in the present invention include, without limitation, β-2-microglobulin (B2M), ubiquitin, 18S ribosomal protein, cyclophilin, GAPDH, PSMB4, tubulin, and actin. In a more preferred embodiment, the control protein is tubulin.

One skilled in the art understands that mutations in the amino acid sequence of the protein under study do not affect the detection of the expression of said protein, and therefore the variants of this protein generated by mutations of the amino acid sequence fall within the scope of the present invention.

Once the expression level of the protein in a sample has been determined, step (b) of the invention is carried out, which consists of comparing the levels of the protein under study obtained in step (a) with a reference value.

As it is used herein, the term "reference value" refers to predetermined criteria used as a reference to evaluate the values or data obtained from the samples collected from a subject. The reference value or reference level can be an absolute value, a relative value, a value having an upper or lower limit, a range of values, a mean value, a median value, an average value, or a value compared with a particular control or basal value. A reference value may be based on a value of an individual sample, such as, for example, a value obtained for a sample from the subject being analyzed, but at an earlier moment in time. The reference value may be based on a large number of samples, such as a population of subjects of the coinciding chronological age group, or may be based on a set of samples which include or exclude the sample being analyzed. Generally, the reference value comes from a set of samples preferably consisting of a mixture of the same type of sample to be analyzed from normal individuals not affected by the disease. Said reference value can be determined by means of techniques that are well known in the state of the art, such as, for example, determination of the mean value of the protein measured in a sample obtained from healthy subjects. The reference value may also be obtained from constitutively expressed proteins taken from the same subject to be analyzed.

Once the reference value is established, the value of the levels of protein obtained in step (a) can be compared with this reference value, and therefore allows detection of alterations in the levels of protein of the subject with respect to the reference value.

In the context of the present invention, "increase in the levels" or "increased level" with respect to the reference value is understood as a variation of the levels above the reference value of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, or more, in comparison with the reference value.

On the other hand, in the method of the invention a decrease in the levels of sulfated GAGs with respect to the reference value is indicative of the subject suffering from a disease associated with a decrease in the levels of sulfated GAGs.

Similarly, "decrease in the levels" or "decreased level" with respect to the reference value is understood as a variation of the levels below the reference value of at least 5%, at least 10%, at least 15%, at least 20%, at least 25%, at least 300, at least 350, at least 400, at least 450, at least 50%, at least 55%, at least 60%, at least 65%, at least 70%, at least 750, at least 800, at least 850, at least 900, at least 950, or by at least 1000 (i.e., absent) in comparison with the reference value.

"Advanced kidney disease" is understood not only as the final stage of kidney disease, or terminal kidney disease, when the kidneys are no longer able to eliminate sufficient waste and dialysis or a kidney transplant are required, but rather also as the stage in which the disease has advanced such that the kidneys have virtually stopped carrying out their function and the symptomatology is mild, such as, for example, abnormally dark or light colored skin, bone pain, sleepiness or problems with concentration, numbing or swelling of the hands and feet, muscle fasciculations or cramps, bad breath, susceptibility to bruising or blood in feces, excessive thirst, frequent hiccups, amenorrhea, breathing difficulties, and vomiting.

These methods may essentially consist of the aforementioned steps, or they may include additional steps.

The remaining terms have been defined in preceding aspects. Any embodiment described above is applicable to the diagnostic methods of the invention.

Methods for Determining the Prognosis or for Monitoring the Progression of a Disease In another aspect, the invention relates to an in vitro method for determining the prognosis or for monitoring the progression of a disease associated with an increase in one or more sulfated GAGs in a subject, which comprises:
a) separating the free sulfated GAGs and the fraction bound to or associated with sulfated GAGs from a biological sample from said subject by means of the first method of the invention;
b) detecting the level of one or more sulfated GAGs separated in a); and
c) comparing said level with a reference value for said one or more sulfated GAGs obtained from the same subject at a prior time point, wherein a decrease in the level of one or more sulfated GAGs with respect to the reference value is indicative of the disease associated with an increase in one or more sulfated GAGs having a good prognosis, or wherein an increase in the level of one or more sulfated GAGs with respect to the reference value is indicative of the disease associated with an increase in one or more sulfated GAGs having a poor prognosis.

In another aspect, the invention relates to an in vitro method for determining the prognosis or for monitoring the progression of a disease associated with a decrease in one or more sulfated GAGs in a subject, which comprises:
a) separating the free sulfated GAGs and the fraction bound to or associated with sulfated GAGs from a biological sample from said subject by means of the first method of the invention;
b) detecting the level of one or more sulfated GAGs separated in a); and
c) comparing said level with a reference value for said one or more sulfated GAGs obtained from the same subject at a prior time point, wherein a decrease in the level of one or more sulfated GAGs with respect to the reference value is indicative of the disease associated with a decrease in one or more sulfated GAGs having a poor prognosis, or wherein an increase in the level of one or more sulfated GAGs with respect to the reference value is indicative of the disease associated with a decrease in one or more sulfated GAGs having a good prognosis.

In another aspect, the invention relates to an in vitro method for determining the prognosis or for monitoring the progression of a subject suffering from mucopolysaccharidosis, which comprises:
a) detecting the level of the signal peptide SEQ ID NO: 1 of uromodulin or of a variant thereof in a urine sample from said subject, and
b) comparing said level with a reference value obtained from the same subject at a prior time point, wherein a decrease in the level of the signal peptide SEQ ID NO: 1 of uromodulin or of a variant thereof with respect to the reference value is indicative of the disease having a good prognosis, or wherein an increase in the level of the signal peptide SEQ ID NO: 1 of uromodulin or of a variant thereof with respect to the reference value is indicative of the disease having a poor prognosis.

The homogenous urinary profile observed in the general population is altered in patients with kidney disease on a protein level and it could be used as kidney function and prognostic biomarker, where changes in the levels of creatinine, the current reference biomarker for kidney damage, are anticipated several years in advance since 50% of the kidney function may have been lost before the levels of creatinine change significantly.

On a protein level, this urinary fingerprint is associated with uromodulin and different GAGs (chondroitin, dermatan and heparan sulfate) known to be part of the glomerular basement membrane, the extracellular matrix, and the mucopolysaccharide layer of the uroepithelial surface. Uromodulin has an inverse expression pattern with respect to the levels of creatinine, which tends to drop progressively in patients with advanced kidney disease (determined by the levels of serum creatinine, proteinuria, and other clinical signs). The method of the invention has allowed observing that the greater the damage and progression of kidney failure, even without significant changes in the levels of creatinine, the lower the presence (semi-quantitative) of uromodulin associated with GAGs in urine.

In another aspect, the invention relates to an in vitro method for determining the prognosis or for monitoring the progression of a kidney disease in a subject which comprises detecting the level of uromodulin or of a variant thereof bound to or associated with sulfated GAGs, and/or detecting the level of albumin or of a variant thereof bound to or associated with sulfated GAGs in a urine sample from said subject, and comparing said level with a reference value obtained from the same subject at a prior time point, wherein a decrease in the level of uromodulin or of a variant thereof bound to or associated with sulfated GAGs and/or a decrease in the level of albumin or of a variant thereof bound to or associated with sulfated GAGs with respect to the reference value is indicative of the disease having a poor prognosis, or wherein an increase in the level of uromodulin or of a variant thereof bound to or associated with sulfated GAGs and/or an increase in the level of albumin or of a variant thereof bound to or associated with sulfated GAGs with respect to the reference value is indicative of the disease having a good prognosis.

In another aspect, the invention relates to an in vitro method for determining the prognosis or for monitoring the progression of an advanced kidney disease in a subject, which comprises:

a) detecting the level of uromodulin- or uromodulin variant-sulfated GAG-exosomes complexes in a urine sample from said subject; and
b) comparing said level with a reference value obtained from the same subject at a prior time point, wherein a decrease in the level of uromodulin- or uromodulin variant-sulfated GAG-exosomes complexes with respect to the reference value is indicative of the disease having a poor prognosis, or wherein an increase in the level of uromodulin- or uromodulin variant-sulfated GAG-exosomes complexes with respect to the reference value is indicative of the disease having a good prognosis.

The progression of the disease can be easily followed according to these methods.

As it is used herein, the expression "monitoring the progression" of a disease, which is equivalent to "determining the prognosis", refers to the determination of one or more parameters indicating the progression of the disease in a patient diagnosed with said disease. Parameters suitable for determining the progression of a subject diagnosed with a disease are, without limitation, risk of relapse, disease-free survival, and/or overall survival of the subject. In this specification, the expression "risk of relapse" is understood as the probability of a subject developing the disease after a disease-free period; "disease-free survival" is understood as the time period after the treatment in which the disease is not detected; and the "overall survival of the subject" is understood as the percentage of subjects who survive, from the time of the diagnosis or treatment, after a defined time period.

According to these aspects of the invention, the levels of one or more sulfated GAGs, or the levels of protein in a biological sample from a subject having the disease are obtained in a first time period (first sample from the subject), and the levels of one or more sulfated GAGs or the levels of protein in a biological sample from the same subject are obtained in a second time period (second sample from the subject) and are compared, which allows monitoring the progression of the disease. The second sample from the subject can be taken from the same subject from whom the first measurement is derived in a second time period, i.e., at any time after the first time period, for example, one day, one week, a month, two months, three months, 1 year, 2 years, or more after the first sample from the subject. In a particular embodiment, the first sample from the subject is taken before receiving the treatment, and the second sample from the subject is taken after the treatment. In another particular embodiment, the first sample from the subject is taken after the subject has started to receive treatment, and the second sample from the subject is taken later in different periods of time during the course of treatment.

The term "good prognosis" means that the disease is not progressing. "Good prognosis" also refers to a positive outcome for the patient and depends on the type of prognosis; for example, a good prognosis of one year of survival means that the patient will survive for at least one year. In a preferred embodiment, a good prognosis refers to a probability of more than 40% of surviving 5 years after diagnosis of the disease.

The term "poor prognosis" means that the disease is progressing and that the therapy administered to the subject under study must be changed, and a new therapy must be designed to treat the disease. "Poor prognosis" also refers to a negative outcome for the patient and depends on the type of prognosis; for example, a poor prognosis of one year of survival means that the patient will not survive for at least 1 year. In a preferred embodiment, a poor prognosis refers to a probability of less than 40% of surviving 5 years after diagnosis of the disease.

In a preferred embodiment, the separation of uromodulin and/or albumin associated with sulfated GAG or the separation of the uromodulin- or uromodulin variant-sulfated GAG-exosomes complexes from the urine sample is performed according to the first method of the invention.

The levels of sulfated GAGs can be determined as described above.

As mentioned above in relation to the diagnostic method of the invention, the levels of proteins or of variants thereof can be determined by means of any suitable method known in the art, such as Western blot or ELISA, for example.

In another preferred embodiment, the detection is performed by means of mass spectrometry, preferably tandem mass spectrometry.

Once the expression levels of the protein or of a variant thereof in the samples obtained from a subject in different time periods (first and second samples of the subject) have been determined, it is necessary to identify if there is a significant increase or decrease in the expression of said protein in the second sample from the subject in comparison with the expression level of said protein in the first sample from the subject.

The terms "increase in the levels" and "decrease in the levels" applied to the level of sulfated GAGs or to the expression level of a protein or a variant thereof have been defined above in the context of the diagnostic methods of the invention.

In a preferred embodiment, the kidney disease is autosomal dominant polycystic kidney disease type 1 or type 2, preferably autosomal dominant polycystic kidney disease type 1 or type 2 associated with known mutations in the PKD1 gene (chr16:41711del18 bp; chr16:28907c>g; chr16:37060c>t) and PKD2 gene (chr4:88995974c>t).

Most terms have been defined above in the context of the diagnostic method of the invention and are likewise applied to this inventive aspect.

The embodiments described for the preceding inventive aspects are also applicable to the prognostic methods of the invention.

Methods for Monitoring the Effect of a Therapy

The invention also provides methods for determining the efficacy of a therapy for treating a disease associated with an increase in one or more sulfated GAGs, of a disease associated with a decrease in one or more sulfated GAGs, and particularly of mucopolysaccharidosis and kidney disease.

In another aspect, the invention relates to an in vitro method for monitoring the effect of a therapy for the treatment of a disease associated with an increase in one or more sulfated GAGs, which comprises:
a) separating the free sulfated GAGs and the fraction bound to or associated with sulfated GAGs from a biological sample from a subject suffering from said disease and who has been treated with said therapy by means of the first method of the invention; and
b) detecting the level of one or more sulfated GAGs separated in a), wherein a decrease in the level of one or more sulfated GAGs with respect to the level of the same sulfated GAG in a sample from the same subject before therapy is indicative of the administered therapy being effective, or wherein an increase or the absence of change in the level of one or more sulfated GAGs with respect to the level of the same sulfated GAG in a sample from the same subject before therapy is indicative of the administered therapy being ineffective or of the subject needing an alternative therapy.

In another aspect, the invention relates to an in vitro method for monitoring the effect of a therapy for the treatment of a disease associated with a decrease in one or more sulfated GAGs, which comprises:
a) separating the free sulfated GAGs and the fraction bound to or associated with sulfated GAGs from a biological sample from a subject suffering from said disease and who has been treated with said therapy by means of the first method of the invention; and
b) detecting the level of one or more sulfated GAGs separated in a), wherein an increase in the level of one or more sulfated GAGs with respect to the level of the same sulfated GAG in a sample from the same subject before therapy is indicative of the administered therapy being effective, or wherein a decrease or the absence of change in the level of one or more sulfated GAGs with respect to the level of the same sulfated GAG in a sample from the same subject before therapy is indicative of the administered therapy being ineffective or of the subject needing an alternative therapy.

In another aspect, the invention relates to an in vitro method for monitoring the effect of a therapy in a subject suffering from mucopolysaccharidosis and who is treated with said therapy, which comprises:
a) detecting the level of the signal peptide SEQ ID NO: 1 of uromodulin or of a variant thereof in a urine sample from said subject, and
b) comparing said level with a reference value obtained from the same subject before therapy, wherein a decrease in the level of the signal peptide SEQ ID NO: 1 of uromodulin or of a variant thereof with respect to the reference value is indicative of the administered therapy being effective, or wherein an increase in the level of the signal peptide SEQ ID NO: 1 of uromodulin or of a variant thereof with respect to the reference value is indicative of the administered therapy being ineffective or of the subject needing an alternative therapy.

In another aspect, the invention relates to an in vitro method for monitoring the effect of a therapy in a subject suffering from a kidney disease and who is treated with said therapy, which comprises:
a) detecting the level of uromodulin or of a variant thereof bound to or associated with sulfated GAGs and/or detecting the level of albumin or of a variant thereof bound to or associated with sulfated GAGs in a urine sample from said subject, and
b) comparing said level with a reference value obtained from the same subject before therapy, wherein an increase in the level of uromodulin or of a variant thereof bound to or associated with sulfated GAGs and/or an increase in the level of albumin or of a variant thereof bound to or associated with sulfated GAGs with respect to the reference value is indicative of the administered therapy being effective, or wherein a decrease in the level of uromodulin or of a variant thereof bound to or associated with sulfated GAGs and/or a decrease in the level of albumin or of a variant thereof bound to or associated with sulfated GAGs with respect to the reference value is indicative of the administered therapy being ineffective or of the subject needing an alternative therapy.

In another aspect, the invention relates to an in vitro method for monitoring the effect of a therapy in a subject suffering from an advanced kidney disease and who is treated with said therapy, which comprises:
a) detecting the level of uromodulin- or uromodulin variant-sulfated GAG-exosomes complexes in a urine sample from said subject, and
b) comparing said level with a reference value obtained from the same subject before therapy, wherein an increase in the level of uromodulin- or uromodulin variant-sulfated GAG-exosomes complexes with respect to the reference value is indicative of the administered therapy being effective, or wherein a decrease in the level of uromodulin- or uromodulin variant-sulfated GAG-exosomes complexes with respect to the reference value is indicative of the administered therapy being ineffective or of the subject needing an alternative therapy.

In a preferred embodiment, the separation of uromodulin and/or albumin associated with sulfated GAGs or the separation of the uromodulin- or uromodulin variant-sulfated GAG-exosomes complexes from the urine sample is performed according to the first method of the invention.

As it is used herein, the expression "monitoring the effect of a therapy" refers to performing the follow-up of the disease throughout treatment for determining whether or not it is effective.

As it is used herein, the term "therapy" or "treatment" collectively refers to means of any type (hygienic means, pharmacological means, surgical means, or physical means) the purpose of which is to prevent and/or cure or alleviate a disease or pathology or the symptoms thereof. In one embodiment, the therapy is selected from diet therapy, pharmacological treatment, exercise therapy, and a combination thereof. In a preferred embodiment, said treatment is a pharmacological treatment, i.e., a treatment comprising the administration of a drug to a subject to prevent, alleviate, and/or cure a disease; or to alleviate, reduce, or eliminate one or more symptoms associated with said disease.

In the present invention, "standard therapy" or "conventional therapy" is understood as a therapy that uses those drugs which have demonstrated clinical efficacy in randomized, phase III studies, alone or in combinations similar to those used in the present invention. For example, the conventional therapy for the treatment of mucopolysaccharidosis can be symptomatic therapy, enzyme replacement therapies, substrate inhibitors, and bone marrow transplant (hematopoietic progenitor cells). The conventional therapy for the treatment of kidney disease depends on the etiology thereof, and can be, without limitation, immunosuppressants such as tacrolimus or cyclosporine; restriction or supplements of mineral salts such as sodium, potassium, magnesium; diet or diuretics such as amiloride, triamterene, or tolvaptan; and on other cases, the only solution is dialysis or transplant. These treatments are known to nephrology experts.

In the present invention, "alternative therapy" is understood as a therapy other than the original therapy, herein referred to as standard therapy, administered to a subject. Said "alternative therapy" includes significant variations with respect to the standard therapy, such as the replacement of some agents with others, the addition of alternative agents, change in doses or increase in the intensity of the dose of the drugs, addition of other agents (approved or in the experimental stage), alteration in the sequence of administration of the agents or the type of local treatments, such as surgery or radiotherapy, etc. The alternative therapies herein defined are probably associated with more significant side effects for the subject (although not necessarily), and foreseeably associated with a greater effectiveness. Specific examples of agents included within the alternative therapy for mucopolysaccharidosis could be enzyme "enhancement" therapy when there is residual enzyme activity, or gene therapy in the process of a clinical trial. Specific examples of agents included within the alternative therapy for a kidney disease could be any of the agents that have not been used as standard therapy and, preferably, dialysis and/or kidney transplant.

The reference sample is a sample from the same patient suffering from the disease who has not been treated or who has been treated with control therapy, preferably, the same excipient, support, or carrier which is used in the therapy the efficacy of which is going to be evaluated.

In another preferred embodiment, detection is performed by means of mass spectrometry, preferably tandem mass spectrometry.

In a preferred embodiment, the kidney disease is autosomal dominant polycystic kidney disease type 1 or type 2.

The different embodiments of the diagnostic and prognostic methods of the invention (the methods used for determining the levels of the markers, the nature of the sample that is going to be studied, the thresholds for considering that a marker has increased or decreased) are essentially as they have been defined above with respect to the diagnostic and prognostic methods of the invention.

Methods for Identifying Compounds Suitable for the Treatment of a Disease

The authors of the present invention have also developed a method for identifying a compound suitable for the treatment of diseases associated with an increase or a decrease in one or more sulfated GAGs, of mucopolysaccharidosis and of a kidney disease. The identification of a series of markers the levels of which increase or decrease with respect to reference samples allows the screening of compounds in a model of these diseases which are capable of restoring the levels of the markers to those found in normal samples.

In one aspect, the invention relates to an in vitro method for identifying compounds suitable for the treatment of a disease associated with an increase in one or more sulfated GAGs, which comprises:
 a) separating the free sulfated GAGs and the fraction bound to or associated with sulfated GAGs from a biological sample from a subject suffering from said disease and who has been treated with a candidate compound by means of the first method of the invention; and
 b) detecting the level of one or more sulfated GAGs separated in a),
wherein the compound is considered effective for the treatment of the disease when the level of one or more sulfated GAGs decreases with respect to the level of the same sulfated GAG in a reference sample.

In another aspect, the invention relates to an in vitro method for identifying compounds suitable for the treatment of a disease associated with a decrease in one or more sulfated GAGs, which comprises:
 a) separating the free sulfated GAGs and the fraction bound to or associated with sulfated GAGs from a biological sample from a subject suffering from said disease and who has been treated with a candidate compound by means of the first method of the invention; and
 b) detecting the level of one or more sulfated GAGs separated in a),
wherein the compound is considered effective for the treatment of the disease when the level of one or more sulfated GAGs increases with respect to the level of the same sulfated GAG in a reference sample.

In another aspect, the invention relates to an in vitro method for identifying compounds suitable for the treatment of mucopolysaccharidosis, which comprises:
 a) detecting the level of the signal peptide SEQ ID NO: 1 of uromodulin or of a variant thereof in a urine sample from a subject suffering from mucopolysaccharidosis and who has been treated with a candidate compound, and
 b) comparing said level with a reference value,
wherein the compound is considered effective for the treatment of the disease when the level of the signal peptide SEQ ID NO:1 of uromodulin or of a variant thereof decreases with respect to the reference value.

In another aspect, the invention relates to an in vitro method for identifying compounds suitable for the treatment of a kidney disease, which comprises:
 a) detecting the level of uromodulin or of a variant thereof bound to or associated with sulfated GAGs and/or detecting the level of albumin or of a variant thereof bound to or associated with sulfated GAGs in a urine sample from a subject suffering from a kidney disease and who has been treated with a candidate compound, and
 b) comparing said level with a reference value,
wherein the compound is considered effective for the treatment of the disease when the level of uromodulin or of a variant thereof bound to or associated with sulfated GAGs and/or the level of albumin or of a variant thereof bound to or associated with sulfated GAGs increases with respect to the reference value.

In another aspect, the invention relates to an in vitro method for identifying compounds suitable for the treatment of an advanced kidney disease, which comprises:
 a) detecting the level of uromodulin- or uromodulin variant-sulfated GAG-exosomes complexes in a urine sample from a subject suffering from an advanced kidney disease and who has been treated with a candidate compound, and
 b) comparing said level with a reference value,
wherein the compound is considered effective for the treatment of the advanced kidney disease when the level of uromodulin- or uromodulin variant-sulfated GAG-exosomes complexes increases with respect to the reference value.

In a preferred embodiment, the separation of uromodulin and/or albumin associated with sulfated GAGs, or the separation of the uromodulin- or uromodulin variant-sulfated GAG-exosomes complexes from the urine sample is performed according to the first method of the invention.

The expression "identifying the compounds suitable for the treatment of a disease" refers to a screening method both for the identification of effective compounds for the treatment of the existing disease and for the preventive treatment (i.e., prophylaxis). The term "treatment" has been defined in the context of the methods for monitoring a therapy.

As it is used with respect to this method, the term "reference sample" refers to a sample derived from a sick subject in whom the therapy is being tested, but obtained from the sick subject before the administration of said therapy. The reference sample can also be a sample from a subject suffering from the disease and who has not been treated or has been treated with control therapy, preferably the same excipient, support, or carrier which is used in the candidate compound being screened.

The subject can be a patient or an animal used as a model of the disease. The examples of animals suitable for use in the screening method of the invention include, but are not limited to, mice, rats, rabbits, monkeys, guinea pigs, dogs, and cats. According to this embodiment, the compound to be tested or a control compound is administered (for example, by oral, rectal, or parenteral route, such as by intraperitoneal or intravenous route) to a suitable animal and the effect on the levels of one or more of the markers is determined. The examples of agents include, but are not limited to, nucleic acids (for example DNA and RNA), carbohydrates, lipids, proteins, peptides, peptidomimetics, small molecules, and other drugs. The agents can be obtained using any of the numerous approaches in the methods of combinatorial libraries known in the art. The compounds to be tested furthermore include, for example, antibodies (for example, polyclonal, monoclonal, humanized, anti-idiotypic, chimeric, and single-chain antibodies, as well as fragments Fab, F(ab')2, Fab expression libraries, and epitope-binding antibody fragments). Furthermore, the agents or libraries of compounds can be presented, for example, in solution, in balls, chips, bacteria, spores, plasmids, or phages.

If the compound is a low molecular weight compound, then it can be generated by means of several methods known in the art, preferably synthetically, particularly by means of combinatorial chemistry, or by means of biochemical methods, particularly by means of recombinant expression or purification based on biological probes. The compound can be a low molecular weight compound ("small molecules"), or the library can be made up of low molecular weight molecules ("small molecule library"). A "small molecule" is defined as a complex collection of compounds, which are produced in a non-biological manner, which means that they are not produced by means of recombinant expression, such as, for example most protein or peptide libraries. "Small molecules" can be generated by means of several methods known in the art, but they are preferably produced synthetically, more preferably by means of combinatorial chemistry, to generate a library of compounds with maximum chemical diversity within the restrictions of the aforesaid characteristics of a drug of interest. If the compound the suitability of which for treating a disease is being tested is a peptide or a peptide library, then these peptides can be generated by means of several methods known in the art for use as candidate compounds, but they are preferably produced by means of biochemical methods, more preferably by means of recombinant expression in prokaryotic or eukaryotic cells.

The compound the suitability of which is going to be tested for therapy can be formulated with a pharmaceutically acceptable support for producing a pharmaceutical composition, which can be administered to a human being or another animal. A pharmaceutically acceptable support can be, for example, water, sodium phosphate buffer, phosphate-buffered saline solution, normal saline solution, or Ringer's solution, or another physiologically buffered saline solution, or another solvent or carrier, such as a glycol, glycerol, an oil such as olive oil, or an injectable organic ester. A pharmaceutically acceptable support can also contain physiologically acceptable compounds which act, for example, to stabilize or increase absorption of the modulating compound. One skilled in the art would know that the election of a pharmaceutically acceptable support, including a physiologically acceptable compound, depends, for example, on the route for the administration of the composition.

In another preferred embodiment, detection is performed by means of mass spectrometry, preferably tandem mass spectrometry.

In a preferred embodiment, the kidney disease is autosomal dominant polycystic kidney disease type 1 or type 2.

The different embodiments of the diagnostic and prognostic methods of the invention (the methods used for determining the levels of the markers, the nature of the sample that is going to be studied, the thresholds for considering that a marker has increased or decreased) are essentially as they have been defined above with respect to the diagnostic and prognostic methods of the invention.

Methods for Designing a Personalized Therapy or for Selecting a Patient Susceptible to being Treated with a Therapy for the Prevention and/or Treatment of a Disease In one aspect, the invention relates to an in vitro method for designing a personalized therapy in a subject having symptoms of mucopolysaccharidosis, which comprises:

a) detecting the level of the signal peptide SEQ ID NO: 1 of uromodulin or of a variant thereof in a urine sample from said subject, and b) comparing said level with a reference value, wherein an increased level of the signal peptide SEQ ID NO: 1 of uromodulin or of a variant thereof with respect to the reference value is indicative of said subject being susceptible to receiving a therapy for the prevention and/or treatment of mucopolysaccharidosis.

In another aspect, the invention relates to an in vitro method for selecting a patient susceptible to being treated with a therapy for the prevention and/or treatment of mucopolysaccharidosis, which comprises:

a) detecting the level of the signal peptide SEQ ID NO: 1 of uromodulin or of a variant thereof in a urine sample from said subject, and b) comparing said level with a reference value, wherein an increased level of the signal peptide SEQ ID NO: 1 of uromodulin or of a variant thereof with respect to the reference value is indicative of said subject being a candidate for receiving a therapy for the prevention and/or treatment of mucopolysaccharidosis.

In another aspect, the invention relates to an in vitro method for designing a personalized therapy in a subject having symptoms of a kidney disease, which comprises:

a) detecting the level of uromodulin or of a variant thereof bound to or associated with sulfated GAGs and/or detecting the level of albumin or of a variant thereof bound to or associated with sulfated GAGs in a urine sample from said subject, and b) comparing said level with a reference value, wherein a decrease in the level of uromodulin or of a variant thereof bound to or associated with sulfated GAGs and/or a decrease in the level of albumin or of a variant thereof bound to or associated with sulfated GAGs with respect to the reference value is indicative of said subject being susceptible to receiving a therapy for the prevention and/or treatment of a kidney disease.

In another aspect, the invention relates to an in vitro method for selecting a patient susceptible to being treated with a therapy for the prevention and/or treatment of a kidney disease, which comprises:

a) detecting the level of uromodulin or of a variant thereof bound to or associated with sulfated GAGs and/or detecting the level of albumin or of a variant thereof bound to or associated with sulfated GAGs in a urine sample from said subject, and b) comparing said level with a reference value, wherein a decrease in the level of uromodulin or of a variant thereof bound to or associated with sulfated GAGs and/or a decrease in the level of albumin or of a variant thereof bound to or associated with sulfated GAGs with respect to the reference value is indicative of said subject being a candidate for receiving a therapy for the prevention and/or treatment of the kidney disease.

In another aspect, the invention relates to an in vitro method for designing a personalized therapy in a subject having symptoms of an advanced kidney disease, which comprises:

a) detecting the level of uromodulin- or uromodulin variant-sulfated GAG-exosomes complexes in a urine sample from said subject, and b) comparing said level with a reference value, wherein a decrease in the level of uromodulin- or uromodulin variant-sulfated GAG-exosomes complexes with respect to the reference value is indicative of said subject being susceptible to receiving a therapy for the treatment of the advanced kidney disease.

In another aspect, the invention relates to an in vitro method for selecting a patient susceptible to being treated with a therapy for the treatment of an advanced kidney disease, which comprises:

a) detecting the level of uromodulin- or uromodulin variant-sulfated GAG-exosomes complexes in a urine sample from said subject, and b) comparing said level with a reference value, wherein a decrease in the level of uromodulin- or uromodulin variant-sulfated GAG-exosomes complexes with respect to the reference value is indicative of said subject being a candidate for receiving a therapy for the treatment of the advanced kidney disease.

In a preferred embodiment, the separation of uromodulin and/or albumin associated with sulfated GAGs, or the separation of the uromodulin- or uromodulin variant-sulfated GAG-exosomes complexes from the urine sample is performed according to the first method of the invention.

In another preferred embodiment, detection is performed by means of mass spectrometry, preferably tandem mass spectrometry.

In a preferred embodiment, the kidney disease is autosomal dominant polycystic kidney disease type 1 or type 2.

As it is used herein, the expression "designing a personalized therapy" refers to the design and application of interventions for prevention and treatment adapted to the genetic substrate of the patient and for the molecular profile of the disease.

As it is used herein, the expression "symptoms of mucopolysaccharidosis" refers to the symptoms produced by said disease, which vary depending on the type of mucopolysaccharidosis involved. For example, the symptoms may include hearing losses, developmental delays, hydrocephaly, retinal degeneration and glaucoma, coarse facial features, short in stature (dwarfism), dysplasia, skeletal irregularities, thickening of the skin, enlarged liver or enlarged spleen, hernias, hirsutism, carpal tunnel syndrome, recurrent respiratory infections, obstructive diseases of the respiratory tract, sleep apnea, heart diseases.

As it is used herein, the expression "symptoms of a kidney disease" refers to symptoms which are present at an initial stage of the disease, when said disease goes unnoticed, for example and without limitation, lack of appetite, feeling of malaise and fatigue, headaches, pruritus and dry skin, nausea, and weight loss.

As it is used herein, the expression "symptoms of an advanced kidney disease" refers to the symptoms that appear when the kidney disease has already affected kidney function, such as, without limitation, abnormally dark or light colored skin, bone pain, sleepiness or problems with concentration, numbing or swelling of the hands and feet, muscle fasciculations or cramps, bad breath, susceptibility to bruising or blood in feces, excessive thirst, frequent hiccups, amenorrhea, breathing difficulties, and vomiting.

As it is used herein, the term "preventive therapy" or "therapy for the prevention" refers to the prevention or set of prophylactic measures for preventing a disease or for preventing or delaying the onset of the symptomatology thereof. Particularly, said term refers to the prevention or the set of measures for preventing the onset or for delaying the clinical symptomatology associated with mucopolysaccharidosis or with the kidney disease. Desired clinical results associated with the administration of said treatment to a subject include, but are not limited to, the stabilization of the pathological state of the disease, delay in progression of the disease, or improvement in the physiological state of the subject.

As it is used herein, "therapy for the treatment" refers to the tentative recovery from a health issue, generally after a diagnosis, specifically of mucopolysaccharidosis or of a kidney disease. As such, it is not necessarily a cure, i.e., complete reversal of a disease. Therefore, as it is used herein "treatment" covers any treatment of a disease, disorder, or condition of a mammal, particularly a human being, and includes inhibiting the disease or the condition, i.e., stopping its development; or alleviating the disease or condition, i.e., causing the regression of the disease or condition or the improvement of one or more symptoms of the disease or condition. The population of subjects treated by means of the method includes a subject suffering from unwanted condition or disease, as well as subjects at risk of developing the condition or disease. Therefore, one skilled in the art understands that a treatment may improve the condition of the patient, but it may not be a complete cure for the disease.

Preventive or curative treatments suitable in mucopolysaccharidosis include, but are not limited to, iduronidase for MPS I, idursulfase for MPS II, N-acetylgalactosamine-6-sulfate sulfatase (Galns) for MPS IVA, human recombinant arylsulfatase for MPS VI (all of which are enzyme replacement therapies); hematopoietic progenitor cell transplant, including umbilical cord blood transplant, erythropoietic stem cell transplant, peripheral blood stem cell transplant; substrate reduction therapy in the event of there being a certain residual enzyme activity.

Preventive or curative treatments suitable in kidney disease include, but are not limited to, symptomatic or palliative treatment; cause-specific treatment (if it is bacterial, use of antibiotics, etc); immunosuppressants such as tacrolimus or cyclosporine; restriction or supplements of mineral salts such as sodium, potassium, magnesium; diet or diuretics such as amiloride, triamterene, or tolvaptan; dialysis (peritoneal, hemodialysis), and kidney transplant.

Preventive or curative treatments suitable in the advanced kidney disease are the same as those that have been mentioned in the preceding paragraph in the context of kidney disease.

As it is used herein, the term "selecting" refers to the action of electing a subject so as to subject him or her to preventive or curative treatment for mucopolysaccharidosis or kidney disease.

The different embodiments of the diagnostic and prognostic methods of the invention (the methods used for determining the levels of the markers, the nature of the sample that is going to be studied, the thresholds for considering that a marker has increased or decreased) are essentially as they have been defined above with respect to the diagnostic and prognostic methods of the invention.

Other Aspects of the Invention

In another aspect, the invention relates to the use of an agent capable of detecting the signal peptide SEQ ID NO: 1 of uromodulin or a variant thereof in a urine sample for diagnosing mucopolysaccharidosis, for determining the prognosis or for monitoring the progression of a subject suffering from mucopolysaccharidosis, for monitoring the effect of a therapy in a subject suffering from mucopolysaccharidosis, for designing a personalized therapy in a subject having symptoms of mucopolysaccharidosis, for selecting a patient susceptible to being treated with a therapy for the prevention and/or treatment of mucopolysaccharidosis, or for identifying compounds suitable for the treatment of mucopolysaccharidosis. In one embodiment, the agent capable of detecting the signal peptide SEQ ID NO: 1 of uromodulin or a variant thereof is selected from the group consisting of an enzyme capable of specifically recognizing an amino acid sequence of the signal peptide of SEQ ID NO: 1 of uromodulin or of a variant thereof and cleaving said peptide, an antibody, an aptamer, and fragments thereof that bind specifically to the signal peptide SEQ ID NO: 1 of uromodulin or to a variant thereof.

In a preferred embodiment, the agent is an antibody capable of specifically detecting a peptide of sequence SEQ ID NO: 1 or a variant thereof, and incapable of detecting mature or secreted uromodulin, or a fragment of said antibody with the capacity to bind to sequence SEQ ID NO: 1 or a variant thereof. In another embodiment, the agent is an aptamer capable of specifically detecting a peptide of sequence SEQ ID NO: 1 or a variant thereof, and incapable of detecting mature or secreted uromodulin, or a fragment of said aptamer with the capacity to bind to sequence SEQ ID NO: 1 or a variant thereof. In another embodiment, the agent is an enzyme capable of specifically recognizing an amino acid sequence of the signal peptide of SEQ ID NO: 1 or of a variant thereof and cleaving said peptide, and incapable of recognizing an amino acid sequence of mature or secreted uromodulin and cleaving it.

In another aspect, the invention relates to the use of the signal peptide SEQ ID NO: 1 of uromodulin or a variant thereof as a diagnostic marker for mucopolysaccharidosis, as a prognostic marker for mucopolysaccharidosis, as a marker for monitoring the progression of a subject suffering from mucopolysaccharidosis, as a marker for monitoring the effect of a therapy in a subject suffering from mucopolysaccharidosis, as a marker for designing a personalized therapy in a subject having symptoms of mucopolysaccharidosis, as a marker for selecting a patient susceptible to being treated with a therapy for the prevention and/or treatment of mucopolysaccharidosis, or as a marker for identifying compounds suitable for the treatment of mucopolysaccharidosis.

In another aspect, the invention relates to the use of an agent capable of detecting uromodulin or a variant thereof bound to or associated with sulfated GAGs and/or of an agent capable of detecting albumin or a variant thereof bound to or associated with sulfated GAGs in a urine sample for diagnosing a kidney disease, for determining the prognosis or for monitoring the progression of a subject suffering from a kidney disease, for monitoring the effect of a therapy in a subject suffering from a kidney disease, for designing a personalized therapy in a subject having symptoms of a kidney disease, for selecting a patient susceptible to being treated with a therapy for the prevention and/or treatment of a kidney disease, or for identifying compounds suitable for the treatment of a kidney disease.

In another aspect, the invention relates to the use of uromodulin or a variant thereof bound to or associated with sulfated GAGs, and/or of albumin or of a variant thereof bound to or associated with sulfated GAGs as a diagnostic marker for a kidney disease, as a prognostic marker for a kidney disease, as a marker for monitoring the effect of a therapy in a subject suffering from a kidney disease, as a marker for designing a personalized therapy in a subject having symptoms of a kidney disease, as a marker for selecting a patient susceptible to being treated with a therapy for the prevention and/or treatment of a kidney disease, or as a marker for identifying compounds suitable for the treatment of a kidney disease.

In another aspect, the invention relates to the use of an agent capable of detecting uromodulin- or uromodulin variant-sulfated GAG-exosomes complexes in a urine sample for diagnosing an advanced kidney disease, for determining the prognosis or for monitoring the progression of a subject suffering from an advanced kidney disease, for monitoring the effect of a therapy in a subject suffering from an advanced kidney disease, for designing a personalized therapy in a subject having symptoms of an advanced kidney disease, for selecting a patient susceptible to being treated with a therapy for the treatment of an advanced kidney disease, or for identifying compounds suitable for the treatment of an advanced kidney disease.

In another aspect, the invention relates to the use of a uromodulin- or uromodulin variant-sulfated GAG-exosomes complex as a diagnostic marker for an advanced kidney disease, as a prognostic marker for an advanced kidney disease, as a marker for monitoring the effect of a therapy in a subject suffering from an advanced kidney disease, as a marker for designing a personalized therapy in a subject having symptoms of an advanced kidney disease, as a marker for selecting a patient susceptible to being treated with a therapy for the treatment of an advanced kidney disease, or as a marker for identifying compounds suitable for the treatment of an advanced kidney disease.

The term "agent" refers to any compound or reagent that allows detecting the presence of the signal peptide SEQ ID NO: 1, or capable of detecting uromodulin or a variant thereof bound to or associated with sulfated GAGs, or capable of detecting albumin or a variant thereof bound to or associated with sulfated GAGs, or capable of detecting uromodulin- or uromodulin variant-sulfated GAG-exosomes complexes in a sample.

In one embodiment, the agent is selected from the group consisting of an antibody, an aptamer, and fragments thereof that bind specifically to the signal peptide SEQ ID NO: 1, to uromodulin, to albumin, or to a variant thereof. In another embodiment, the agent is an enzyme capable of specifically recognizing an amino acid sequence of the signal peptide of SEQ ID NO: 1, of uromodulin, of albumin, or of a variant thereof, and cleaving them.

In a preferred embodiment, the agent is an antibody. In another preferred embodiment, the agent is a reagent for mass spectrometry.

The term "marker" is equivalent to the term "biomarker", which has been defined above. The marker is preferably a protein or lipid compound.

In a preferred embodiment, the separation of uromodulin and/or albumin associated with sulfated GAGs or the separation of the uromodulin- or uromodulin variant-sulfated GAG-exosomes complexes from the urine sample is performed according to the first method of the invention.

In a preferred embodiment, the kidney disease is autosomal dominant polycystic kidney disease type 1 or type 2.

Complexes of the Invention

The inventors have discovered the existence of complexes formed by uromodulin, sulfated GAGs, and exosomes in the urine of healthy subjects, and also in the urine of subjects suffering from kidney disease. These complexes may include other proteins.

Based on exosome purification, specific GAG precipitation, and protein sequencing studies, the inventors have determined that exosomes and GAGs together with uromodulin form a complex which may be directing the communication between the different segments of the nephron.

Therefore, in another aspect, the invention relates to a complex formed by the association of uromodulin or a uromodulin variant, sulfated GAGs, and exosomes.

In a preferred embodiment of the invention, the complex is isolated, i.e., substantially free of other components present in the urine.

Kits of the Invention

In another aspect, the invention relates to a kit comprising dimethylmethylene blue (DMB) at a concentration comprised between 0.01 and 100 nM at a pH comprised between 2 and 6.9.

In a preferred embodiment, the pH is comprised between 3 and 4; preferably between 3.3 and 3.6; more preferably it is 3.5.

In another preferred embodiment, the concentration of DMB is comprised between 0.29 and 0.35 mM, and wherein the pH is comprised between 3.3 and 3.6, and the buffer agent is formate buffer.

As it is used herein, the term "kit" refers to a combination of a set of reagents suitable for separating the free sulfated GAGs and the fraction bound to sulfated GAGs from a sample together with one or more types of elements or components for carrying out the methods of the invention, particularly for analyzing the protein or lipid pattern of the fraction bound to sulfated GAGs, and optionally reagents suitable for detecting the levels of sulfated GAGs, mature or secreted uromodulin, the peptide of sequence SEQ ID NO: 1 of uromodulin, albumin, IgA, and/or IgG. The kit optionally includes other types of biochemical reagents, containers, packaging suitable for commercial sale, electronic hardware and software components, etc. The reagents are packaged to allow for their transport and storage. Materials suitable for packaging the components of the kit include glass, plastic (polyethylene, polypropylene, polycarbonate, and the like), bottles, vials, paper, sachets, and the like. Additionally, the kits of the invention may contain instructions for the simultaneous, sequential, or separate use of the different components in the kit. Said instructions can be found in the form of printed material or in the form of an electronic support capable of storing instructions such that they can be read by a subject, such as electronic storage media (magnetic disks, tapes, and the like), optical media (CD-ROM, DVD), and the like. Additionally or alternatively, the media may contain Internet addresses which provide said instructions.

In another preferred embodiment, the kit further comprises a gel selected from the group consisting of a polyacrylamide gel and a cellulose acetate gel.

As it is used herein, the term "polyacrylamide gel" refers to a hydrogel that is formed by an acrylamide homopolymer and is one of the gels most commonly used to perform protein electrophoresis, specifically polyacrylamide gel (PAGE) electrophoresis. These gels are chemically inert, transparent, and stable in a wide range of pH, temperature, and ionic strength.

As it is used herein, the term "cellulose acetate gel" refers to a medium used for the separation and characterization of proteins and other molecules according to their charge density. The support consists of thin strips of cellulose acetate with minimum adsorption properties, so separation into well-defined bands is achieved.

In another preferred embodiment, the kit further comprises a loading buffer.

As it is used herein, the term "loading buffer" refers to the buffer which is added to the sample that will be loaded in the well of the polyacrylamide gel or in the cellulose acetate support. Generally, this buffer contains water, sucrose, and a dye (for example, xylene cyanol, bromophenol blue, bromocresol green, etc.). Examples of loading buffers can be, without limitation, Laemli buffer; Laemli buffer with β-mercaptoethanol and 7.5% SDS at a 1:1 ratio; TBE buffer (100 mM Tris-borate, 1 mM EDTA, pH 8.3) with 2 M sucrose, and 0.02% bromophenol blue; TAE buffer (40 mM Tris, 5 mM $CH_3COONa$, 0.9 mM EDTA, pH 7.9); and TBE buffer with 2 M sucrose. In a preferred embodiment, the loading buffer is 7.5% SDS.

In another preferred embodiment, the kit further comprises an electrophoresis buffer.

As it is used herein, the term "electrophoresis buffer" refers to the buffer in which the gel is submerged for performing electrophoresis. Examples of electrophoresis buffer are, without limitation, TAE 1× or 0.5×, TBE 1×, Tris-glycine 1×, and 0.05 M barium acetate. In a preferred embodiment, the electrophoresis buffer is 0.05 M barium acetate.

In another embodiment, the kit further comprises a dye specific for viewing proteins as defined in the context of the first method of the invention. In an even more preferred embodiment, the dye is Sypro Ruby.

In another embodiment, the kit further comprises a destaining agent, preferably acetic acid, more preferably 10% acetic acid.

In another embodiment, the kit further comprises a reagent capable of detecting a protein.

In one embodiment, the reagent is an enzyme capable of specifically recognizing an amino acid sequence of the peptide or protein and cleaving it. In one embodiment, the reagent is an enzyme capable of specifically recognizing an amino acid sequence of the peptide of sequence SEQ ID NO: 1 or a variant thereof and cleaving it, and incapable of recognizing an amino acid sequence of mature or secreted uromodulin and cleaving it. In another embodiment, the reagent is an enzyme selected from the group consisting of an enzyme capable of specifically recognizing an amino acid sequence of mature or secreted uromodulin or of a variant thereof and cleaving it, an enzyme capable of specifically recognizing an amino acid sequence of albumin or of a variant thereof and cleaving it, an enzyme capable of specifically recognizing an amino acid sequence of IgA or of a variant thereof and cleaving it, an enzyme capable of specifically recognizing an amino acid sequence of IgG or of a variant thereof and cleaving it, and combinations thereof.

In one embodiment, the reagent is an aptamer. In one embodiment, the reagent is an aptamer capable of specifically detecting a peptide of sequence SEQ ID NO: 1 or a variant thereof, and incapable of detecting mature or secreted uromodulin, or a fragment of said aptamer with the capacity to bind to sequence SEQ ID NO: 1 or to a variant thereof. In another embodiment, the reagent is an aptamer selected from the group consisting of an aptamer capable of specifically recognizing mature or secreted uromodulin or a variant thereof, an aptamer capable of specifically recognizing albumin or a variant thereof, an aptamer capable of specifically recognizing IgA or a variant thereof, an aptamer capable of specifically recognizing IgG or a variant thereof, and combinations thereof. Methods for producing such aptamers are well known in the art.

In an even more preferred embodiment, the reagent is an antibody. In an even more preferred embodiment, the antibody is an antibody capable of specifically detecting a peptide of sequence SEQ ID NO: 1 or a variant thereof, and incapable of detecting mature or secreted uromodulin, or a fragment of said antibody with the capacity to bind to sequence SEQ ID NO: 1 or to a variant thereof. In another embodiment, the antibody is an antibody selected from the group consisting of an antibody capable of specifically recognizing mature or secreted uromodulin or a variant thereof, an antibody capable of specifically recognizing albumin or a variant thereof, an antibody capable of specifically recognizing IgA or a variant thereof, an antibody capable of specifically recognizing IgG or a variant thereof, and combinations thereof. Methods for producing such antibodies are well known in the art.

As it is used herein, the term "specifically detecting" or "specifically recognizing" refers to said reagent only recognizing that peptide or protein of interest and does not show any reaction if said peptide or protein of interest is not present. When reference is made to a peptide or protein, it refers to the reagent being capable of reacting with at least one epitope of the peptide or the protein, in contrast with non-specific interaction.

As one skilled in the art will understand, the antibodies of the kit of the invention can be used in all the known techniques for determining the levels of protein which are suitable for analyzing a sample, such as Western blot, ELISA, RIA, competitive EIA, DAS-ELISA, immunocytochemical or immunohistochemical techniques, techniques based on the use of biochips, protein microarrays, colloidal precipitation assays in test strips, etc.

The antibodies and aptamers can be fixed to a solid support such as a membrane, a plastic, or a glass, optionally treated to make fixing of said antibodies and aptamers to the support easier. Said solid support comprises at least one set of antibodies or aptamers which recognize the levels of a peptide of sequence SEQ ID NO: 1, or mature or secreted uromodulin, or albumin, or IgA, or IgG, or a variant thereof, and which can be used for detecting the expression levels of these proteins.

The kits of the invention further comprise reagents for detecting a protein encoded by a constitutive gene. The availability of said additional reagents allows normalizing the measurements taken in different samples (for example, the sample to be analyzed and the control sample) in order to rule out that the differences in the expression of the biomarkers are due more to a difference in the total amount of proteins in the sample than to actual differences in the relative expression levels. The constitutive genes in the present invention are genes that are always active or are constantly transcribed, and encode proteins that are constitutively expressed and carry out essential cell functions. Proteins which are constitutively expressed and can be used in the present invention include, without limitation, β-2-microglobulin (B2M), ubiquitin, 18S ribosomal protein, cyclophilin, GAPDH, PSMB4, tubulin, and actin.

In another embodiment, the kit further comprises a reagent capable of detecting a lipid. Non-limiting examples of reagents capable of detecting a lipid are, without limitation, reagents for luxol fast blue staining, Baker's acid hematin technique, oil red 0 staining, Sudan black B staining, Sudan II, III and IV.

In another embodiment, the kit further comprises a reagent capable of detecting a sulfated GAG. Non-limiting examples of reagents capable of detecting a sulfated GAG are, without limitation, DMB, Alcian Blue, acid albumin, and cetylpyridinium chloride (CPC). In a preferred embodiment, the reagent capable of detecting a sulfated GAG is DMB, preferably 0.02% DMB in water.

In another embodiment, the kit further comprises a computer program for executing a method according to any of the inventive aspects described in this invention.

In another aspect, the invention relates to a kit comprising an antibody capable of specifically detecting a peptide of sequence SEQ ID NO: 1 or a variant thereof, and incapable of detecting mature or secreted uromodulin, or a fragment of said antibody with the capacity to bind to sequence SEQ ID NO: 1 or to a variant thereof.

In another aspect, the invention relates to a kit comprising an aptamer capable of specifically detecting a peptide of sequence SEQ ID NO: 1 or a variant thereof, and incapable of detecting mature or secreted uromodulin, or a fragment of said aptamer with the capacity to bind to sequence SEQ ID NO: 1 or to a variant thereof.

In another aspect, the invention relates to a kit comprising an enzyme capable of specifically recognizing an amino acid sequence of the signal peptide of SEQ ID NO: 1 of uromodulin or of a variant thereof and cleaving said peptide, and incapable of recognizing an amino acid sequence of mature or secreted uromodulin and cleaving it.

All the particular embodiments of the methods of the present invention are applicable to the kits of the invention and to uses thereof.

Uses of the Kits of the Invention

In another aspect, the invention relates to the use of a kit as defined above for separating the free sulfated GAGs and the fraction bound to or associated with sulfated GAGs from a sample, for identifying the profile of proteins bound to or associated with sulfated GAGs of a sample, for identifying the profile of lipids bound to or associated with sulfated GAGs of a sample, for detecting an alteration in the pattern of glycosylation by sulfated GAGs, for diagnosing a disease, for determining the prognosis of a disease, for monitoring the progression of a disease, for monitoring the effect of a therapy for the treatment of a disease, for predicting the response to a therapy, for designing a personalized therapy, for identifying compounds suitable for the treatment of a disease, for identifying protein or lipid biomarkers bound to or associated with the sulfated, or for detecting complexes formed by exosomes, sulfated GAGs, and a protein.

In a preferred embodiment, the disease is a disease associated with an alteration of one or more sulfated GAGs; preferably the alteration is an increase or a decrease in one or more sulfated GAGs.

In another embodiment, the disease is selected from the group consisting of mucopolysaccharidosis and a kidney disease. More preferably, the kidney disease is autosomal dominant polycystic kidney disease type 1 or type 2.

All the particular embodiments of the methods of the present invention are applicable to the kits of the invention and to uses thereof.

The invention is described in detail below by means of the following examples, which must be interpreted as being merely illustrative and non-limiting of the scope of the invention.

EXAMPLES

Example 1: Description of Sample Processing Before the Isolation of the Fraction Associated with Glycosaminoglycans and/or Exosomes In the case of urine, the process started with the second morning urine (discarding the first stream to prevent contaminations of the external genitourinary system) collected in protease-free containers, and urine with the visible presence of hematuria and urinary tract infection were discarded. The urine samples must be stored at −20° C. until use if they are not used on the same day.

In the case of blood samples, they must be collected in a suitable tube depending on whether serum or plasma is to be obtained. In the case of plasma, the blood sample must be collected in a tube with anticoagulant, for example heparin or EDTA, and centrifuged at a maximum speed for 10 minutes. In the case of serum, the sample must be collected in an STII or biochemical tube, left to sit for at least 30 minutes, and centrifuged at a maximum speed for 10 minutes. Both the plasma and the serum must be stored at −80° C. until use if they are not used on the same day.

Example 2: Description of the Exosome Isolation Method

The samples were processed following a modification of the method that is well established in the literature (Christianson et al., Proc Natl Acad Sci USA 2013, 110:17380-5; Hogan et al., J Am Soc Nephrol 2009, 20:278-288). In the case of urine, the method started with the urine supernatant obtained by means of centrifuging urine at 1000 g for 5 minutes. Briefly, the urine supernatants were centrifuged at 5,000 g for 20 minutes, subjected to filtration through low protein adsorption filters having a pore size of 0.22 μm, and ultracentrifuged at 100,000 g for 2 hours. The exosome pellets were resuspended in a suitable volume of buffer (for example, PBS 1×) and kept at −20° C. until use.

Example 3: Description of the Separation Method for Separating the Fraction Bound to Glycosaminoglycans Dimethylmethylene blue (Serva) at a concentration of 0.29 mM dissolved in ethanol was used, and 0.2 M formate buffer pH 3.5 was added at a 1:99 ratio. It was then mixed with the biological sample at a 1:2 ratio. It was subsequently incubated for 15 minutes at room temperature. Finally, it was centrifuged at 10,000 g for 10 minutes at 4° C. The supernatant was removed and the precipitate containing the fraction bound to glycosaminoglycans was recovered.

Example 4: Identification of Proteins Bound to Glycosaminoglycans in Urine Samples The presence of two known proteins which are glycated by up to 30%, i.e., albumin and uromodulin, in urine samples were identified by means of proteomics (identification by means of MALDI-TOF/TOF sequencing).

Figure 4:
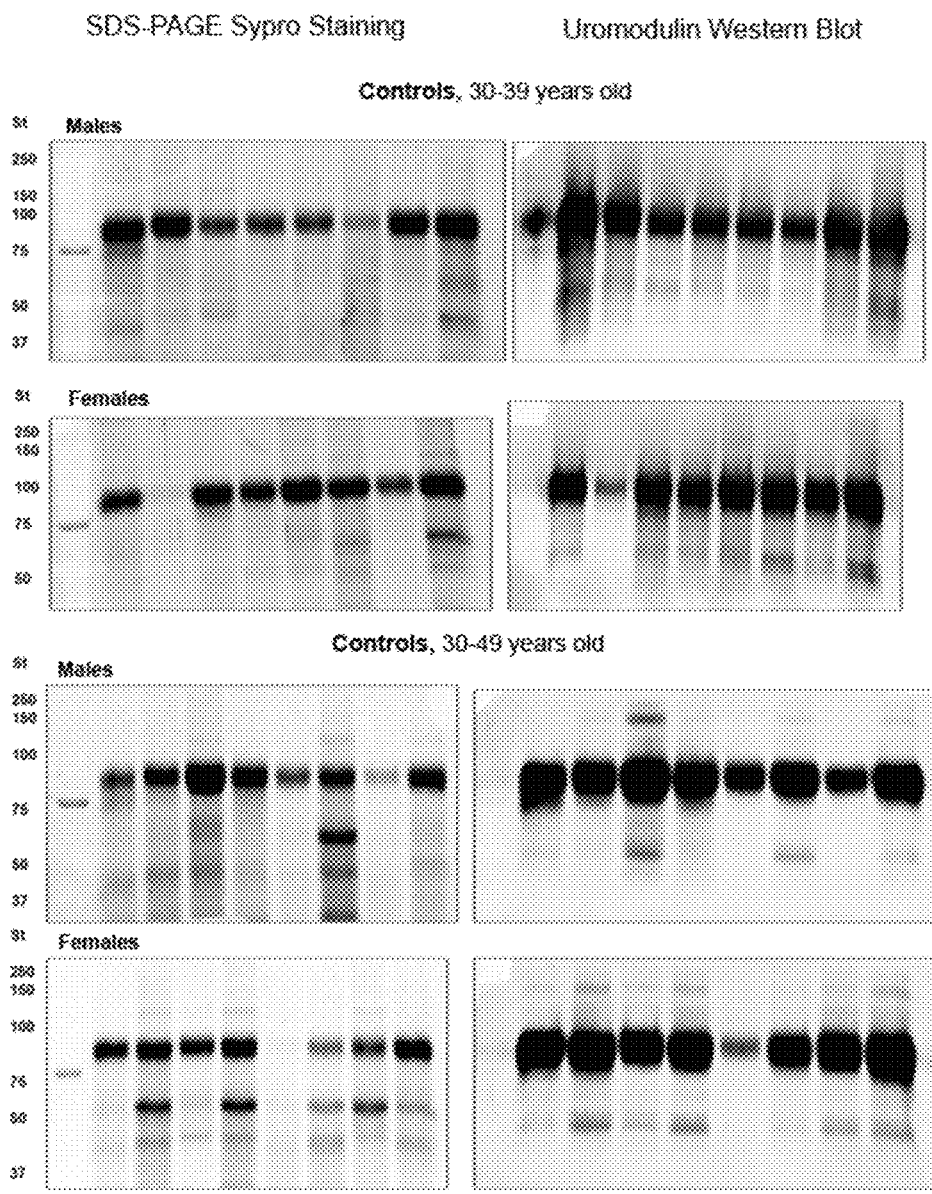
FIG. 4: SDS-PAGE depicting the pattern of GAG-bound protein bands in the urine of control individuals (16 males and 16 females, 30-49 years of age), and the identification of uromodulin by means of Western blot.

FIG. 4 shows the pattern of GAG-bound protein bands in the urine (50 μl) of healthy individuals (16 males and 16 females, 20 to 49 years of age) using the method of the invention. The most abundant GAG-bound protein in control individuals is uromodulin, as shown on the left part of the drawing, and other proteins are present to a lesser extent. Standard Western blot protocols and a uromodulin-specific antibody (Biomedical-BTI) in a dilution of 1:3000 were used for identifying uromodulin. It was viewed using FITC (Abcam IgG-FITC, dilution 1:1000) and the Molecular Imager system (Bio-Rad) with Quantity One software (Bio-Rad).

Figure 5:
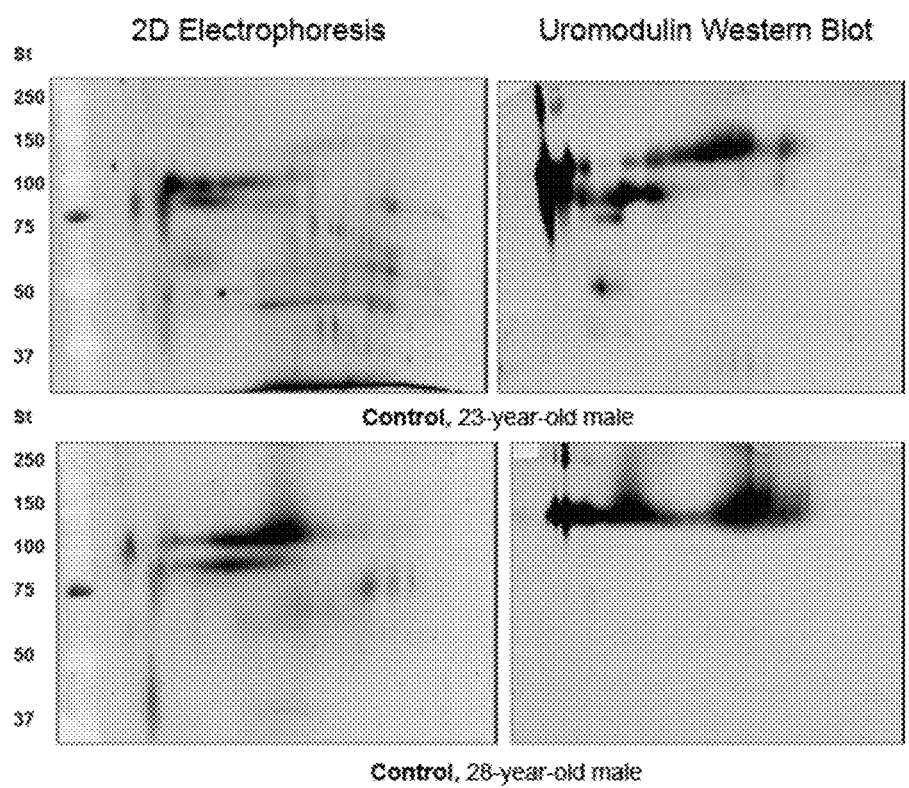
FIG. 5: Two-dimensional electrophoresis (strips of pH 3-6 and 7.5% PAGE gels) of the urine precipitated with DMB in two individual male controls, and the identification of uromodulin by means of Western blot.

In order to better separate proteins that were bound to GAG in the urine, 2D electrophoresis which allows seeing different isoforms of the same protein was used. After several tests, it was observed that there were no proteins present in urine precipitated with DMB above pH 6. FIG. 5 shows the GAG-bound protein pattern in the urine (300 μl) of two control individuals (23- and 26-year-old males) using strips of pH 3-6 and 7.5% SDS-PAGE, followed by staining with Sypro Ruby. The presence of several spots was observed, where the most abundant ones are the different isoforms of uromodulin. Western blot was performed as described above.

Figure 6:
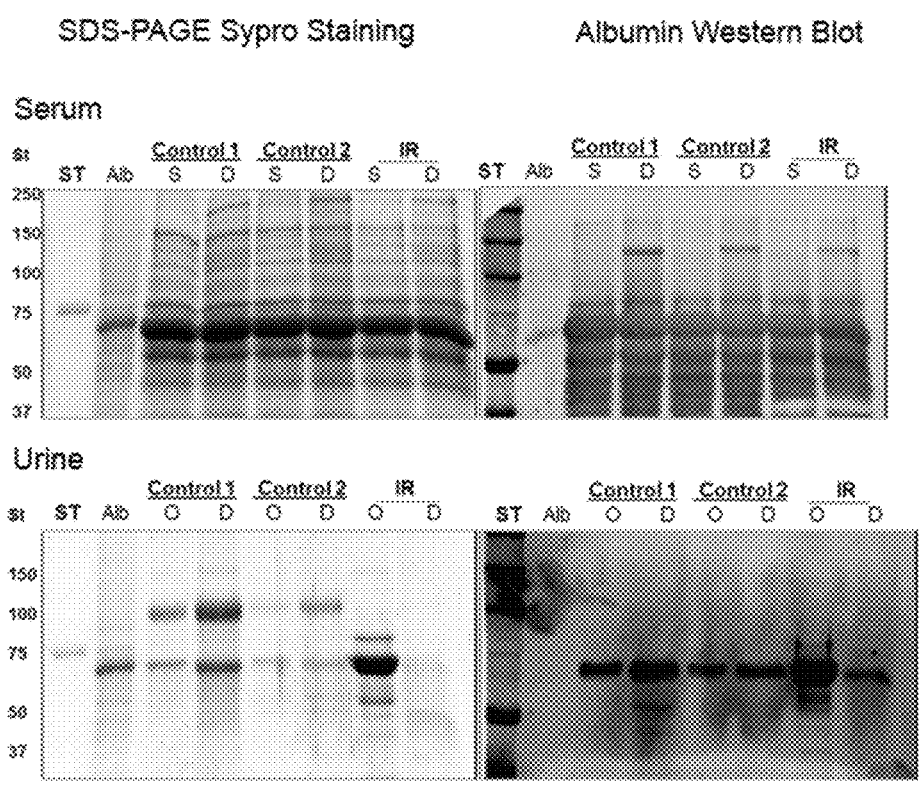
FIG. 6: The pattern of the total protein bands and the protein bands in the fraction bound to GAG in the urine and serum of control individuals with kidney failure (left). Identification of the GAG-bound albumin present by means of Western blot. IR, individuals with kidney failure; ST, molecular weight marker; Alb, albumin; S, unprecipitated serum; 0, unprecipitated urine; D, serum or urine precipitated with DMB.

FIG. 6 shows the application of the invention in the search for different GAG-bound protein patterns in the urine and serum of control individuals and individuals with kidney failure (left), and the identification of GAG-bound albumin present by means of Western blot (right). For the serum sample, a 1:100 dilution in PBS was made and 50 μl were precipitated with DMB following the method of the invention described above. For albumin Western blot, an antibody from Origene at a 1:4000 dilution was used, and it was viewed with a Cy5-bound antibody (IgG-Cy5 Abcam, dilution 1:5000) using the equipment described above. It was observed that the patient with kidney failure had almost no uromodulin in the urine, but had a lot of albumin, although only a small amount was glycated.

Example 5: Description of the Assays for Reconstituting the Binding Between Different Proteins and Glycosaminoglycans FIG. 7 demonstrates that the method of the invention is capable of separating those proteins having glycosaminoglycans bound thereto.

To demonstrate this, commercial uromodulin (Human Tamm Horsfall Glycoprotein, Biomedical-BTI) and albumin (Bio-Rad) were used, said compounds being incubated with commercial glycosaminoglycans (heparan, chondroitin and dermatan sulfate from Sigma) both in PBS (FIGS. 7c and 7d) and in the urine (FIGS. 7a and 7b) of a patient with a truncating mutation (C255Y) in the uromodulin gene which entails virtually undetectable levels of uromodulin in the urine, and with an ongoing autosomal dominant medullary cystic disease (ADMCKD). One microgram of bovine serum albumin (BSA) (Bio-Rad) or uromodulin (Biomedical-BTI) in PBS was incubated with 100 μg of commercial GAGs for 1 hour at 37° C. to allow the binding of GAGs to proteins. Dimethylmethylene blue was then added and the separation method for separating the fraction bound to GAG described above was followed.

The precipitate was resuspended in 7.5% SDS and prepared following the standard protocol for the use of SDS-PAGE. It was observed that the commercial albumin and uromodulin are slightly glycated, and after incubation with GAGs, glycation occurs and new protein bands appear.

The experiment was repeated using 20 µl of urine of a patient without uromodulin, the absence of uromodulin and the presence of albumin (FIGS. 7a and 7b, lane 1), both of which were slightly glycated with GAGs (FIGS. 7a and 7b, lane 2), being observed. After incubating the urine with commercial GAGs (100 µg) and with BSA and uromodulin (1 µg), the appearance of new GAG-bound bands was observed. It can be seen in the images of the gels that a superposition of bands occurs between uromodulin and albumin. It has been proven that albumin has a greater affinity for GAGs and is concealing the discovery of other proteins, so the use of albumin depletion methods to try to unmask other proteins would be useful.

Figure 8:
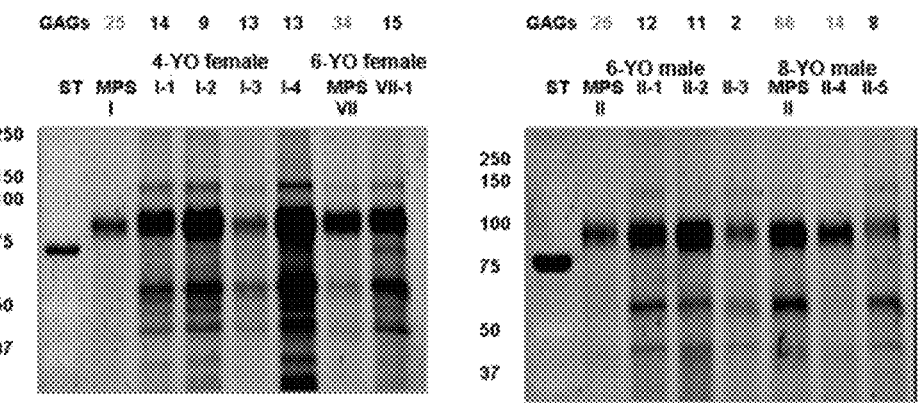
FIG. 8: The pattern of glycosaminoglycan-bound protein bands in the urine of patients with mucopolysaccharidosis (MPS) and their respective controls (sex and age similar to the patients), as well as the identification of uromodulin and albumin by means of Western blot. A) MPS I, 4-year-old female patient with MPS I; I-1, I-2, I-3, and I-4, healthy controls of the same age and sex as the patient with MPS I; MPS VII, 6-year-old female patient with MPS VII; VII-1, healthy control of the same age and sex as the patient with MPS VII. MPS II, 6- and 8-year-old male patients with MPS-II; II-1, II-2, II-3, II-4, II-5, healthy controls of the same age and sex as the patients with MPS-II. B). MPS III, 1- and 10-year-old male patients with MPS III, respectively; III-1, III-2, III-3, III-4, III-5, and III-6, healthy controls of the same age and sex as the patients with MPS III. MPS IV, 17-year-old female patient, and two 14-year-old male patients with MPS IV, respectively; IV-1, IV-2, IV-3, and IV-4, healthy controls of the same age and sex as the patients with MPS IV. The total levels of glycosaminoglycan (mg/mmol creatinine) measured by the conventional method with DMB are shown in the top part, the values that are higher than the reference value are shown in grey, and normal values are shown in black. ST, molecular weight marker.
Figure 8:
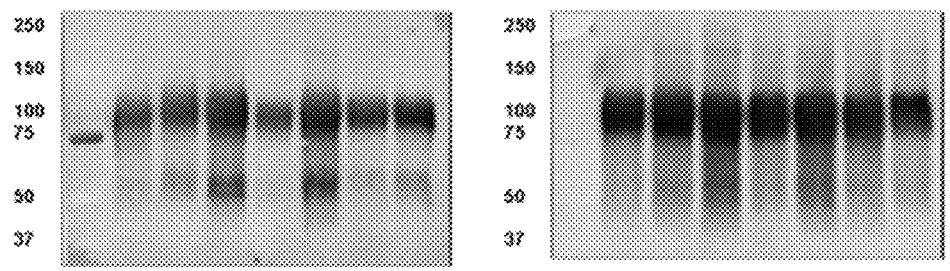
Figure 8:
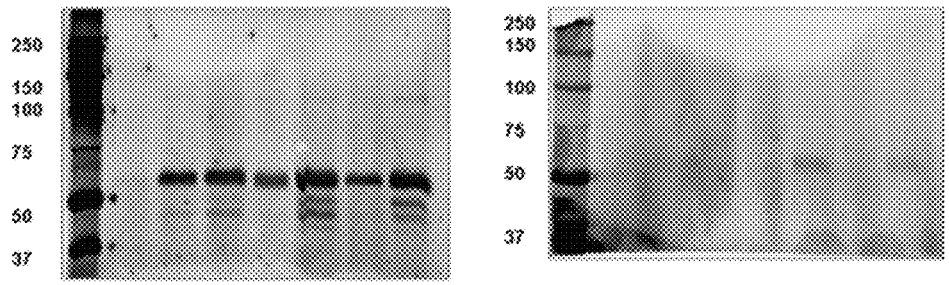
Figure 8:
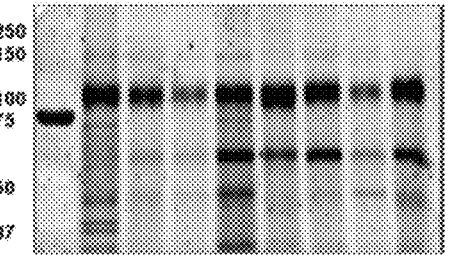
Figure 8:
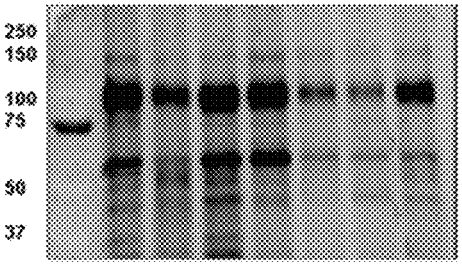
Figure 8:
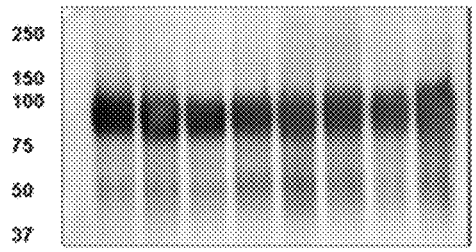
Figure 8:
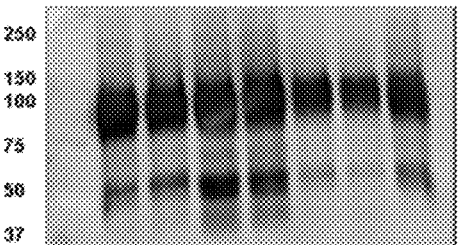
Figure 8:
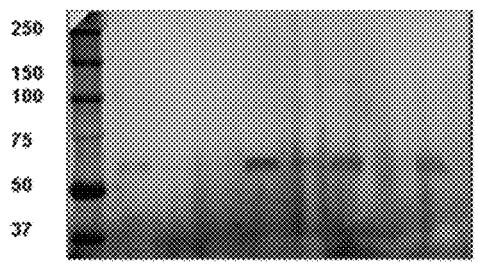
Figure 8:
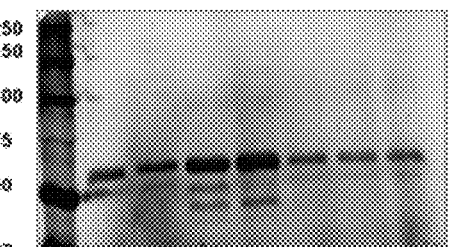

Example 6: Identification of the Patterns of Specific GAG-Bound Protein Bands in Individuals Suffering from Mucopolysaccharidosis FIG. 8 shows the patterns of GAG-bound protein bands in the urine of patients suffering from different types of mucopolysaccharidoses (MPS I, MPS II, MPS III, MPS IV, and MPS VII) and in control individuals of the same age and sex as the patients. The levels of GAG in urine (above the reference level in patients) measured by the conventional method with DMB (Whitley C. B et al., Clin. Chem. 1989, 35:2074-2081), and the identification of the proteins, uromodulin and albumin, by means of Western blot performed under the conditions already described above, are also shown.

Figure 9:
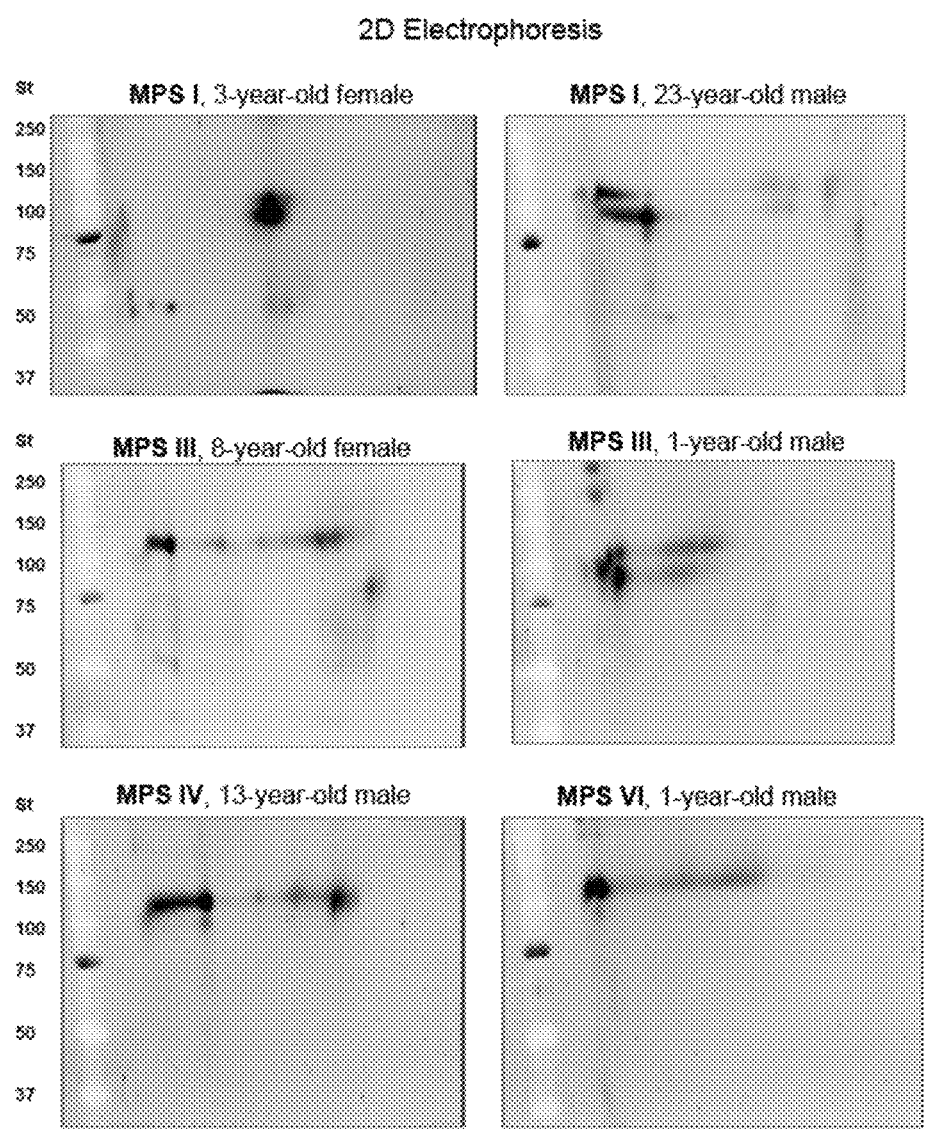
FIG. 9: Two-dimensional electrophoresis (strips of pH 3-6 and 7.5% SDS-PAGE gel) of the urine precipitated with DMB of patients with MPS.

FIG. 9 shows the 2D electrophoresis under the conditions described above in the urine of patients with confirmed mucopolysaccharidosis. When compared to the controls of FIG. 5, the disappearance of high molecular weight isoforms corresponding to low-weight glycated proteins and uromodulin is observed.

Example 7: Mucopolysaccharidosis Diagnostic Biomarker

Upon conducting uromodulin sequencing studies by means of MALDI-TOF/TOF, it was found that the signal peptide SEQ ID NO: 1 (MGQPSLTWML MVVVASWFIT TAAT) is maintained in patients with mucopolysaccharidosis, the peptide of SEQ ID NO: 2 (MGQPSLTWML MVVVASWFIT TAATDTSEAR), which is absent in the samples from control individuals, specifically being detected. Therefore, it would be possible to use tandem mass spectrometry technology for quantifying this signal peptide of uromodulin and to use it as a diagnostic marker for MPS.

Example 8: Diagnosis of Kidney Disease, Follow-Up of Kidney Disease and the Search for New Biomarkers for a Kidney Disease The invention was used in the study of patients or future patients with autosomal dominant polycystic kidney disease associated with known mutations in genes PKD1 (chr16: 41711del18 bp; chr16:28907c>g; chr16:37060c>t) and PKD2 (chr4:88995974c>t). Twenty-three patients with PKD1, 10 patients with PKD2, and 17 healthy volunteers whose diagnoses and kidney functions were assessed by nephrology experts were studied. The kidney disease was diagnosed based on the levels of serum creatinine, as well as the measurement of other pre-established renal parameters that are routine in clinical practice and genetic diagnosis. The normal kidney function of healthy volunteers was assessed through serum creatinine and anamnesis.

The supernatants and pellets obtained from fractionation by centrifugation were subjected to specific precipitation with DMB at a 1:2 ratio as described, and the precipitates were resuspended and denatured at 95° C. for 5 minutes in Laemli buffer with β-mercaptoethanol and 7.5% SDS at a 1:1 ratio. Between 15-30 µl were loaded in a 7.5% SDS-PAGE gel, and the proteins were separated at 100 V for about 1 hour 30 minutes and viewed by means of staining with protein contrast agents (for example, Sypro Ruby Protein-Gel Stain 1×).

Figure 10:
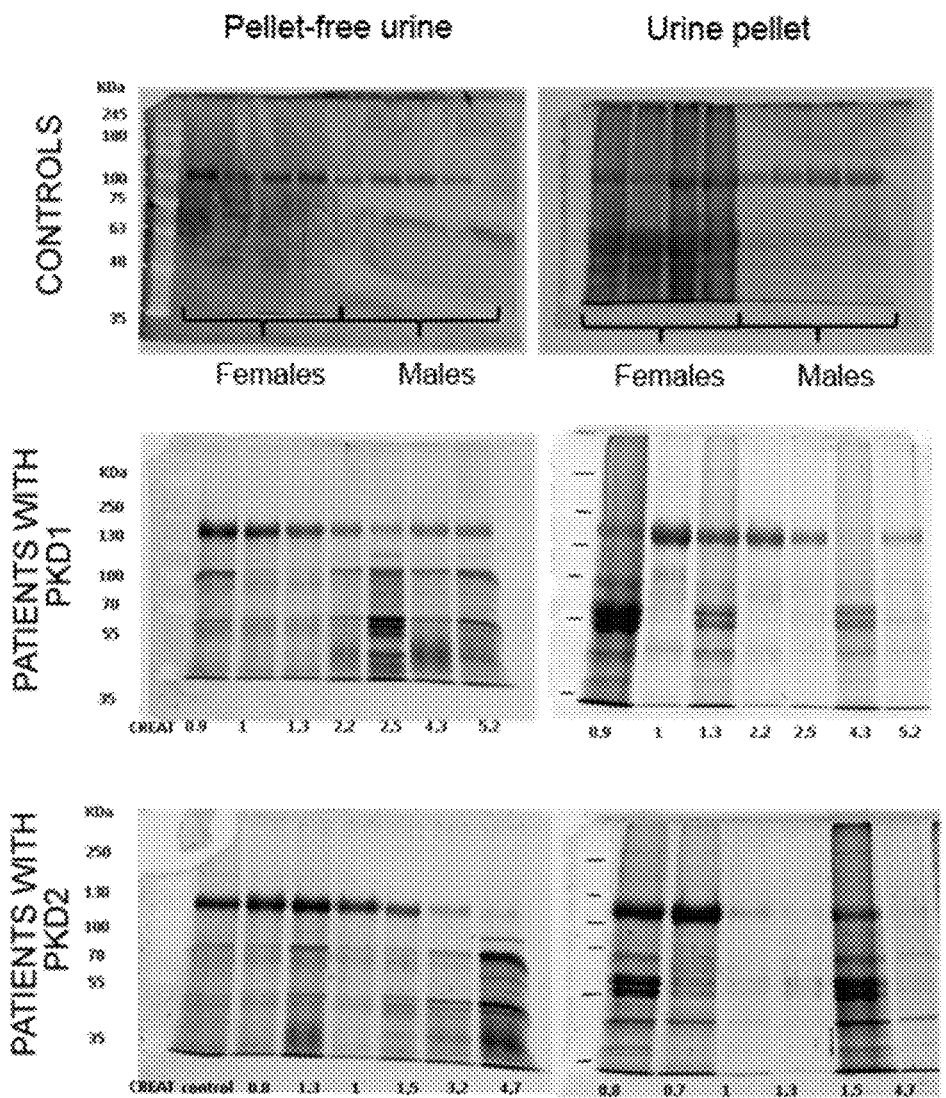
FIG. 10: The GAG-associated protein profile in the urine of control individuals, patients with PKD type 1 and patients with PKD type 2. The first column represents the molecular weight markers. The following seven columns show the uromodulin precipitated with GAG after incubation with DMB and denaturation (30 μl of precipitated protein are loaded per column) in samples of different patients with PKD1 or PKD2. Creat, creatinine.

FIG. 10 shows that there is a profile of proteins associated with GAGs in control individuals, and that the GAG-bound urine protein profile is altered in patients with kidney disease, for example PKD, and that this alteration depends on their kidney function (determined by the levels of serum creatinine and proteinuria). Future patients who have a known mutation and do not exhibit any symptom at the time of the assays already show a deficiency in the complex. This observation discloses the use thereof as a diagnostic and prognostic biomarker for a kidney disease and kidney damage, where changes in the levels of creatinine are anticipated several years in advance.

Figure 11:
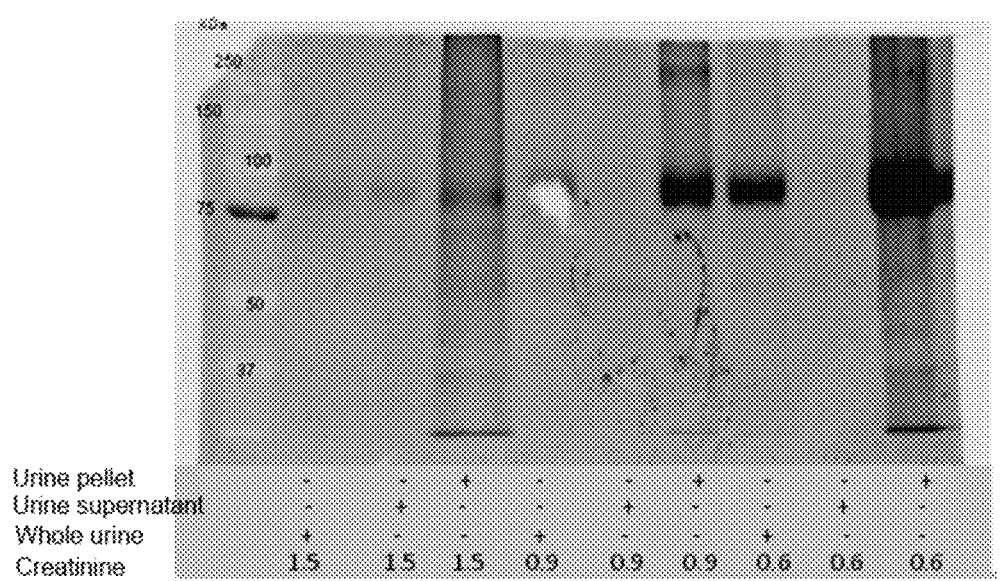
FIG. 11: Differences observed in the GAG-bound protein profile between the urine supernatants and their respective cell pellets as the kidney function gradually deteriorates.

On a protein level, this urinary fingerprint seems to be associated with uromodulin and GAGs (it has been proven for chondroitin, dermatan and heparan sulfate) known to be part of the glomerular basement membrane of the extracellular matrix, and the mucopolysaccharide layer of the uroepithelial surface. Uromodulin seems to have an inverse expression pattern with respect to the levels of creatinine, where tends to drop progressively in patients with advanced kidney disease. In this manner, it has been observed that the greater the damage and progression of kidney failure, even without significant changes in the levels of creatinine, the lower the presence of uromodulin associated with GAGs in urine (FIGS. 10 and 11). This alteration is more obvious in patients with PKD type 2 (mutated PKD2 gene) than in patients with PKD type 1 (mutated PKD1 gene), where GAG-associated uromodulin practically disappear at high levels of creatinine, whereas other proteins associated with GAGs gradually appear (FIG. 10).

By comparing the profiles observed between the supernatants and their respective cell pellets (FIG. 11), it can be determined that, as the chronic kidney failure becomes more severe, fewer proteins associated with GAGs are observed at the intracellular level and more proteins associated with GAGs appear at the extracellular level.

A similar study but on a smaller-scale was performed in plasma from 14 cancer patients (9 with prostate cancer and 5 with colon cancer), as well as in the urine and sera from 14 other patients with suitably validated kidney disease (10 with glomerular diseases and 4 with IgA nephropathy), in peritoneal fluids from 9 kidney patients in renal replacement therapy (peritoneal dialysis), and in the urine of three animal models with ADPKD and ARPKD. Results similar to the first study were obtained, an alteration of the GAG-associated protein profile being observed compared to the homogeneity observed in the samples of the respective controls. Precipitation of proteins associated with GAGs in culture media of different kidney cell lines was also observed. Therefore, the application of this GAG-associated protein fingerprint as a diagnostic/prognostic biomarker extends to any disease with or without kidney involvement and in different types of biological samples.

Example 9: Description of the Conditions for Identifying Uromodulin Associated with Glycosaminoglycans and Exosomes by Means of Western Blot The identification and characterization of purified exosome complexes was performed by means of electron microscopy imaging techniques, validation of the overall size/charge (based on the zeta potential), specific precipitation with DMB as described above, separation in 7.5% SDS-PAGE gels, and Western blot.

The purified exosome fractions, supernatants, and/or urine pellets were precipitated with DMB, processed, and separated in an SDS-PAGE gel as described above. The proteins were transferred to a PVDF-FL membrane at 100 V for an hour and a half, non-specific binding was blocked with 1% casein or 4% skim milk; they were incubated with the primary antibody (rabbit anti-human Tamm Horsfall glycoprotein, Biomedical-BTI) in a 1:3000 dilution, and finally developed by means of incubation with the suitable fluorescent agent-labeled secondary antibody.

Figure 12:
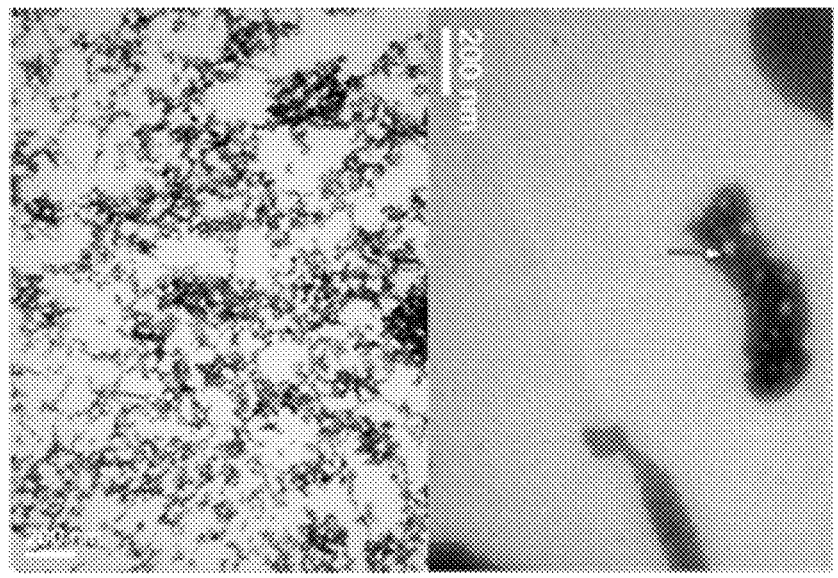
FIG. 12: The identification and characterization of the UMOD-GAG-exosome (UGE) complexes by means of electron microscopy images (a), size (b), zeta potential (c) and Western blot (d) of exosomes purified and precipitated with DMB, where 30 μl of precipitated protein are loaded per column. The first 3 columns of FIG. 12(d) belong to exosomes purified by ultracentrifugation, and columns 4 and 5 belong to exosomes purified by means of gradient with a commercial kit (ExoQuick_TC, System Biosciences). ID, patient code, Creat, creatinine; Pel, urine cell pellet of a healthy volunteer; Ur, urine supernatant of a healthy volunteer; C−, urine supernatant of an individual with ADMCKD (autosomal dominant medullary cystic kidney disease with known mutation in the uromodulin gene); C+, positive control with 1 μg of commercial uromodulin (Human Tamm Horsfall Glycoprotein, Biomedical-BTI).
Figure 12:
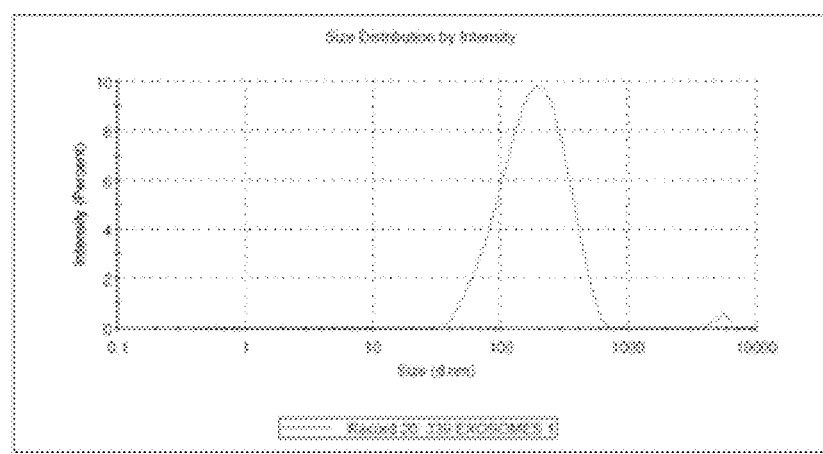
Figure 12:
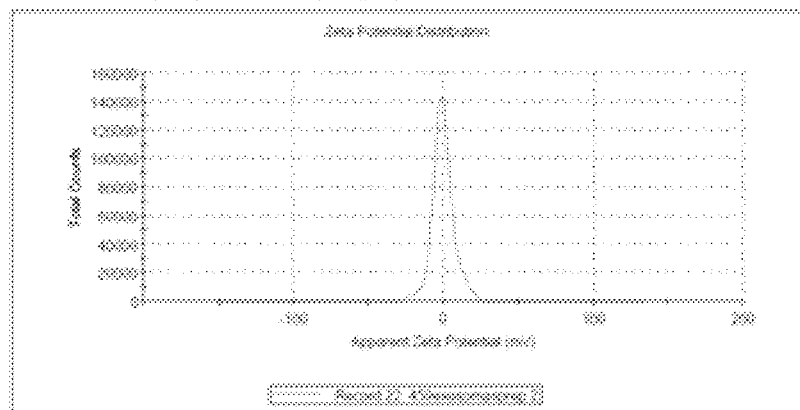
Figure 12:
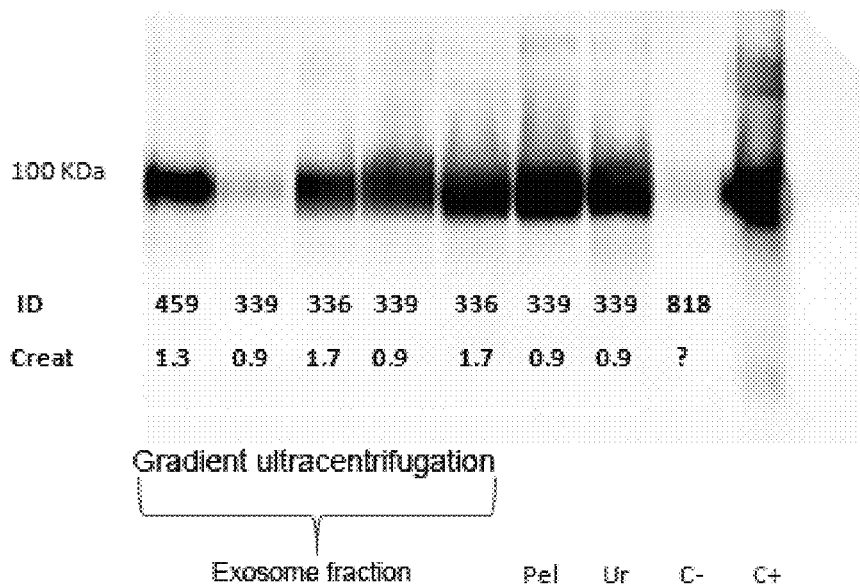

FIG. 12 shows the characterization of the UGE (uromodulin-GAG-exosome) complexes by means of electron microscopy images (a), size (b), zeta potential (c) and uromodulin Western blot (d).

FIG. 12(d) shows the identification of uromodulin associated with the exosome fractions purified using different approaches and in different patients with PKD, as well as in unfractionated cell and urine pellets.

Figure 13:
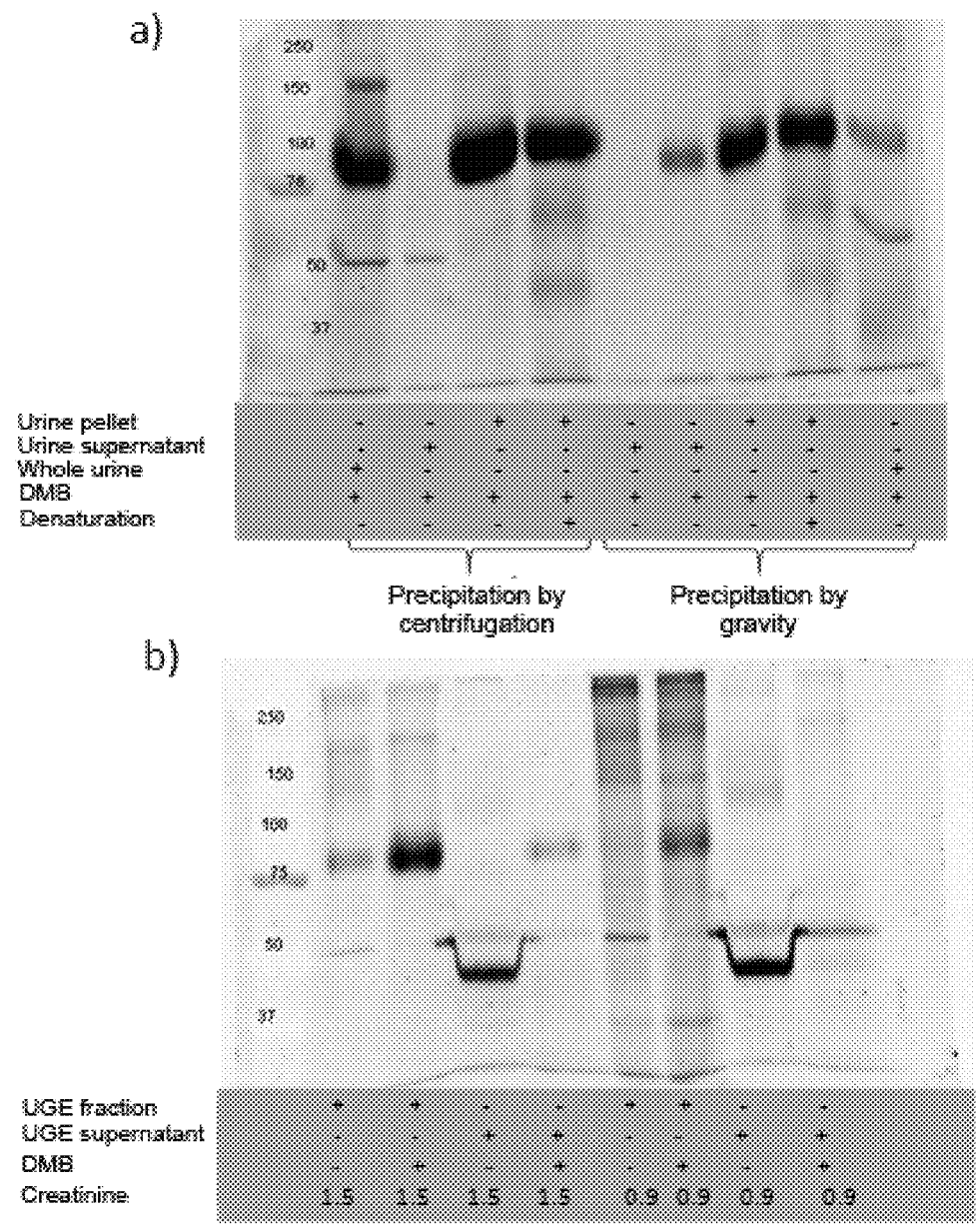
FIG. 13: The purification of UGE complexes by means of various approaches such as precipitation by centrifugation or gravity (a) and gradient isolation (b)

A commercial kit (ExoQuick_CT, System Biosciences) was also used for obtaining exosomes following the manufacturer's instructions (FIG. 13).

Example 10. Description of the Assays for Disrupting the Binding Between Different Proteins, Glycosaminoglycans, and Exosomes The specificity of exosome complexes was validated by means of disrupting and reconstituting the binding between their components, UMOD-exosome-GAG in different media (for example, urine or PBS buffer) and using different approaches (for example, precipitation by gravity, gradient purification, treatment with dithiothreitol, filtration, or incubation with commercial glycosaminoglycans).

Exosomes previously purified from the urine of different patients with PKD by means of gradient purification (ExoQuick_CT, System Biosciences) were used.

Figure 14:
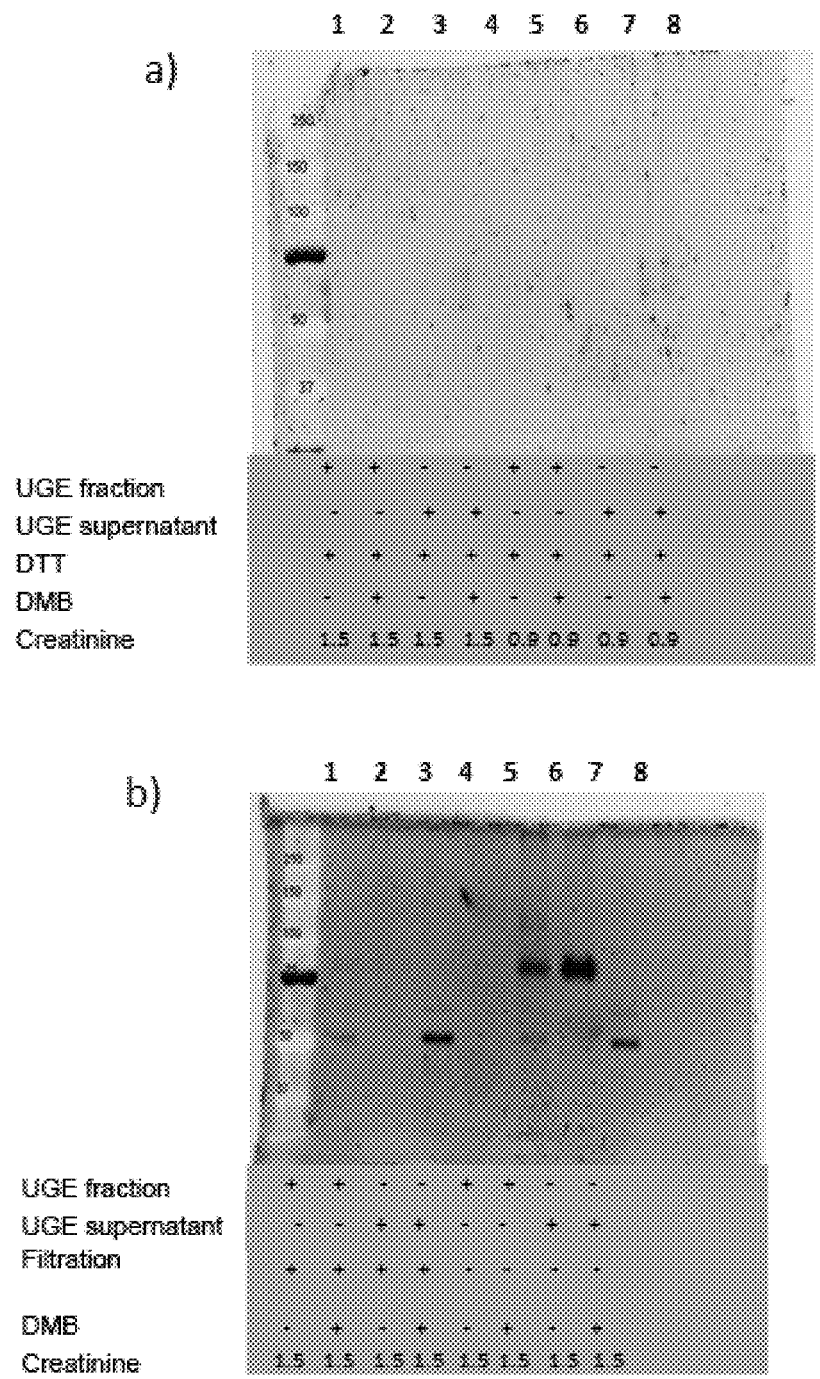
FIG. 14: UGE complex disruption assays by means of treatment with DTT (a) and/or filtration (b and c). a) Lanes 1 and 5, purified exosomes not precipitated with DMB; Lanes 2 and 6, purified exosomes precipitated with DMB, Lanes 3 and 7, supernatant of the exosome fractions; Lanes 4 and 8, same supernatants precipitated with DMB. b) Lane 1, purified and filtered exosomes not precipitated with DMB; Lane 2, purified and filtered exosomes precipitated with DMB; Lanes 3 and 4, supernatants of the filtered exosome fractions that are filtered and precipitated with DMB, respectively; Lanes 5 and 6, purified exosomes not precipitated and precipitated with DMB, respectively; Lanes 7 and 8, supernatants of the exosome fractions not precipitated and precipitated with DMB, respectively. c) Lanes 1-4, remaining cell fraction after exosome purification that is precipitated with DMB, treated with DTT, or treated with DTT and precipitated with DMB, respectively; Lane 5, purified and filtered exosomes treated with DTT; Lane 6, purified and filtered exosomes treated with DTT and precipitated with DMB; Lanes 7 and 8, supernatants of the exosome fractions filtered and treated with DTT with or without precipitation with DMB, respectively.
Figure 14:
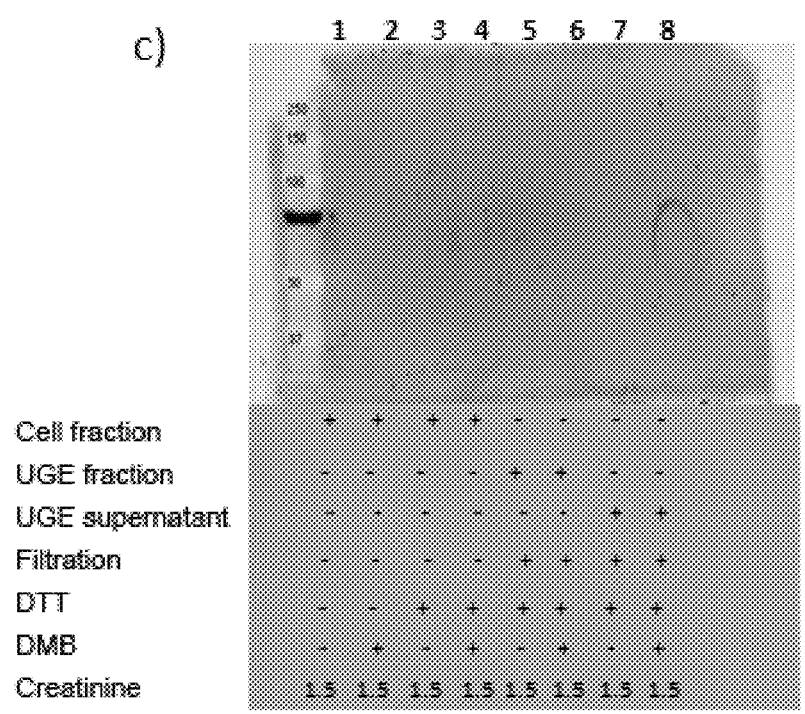

The disruption of UGE complexes was performed by means of treatment with 100 mg/ml of dithiothreitol (DTT) at 37° C. for 10 minutes and/or filtration with low protein adsorption filters having a pore size of 0.22 µm (Millex, Millipore) (FIG. 14).

The functionality of the UMOD-exosome-GAG complexes was tested according to proteomic studies. According to this, several protein bands were cleaved from SDS-PAGE gels and processed for identification by means of MALDI-TOF/TOF sequencing.

The different proteins associated with UGE complexes were identified by means of MALDI-TOF/TOF sequencing, said proteins being described in detail in Table II.

TABLE II

Proteins associated with UGE complexes identified by means of MALDI-TOF/TOF sequencing.

| SDS-PAGE LOCALIZATION | ACCESSION NUMBER | PROTEIN NAME |
| --- | --- | --- |
| 250 KDa | P02768-ALBU_HUMAN | Albumin |
| 250 KDa | P13645-K1C10_HUMAN | Keratin, type I cytoskeletal 10 |
| 250 KDa | P01877-IGHA2_HUMAN | Ig A2 chain C region |
| 250 KDa | P01876-IGHA1_HUMAN | Ig A1 chain C region |
| 250 KDa | P04264-K2C1_HUMAN | Keratin, type II cytoskeletal 1 |
| 180 KDa | P01834-IGKC_HUMAN | Ig Kappa chain C region |
| 80 KDa | P07911-UROM_HUMAN | Uromodulin |
| 60 KDa | P04264-K2C1_HUMAN | Keratin, type II cytoskeletal 1 |
| 50 KDa | P02768-ALBU_HUMAN | Albumin |
| 37 KDa | P02768-ALBU_HUMAN | Albumin |

The exosomes isolated from urine seem to form a complex with uromodulin and GAGs both in samples from healthy volunteers and kidney patients.

It is furthermore demonstrated that the uromodulin-glycosaminoglycan-exosome association is specific (FIG. 13) and that the integrity/functionality of these complexes depends on the suitable presence of their three constitutive elements (FIG. 14).

Figure 15:
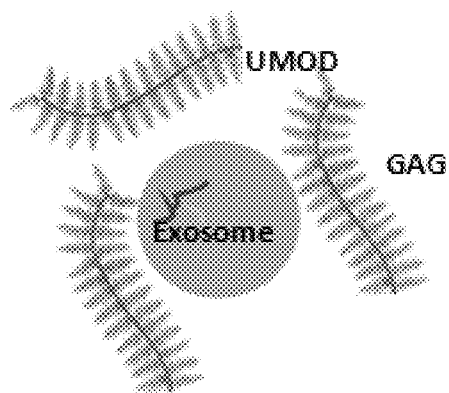
FIG. 15: Schematic depiction of the UGE complexes with the possible associations between the three elements forming them. a) Exosomes associated with GAGs through uromodulin, b) exosomes associated directly with GAGs without needing uromodulin as a bridge.
Figure 15:
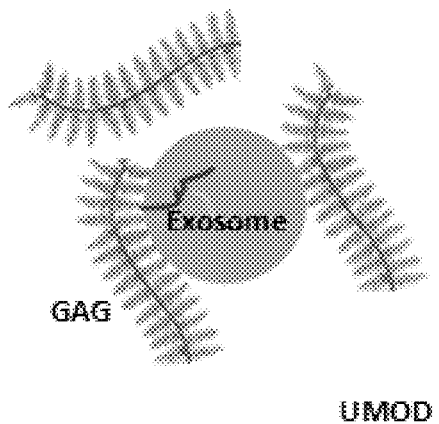

FIG. 15 shows the possible associations between the three elements forming the UGE complexes.

Example 11: UGE Complexes are Lost when the Kidney Damage/Failure Progresses

Figure 16:
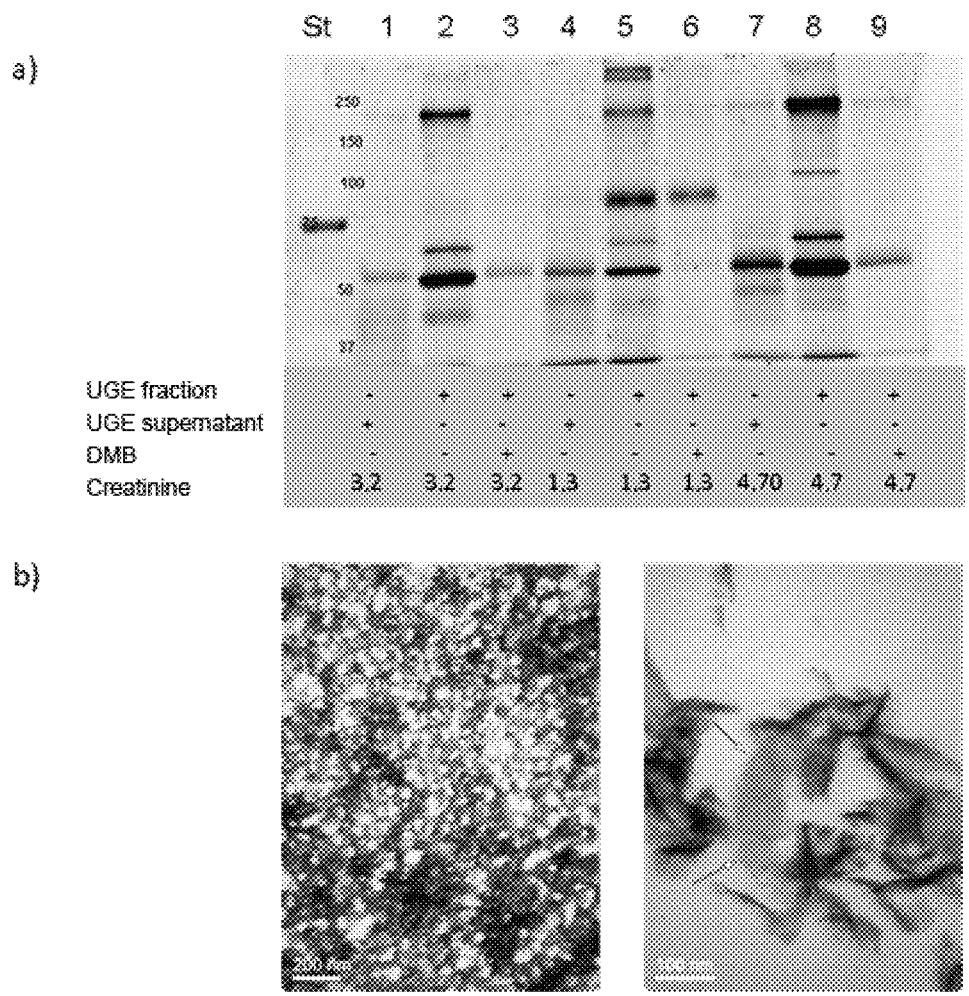
FIG. 16: The UGE complexes disappear as the kidney disease progresses. A gel representative of 3 patients with polycystic kidney disease caused by mutations in the PKD2 gene is shown; a) Lanes 1, 4, and 7, supernatants of the unprecipitated exosome fraction; Lanes 2, 5, and 8, unprecipitated exosome fraction; Lanes 3, 6, and 9, exosome fraction precipitated with DMB; St, molecular weight marker. b) Electron microscopy images of the UGE complexes in an individual with normal kidney function (left) and the absence of UGE complexes in an individual without uromodulin and with kidney damage (right).

Exosomes previously purified from the urine of different patients with a kidney disease, specifically from 6 patients with ADPKD and 3 patients with ADMCKD with the previously indicated mutations were used. FIG. 16 shows how UGE complexes are lost as kidney damage progresses (corresponding with increased levels of creatinine).

Figure 17:
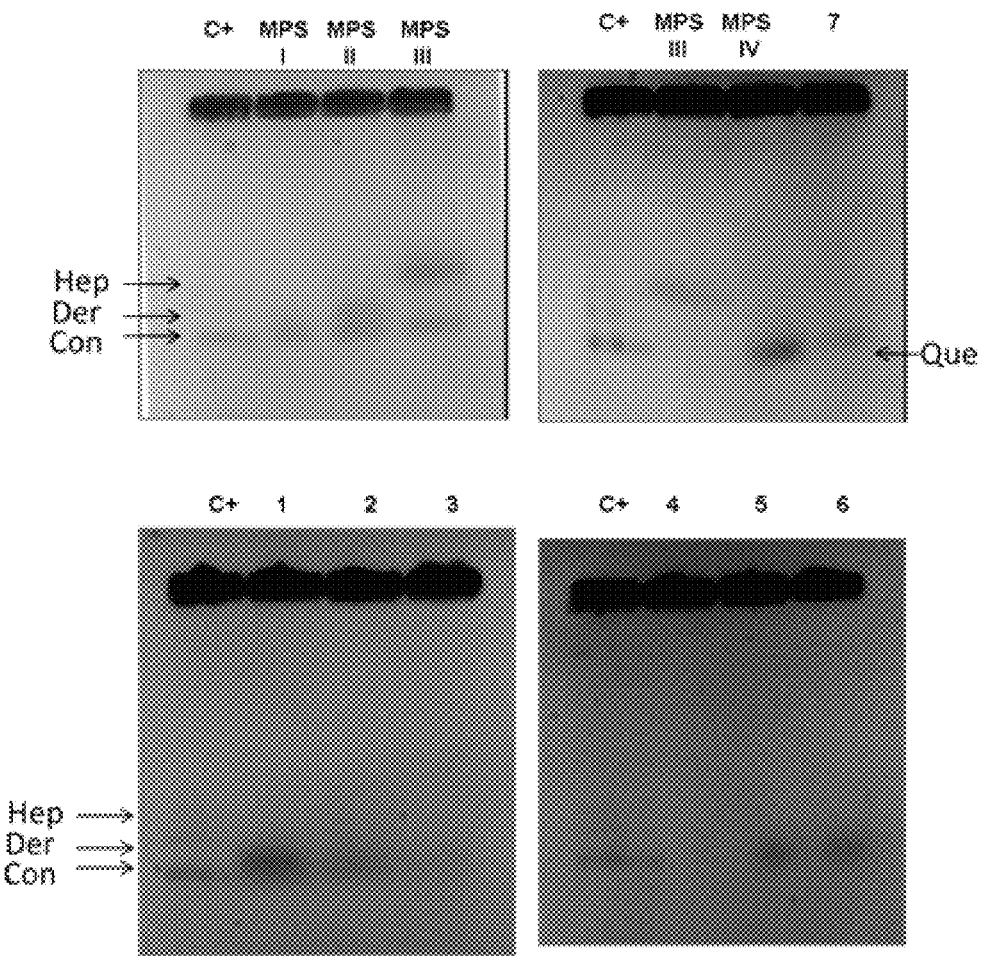
FIG. 17: Separation of the free GAGs in urine precipitated with DMB in cellulose acetate gels. C+, mixture of commercial chondroitin sulfate (Con), dermatan sulfate (Der), and heparan sulfate (Hep) precipitated with DMB; lanes MPS I, MPS II, MPS III, and MPS IV, urine of patients with mucopolysaccharidosis I, II, III, and IV, respectively, precipitated with DMB; lanes 1, 2, 3, 4, 5, 6, and 7, urine of individuals without mucopolysaccharidosis of different ages (1 month old, 7 months old, 1 year old, 3 years old, 4 years old, 6 years old, and 7 years old, respectively) precipitated with DMB, where the only GAG present is chondroitin sulfate. Que, the band corresponding to keratan sulfate characteristic of MPS IV.

Example 12: Separation of Free GAGs in Urine in Cellulose Acetate Gels for the Diagnosis of Mucopolysaccharidosis The inventors have developed a method which allows improving the diagnosis of mucopolysaccharidoses using the separation of free GAGs (chondroitin sulfate, dermatan sulfate, heparan sulfate, and keratan sulfate) in urine samples. To that end, the second morning urine was used, and 0.5 ml of urine were precipitated with 1 ml of 0.29 mM DMB in 0.2 M sodium formate buffer at pH 3.5. It was mixed and left to precipitate for 15 minutes at room temperature. It was then centrifuged for 10 minutes at 13,000 rpm at 4° C., the supernatant was removed by suction or decanting, and the precipitate was resuspended in 50 microliters of 7.5% SDS. A mixture of commercial chondroitin sulfate, dermatan sulfate, and heparan sulfate, which was used as a positive control, was also prepared (C+ in FIG. 17). Four microliters were loaded in a cellulose acetate gel (Cellogel Electrophoresis Co. Srl; Cod. 01A32-25; 5.7×14 cm/200 µm) and 0.05 M fresh barium acetate was used as buffer. For the separation, the gel was run at 150 V for 1 hour and 15 minutes, and then stained with 0.02% DMB in water for 10 minutes under stirring at room temperature. Subsequently, destaining was performed using 10% acetic acid for 10 minutes under stirring at room temperature. As can be seen in FIG. 17, the appearance of defined and separated blue free GAG bands was observed and it allowed differentiating individuals with mucopolysaccharidosis from controls not suffering from any disease. In healthy controls, only the chondroitin sulfate band was observed; however, in sick individuals, depending on the type of mucopolysaccharidoses, the keratan sulfate band characteristic of mucopolysaccharidosis IV, the heparan sulfate band characteristic of mucopolysaccharidosis III, or the dermatan sulfate band characteristic of mucopolysaccharidoses I, II, VI, and VII, were observed.

CONCLUSIONS

The results of FIGS. 8 and 9 show that it is possible to diagnose mucopolysaccharidoses in a simple manner using the method of the invention. On one hand, the identification of other GAG-glycated/glycosylated proteins and the characterization of the different isoforms of glycated uromodulin and albumin would allow enhancing the knowledge relating to the physiopathology of the disease, and may lead to the discovery of new therapeutic targets.

The method of the invention is also useful for finding other peptides within any protein that may be altered in certain pathologies and may be used as biomarkers in glycosylation/glycation-related pathologies.

The homogenous urinary profile observed in the general population is altered in patients with kidney disease on a protein level and it could be used as kidney function and prognostic biomarker, where changes in the levels of creatinine, the current reference biomarker for kidney damage, are anticipated several years in advance since 50% of the kidney function may have been lost before the levels of creatinine change significantly.

Knowing that exosomes interact with the primary cilium and that they are taken up by at least the cells of the collecting tubule, it is suggested that the UGE (uromodulin-glycosaminoglycan-exosomes) complex may be directing the communication between the different segments of the nephron. This communication may be related to the immune system as a result of the identification of the content of the exosomes, as well as of the previously described function of uromodulin as an immunity agent (trap for pathogens, inflammation mediator, or macrophage and granulocyte activator).

With the discovery of the uromodulin-glycosaminoglycan-exosomes complexes, the role played by uromodulin and GAGs both in communication and in the immune system at a renal level which is unknown up to now and that can furthermore be monitored in an easy and cost-effective manner in the urine for use as diagnostic/prognostic biomarkers for a kidney disease given the identification of a characteristic profile, is now clearly shown. It is suggested that these UGE complexes, and therefore this communication mechanism, are lost when kidney damage/failure progresses, causing the deregulation of nephron segments and alterations in the immune system. These mechanisms furthermore establish the basis for the development of possible therapies and the application of corrective measures before reaching an advanced stage of kidney disease. This technique and the discovery of this PGE signaling complex can furthermore be extrapolated to any biological fluid.

The invention furthermore allows, starting from a 1 ml urine sample and using a cellulose acetate gel, differentiating individuals suffering from mucopolysaccharidosis from healthy individuals; and also allows differentiating between the different mucopolysaccharidoses as demonstrated in FIG. 17. The method commonly used for the diagnosis of mucopolysaccharidoses is extremely laborious and difficult, requiring the use of about two days; whereas the method of the invention allows said diagnosis to be performed in a quick and simple manner where it needs only about 4 hours.

The invention claimed is:

1. An in vitro method for separating free sulfated glycosaminoglycans (GAGs) and the fraction associated with sulfated GAGs from a sample, which comprises:
   a) contacting a sample with the dimethylmethylene blue (DMB) dye at an acidic pH comprised between 2 and 6.9;
   b) incubating the mixture from a) at a temperature comprised between 0° C. and 40° C. for the time required for the formation of a precipitate;
   c) removing the supernatant; and
   d) recovering the precipitate containing free sulfated GAGs and the fraction associated with sulfated GAGs, wherein the fraction associated with sulfated GAGs is a fraction containing exosomes.

2. The method according to claim 1, wherein the fraction associated with sulfated GAGs is a complex selected from the group consisting of:
   (i) a complex formed by uromodulin or a variant thereof and exosomes,
   (ii) a complex formed by albumin or a variant thereof and exosomes,
   (iii) a complex formed by IgA or a variant thereof and exosomes, and
   (iv) a complex formed by IgG or a variant thereof and exosomes.

3. An in vitro identification method for identifying the profile of proteins associated with sulfated GAGs of a sample selected from the group consisting of:
   A) a method which comprises:
      a) separating the protein fraction associated with sulfated GAGs from a sample according to the method of claim 1;
      b) separating the product obtained in a) by electrophoresis; and
      c) identifying the electrophoretic profile obtained in b); and
   B) a method which comprises:
      a) separating the protein fraction associated with sulfated GAGs from a sample according to the method of claim 1, and
      b) identifying the profile of proteins associated with sulfated GAGs by means of chromatography or mass spectrometry of the fraction obtained in a).

4. An in vitro method for detecting an alteration in the pattern of glycosylation by sulfated GAGs of a sample, which comprises:
   a) identifying the profile of proteins associated with sulfated GAGs of a sample according to the method of claim 3; and
   b) comparing the profile of proteins associated with sulfated GAGs obtained in a) with the profile obtained for a reference sample, wherein a difference in the profile obtained in a) with respect to the profile obtained in the reference sample indicates an alteration in the pattern of glycosylation by sulfated GAGs.

5. A method for identifying protein biomarkers associated with sulfated GAGs comprising using a method according to claim 3.

6. A method for identifying protein biomarkers associated with sulfated GAGs comprising using a method according to claim 4.

7. The method according to claim 1, wherein the sample is a sample of exosomes.

* * * * *